(12) United States Patent
Tymianski et al.

(10) Patent No.: US 9,073,976 B2
(45) Date of Patent: Jul. 7, 2015

(54) ND2 PEPTIDES AND METHODS OF TREATING NEUROLOGICAL DISEASE

(71) Applicant: NoNO Inc., Toronto (CA)

(72) Inventors: Michael Tymianski, Toronto (CA); Rongwen Li, Toronto (CA); Jonathan David Garman, Thornhill (CA)

(73) Assignee: NoNO Inc. (CA)

( * ) Notice: Subject to any disclaimer, the term of this patent is extended or adjusted under 35 U.S.C. 154(b) by 0 days.

(21) Appl. No.: 13/842,848

(22) Filed: Mar. 15, 2013

(65) Prior Publication Data

US 2014/0274906 A1 Sep. 18, 2014

Related U.S. Application Data

(63) Continuation-in-part of application No. PCT/US2011/053764, filed on Sep. 28, 2011.

(60) Provisional application No. 61/387,439, filed on Sep. 28, 2010.

(51) Int. Cl.
| | |
|---|---|
| C07K 14/00 | (2006.01) |
| C12N 9/02 | (2006.01) |
| C07K 7/06 | (2006.01) |
| A61K 38/00 | (2006.01) |

(52) U.S. Cl.
CPC ............... *C07K 14/00* (2013.01); *A61K 38/00* (2013.01); *C07K 2319/10* (2013.01); *C07K 2319/22* (2013.01); *C07K 2319/23* (2013.01); *C12N 9/0036* (2013.01); *C12Y 106/05003* (2013.01); *C07K 7/06* (2013.01)

(58) Field of Classification Search
CPC ............ A61K 38/00; C07K 7/00; C07K 7/08; C07K 14/435; C07K 2319/10; C07K 2319/70
See application file for complete search history.

(56) References Cited

U.S. PATENT DOCUMENTS

| | | | |
|---|---|---|---|
| 7,425,540 B2 | 9/2008 | Salter et al. | |
| 8,003,609 B2 | 8/2011 | Salter et al. | |
| 8,158,749 B2 | 4/2012 | Salter et al. | |
| 2002/0168724 A1* | 11/2002 | Blanar et al. | 435/69.1 |
| 2005/0222042 A1* | 10/2005 | Salter et al. | 514/16 |
| 2005/0281812 A1* | 12/2005 | Cohen et al. | 424/143.1 |
| 2007/0059320 A1 | 3/2007 | Salter et al. | |
| 2007/0060516 A1* | 3/2007 | Kaumaya et al. | 514/12 |
| 2008/0153768 A1* | 6/2008 | Dorn et al. | 514/44 |
| 2012/0029168 A1 | 2/2012 | Salter et al. | |
| 2013/0288974 A1 | 10/2013 | Salter et al. | |

FOREIGN PATENT DOCUMENTS

| | | |
|---|---|---|
| WO | WO 2005/095593 A1 | 10/2005 |
| WO | WO 2008/025130 A1 | 3/2008 |
| WO | WO 2008/109010 A1 | 9/2008 |

OTHER PUBLICATIONS

Nelson et al. 2007 "Myristoyl-based transport of peptides into living cells" Biochemistry 46(51):14771-14781.*
Barszczyk, "A peptide comprising the Src-interacting domain of NAM Dehydrogenase Subunit 2 alleviates complete Freund's adjuvant-induced allodynia in rats," Master theses. Department of Physiology, University of Toronto, (2010).
EPO Application No. EP 11833072.9, Supplementary European Search Report and European Search Opinion, mailed Apr. 18, 2014.
Gingrich et al., "Correction to Unique domain anchoring of Src to synaptic NMDA receptors via the mitochondrial protein NADH dehydrogenase subunit 2," PNAS, 103(25):9744-9745, (2006).
Gingrich et al., "Unique domain anchoring of Src to synaptic NMDA receptors via the mitochondrial protein NADH dehydrogenase subunit 2," PNAS, 101(16):6237-6242, (2004).
Liu et al. , "Treatment of inflammatory and neuropathic pain by uncoupling Src from the NMDA receptor complex," Nature Medicine, 14(12):1325-1332, (2008).
UniProt Database: Accession No. Q36734, "SubName: Full.NADH dehydrogenase subunit 2; Flags: Fragment," Nov. 1, 1996.
UniProt Database: Accession No. Q7GHE2, "SubName: Ful14ADH dehydrogenase subunit 2; Flags: Fragment;" Jul. 5, 2004.
WIPO Application No. PCT/US2011/053764, International Search Report and Written Opinion of the International Searching Authority, mailed Apr. 26, 2012.

* cited by examiner

*Primary Examiner* — Gregory S Emch
*Assistant Examiner* — Adam M Weidner
(74) *Attorney, Agent, or Firm* — Alston & Bird LLP

(57) ABSTRACT

The invention is based in part on identifying a core region of ND2 responsible for interacting with Src to within residues 289-321 of ND2 and more particularly residues 307-321 or 310-321 of ND2. Peptides including, overlapping or from within this region can be used to inhibit ND2 interaction with Src Inhibition of this interaction is useful for treatment or prophylaxis of neurological diseases and disorders, pain and cancer.

19 Claims, 24 Drawing Sheets

Figures 1A, B, C
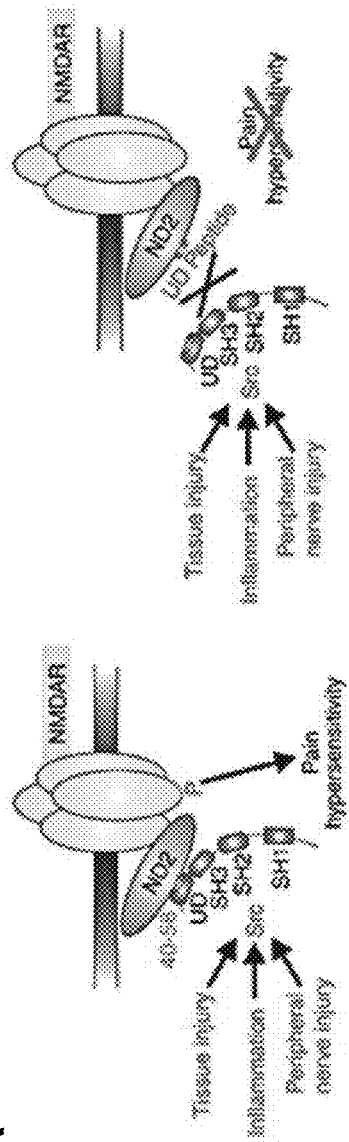
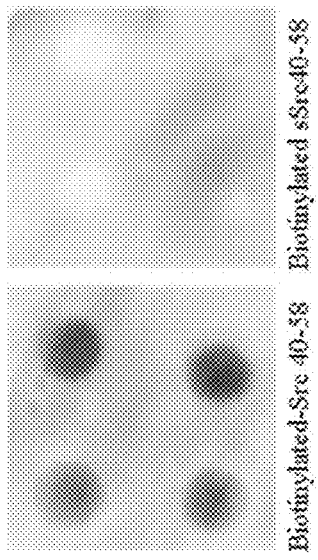
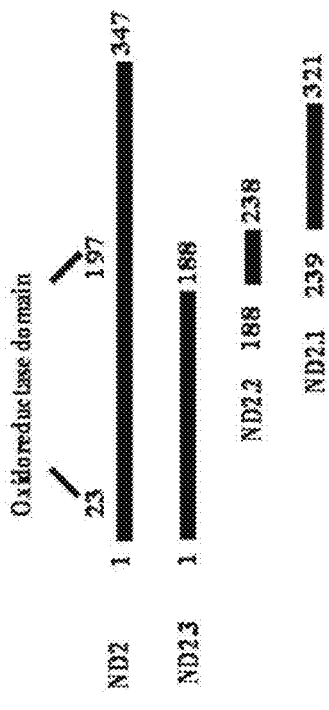

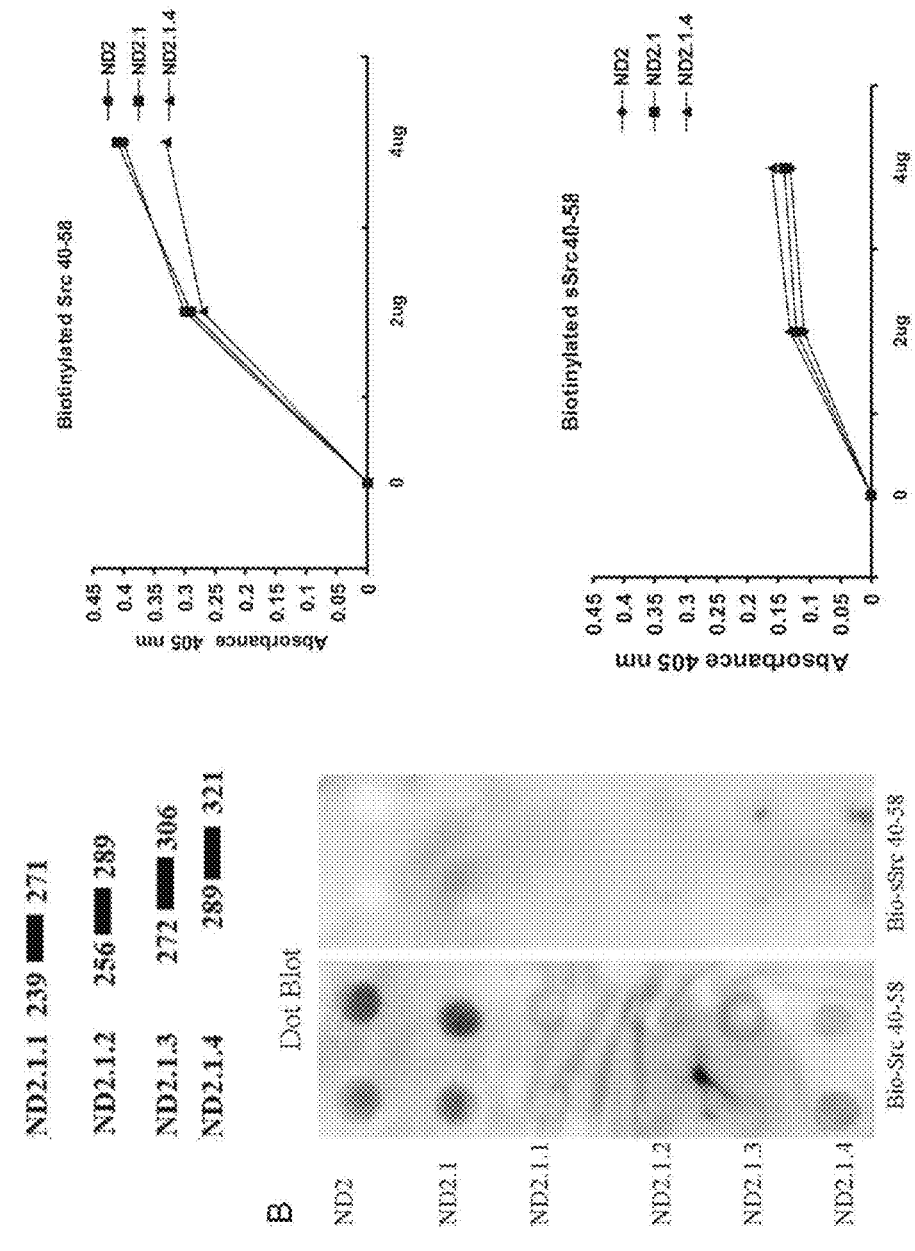
Figures 2A-C

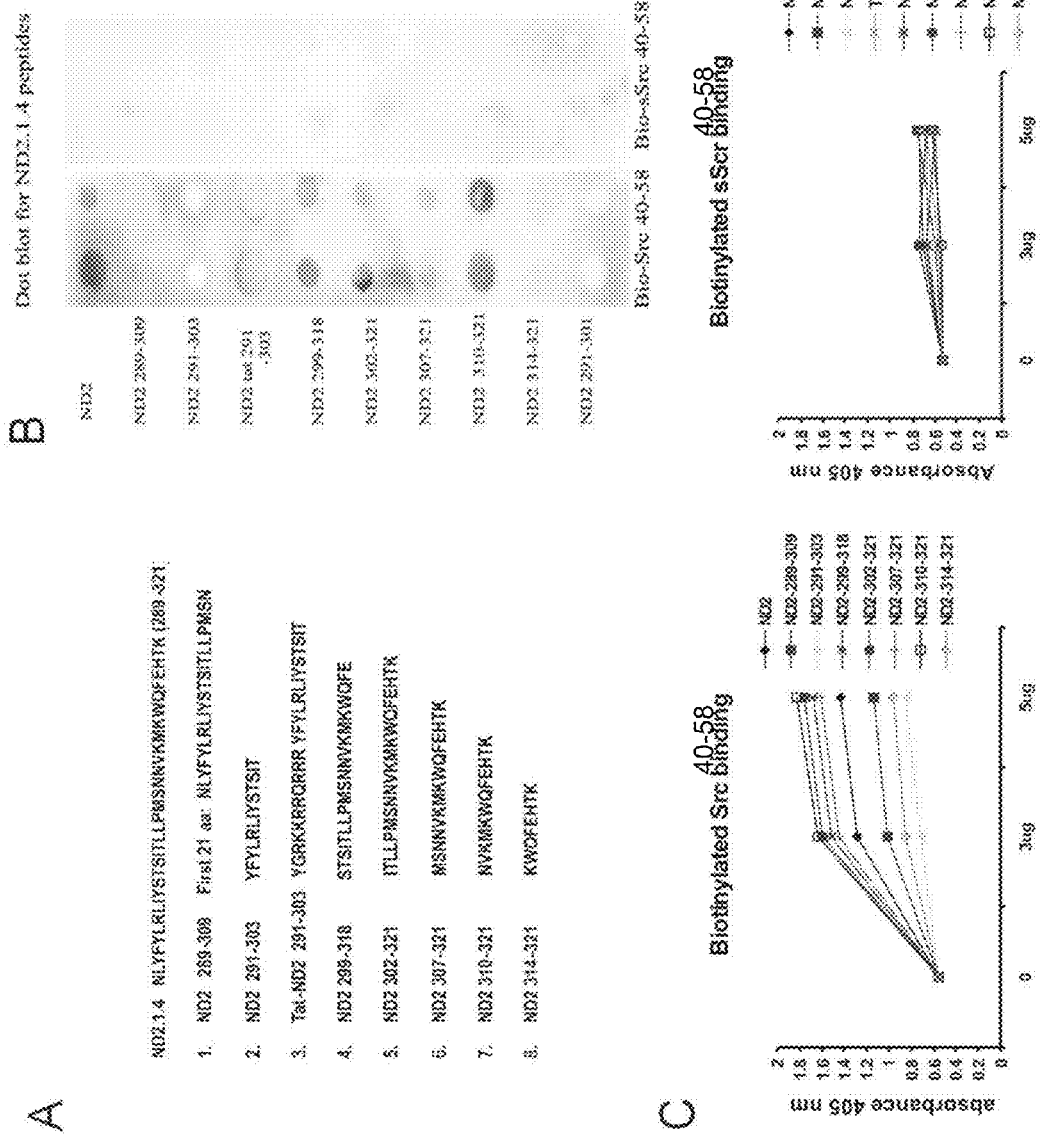
Figures 3A-C

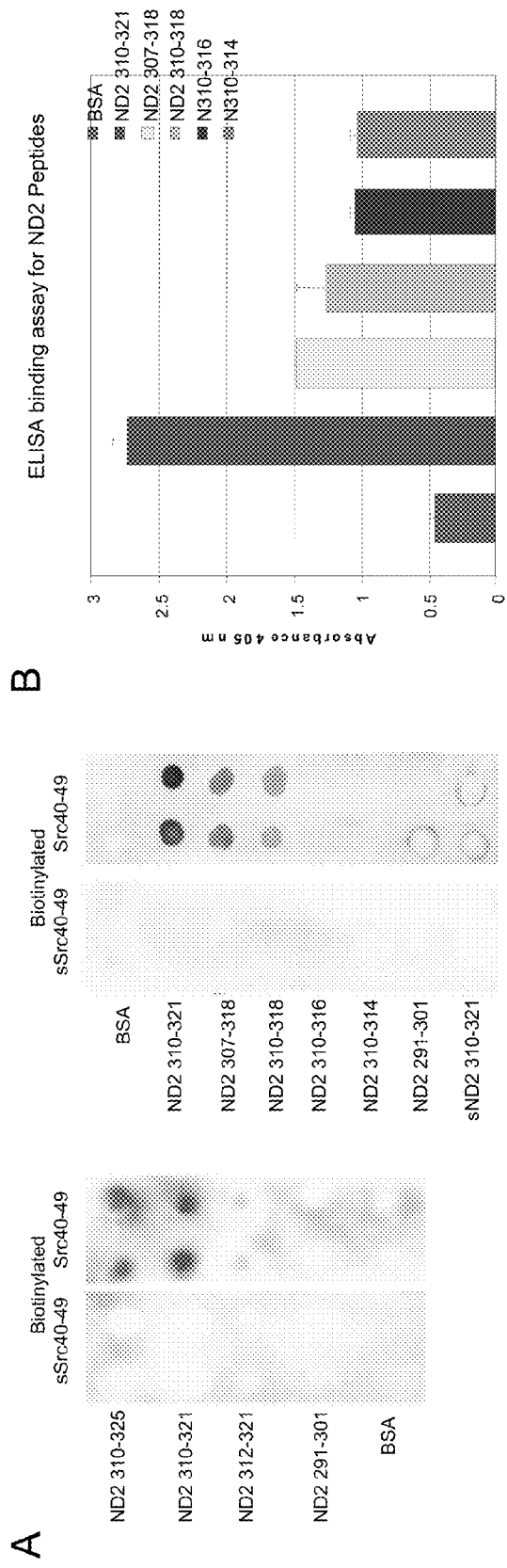
Figures
4A, B  Isolation of specific segment of ND2 responsible for interaction with Src40-49

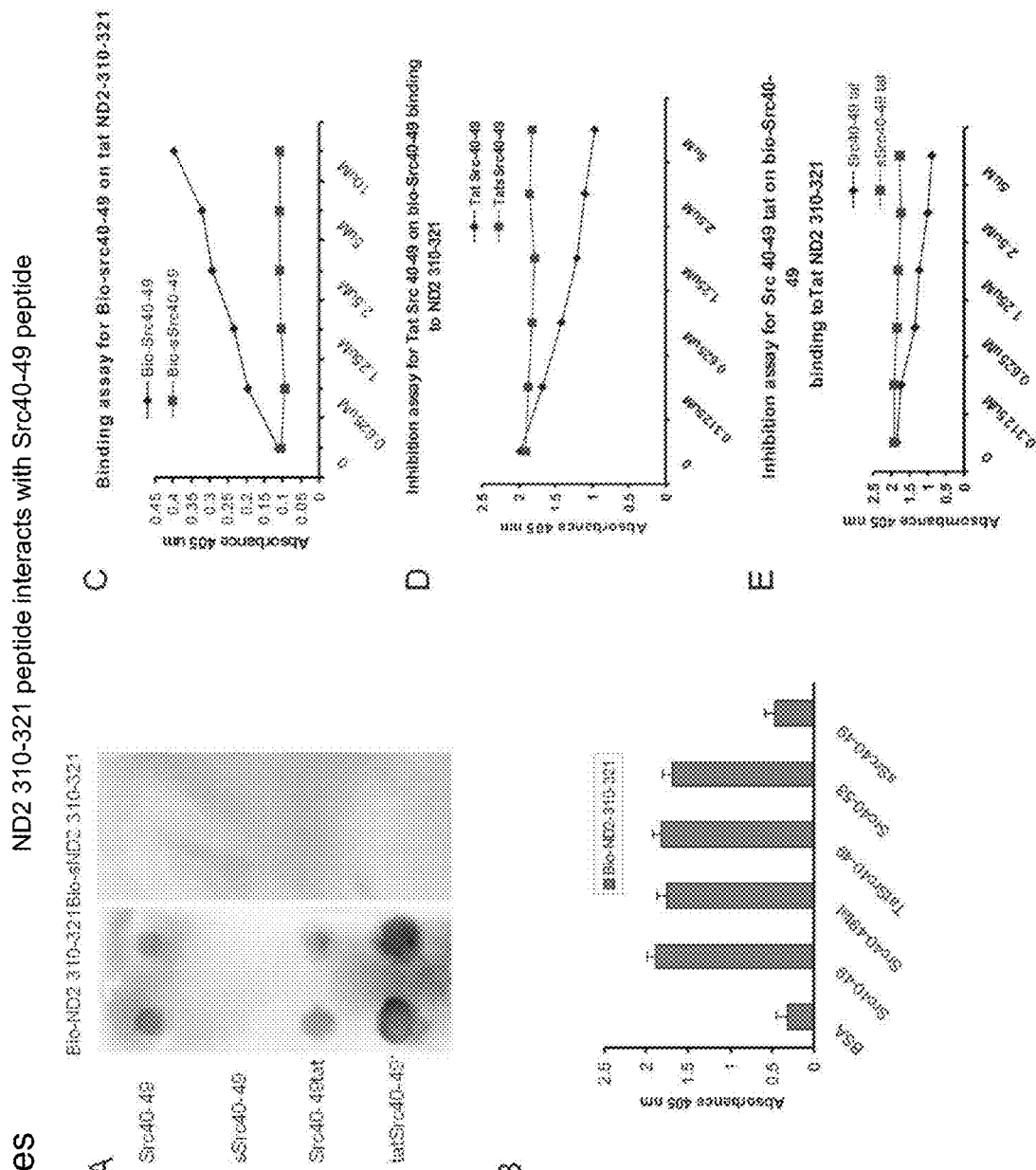
Figures 5A-E

Figures 8A, B
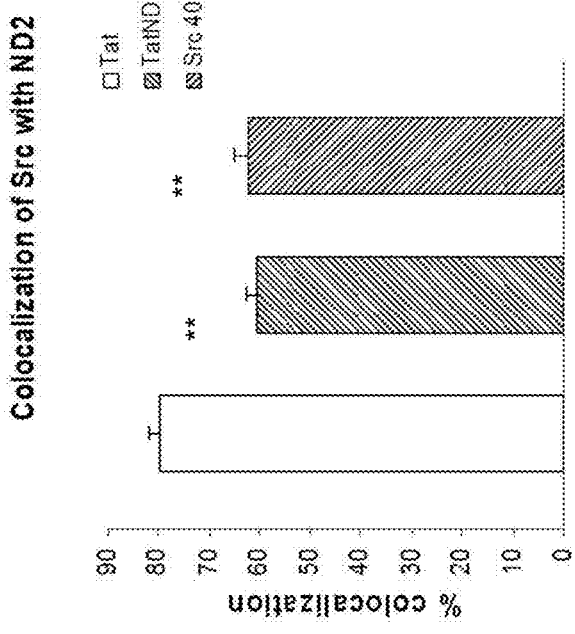
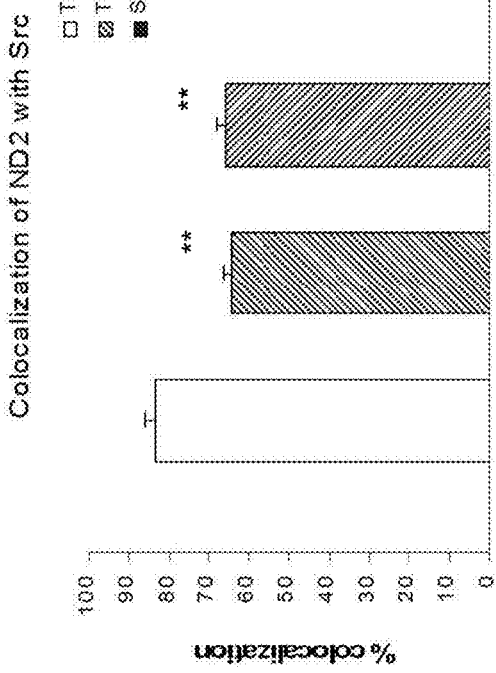

Figures 9A-D
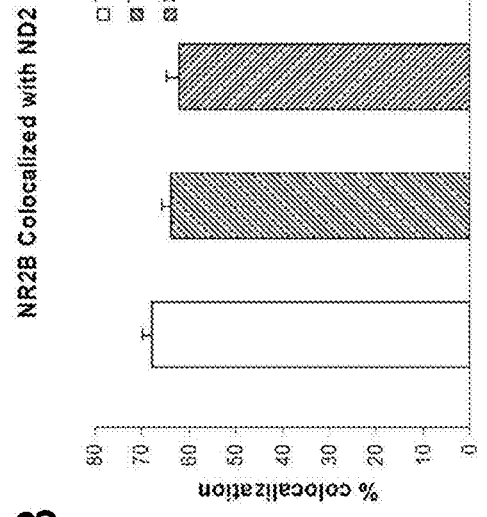
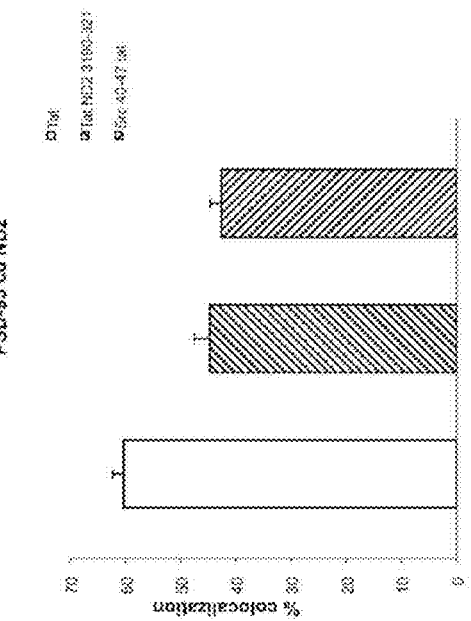
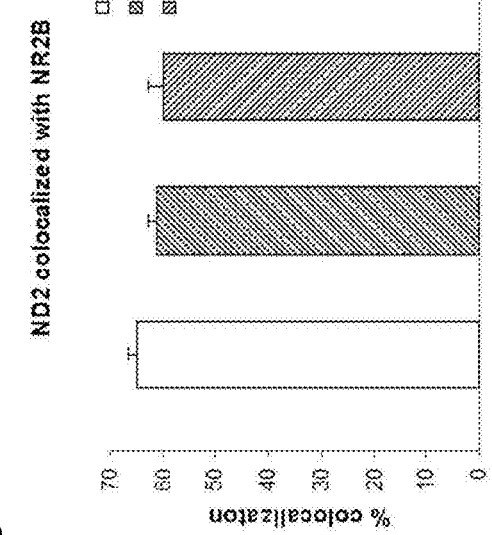
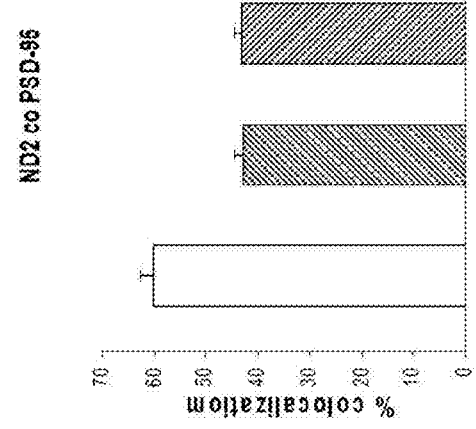

Figures 9E-F
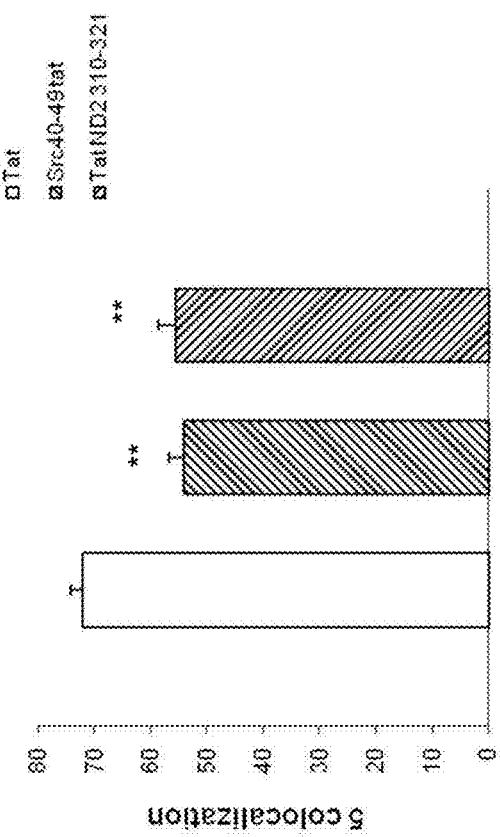
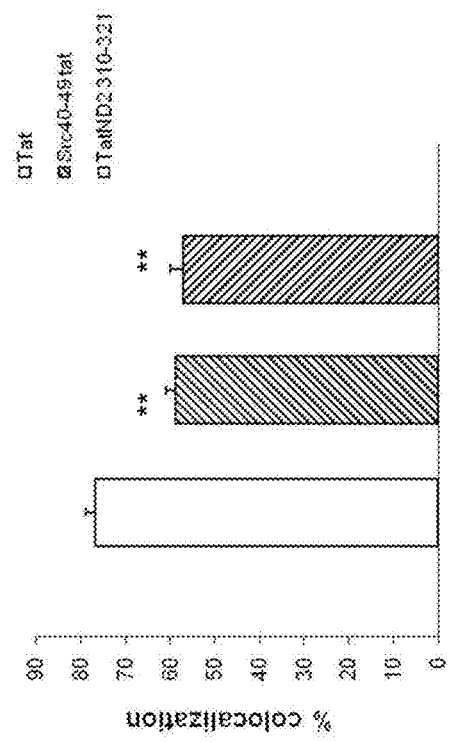

Figures
12A-E
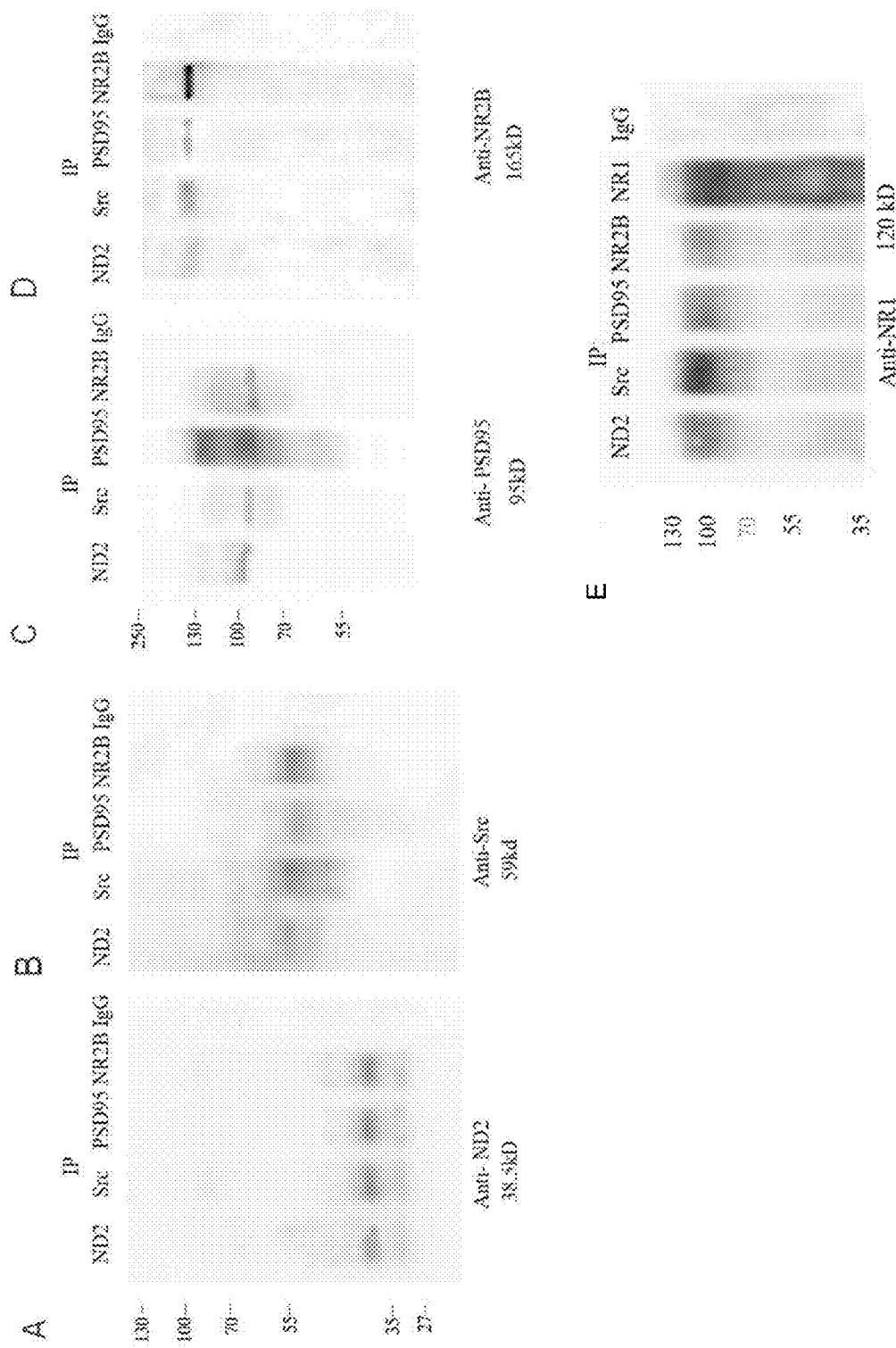
A complex of the ND2, Src,PSD95,NR2B and NR1 in rat brain lysates

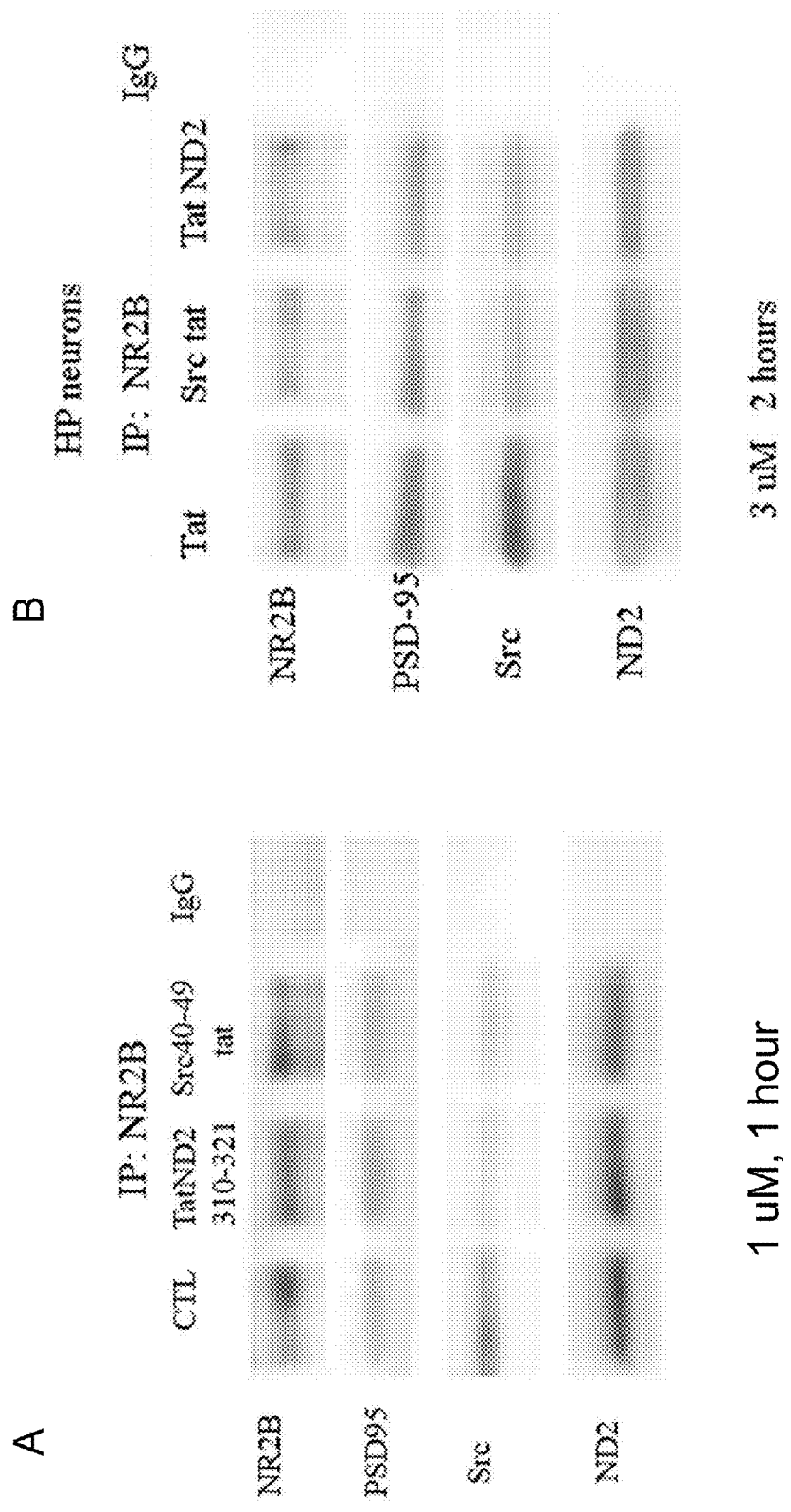
Figures 13A, B

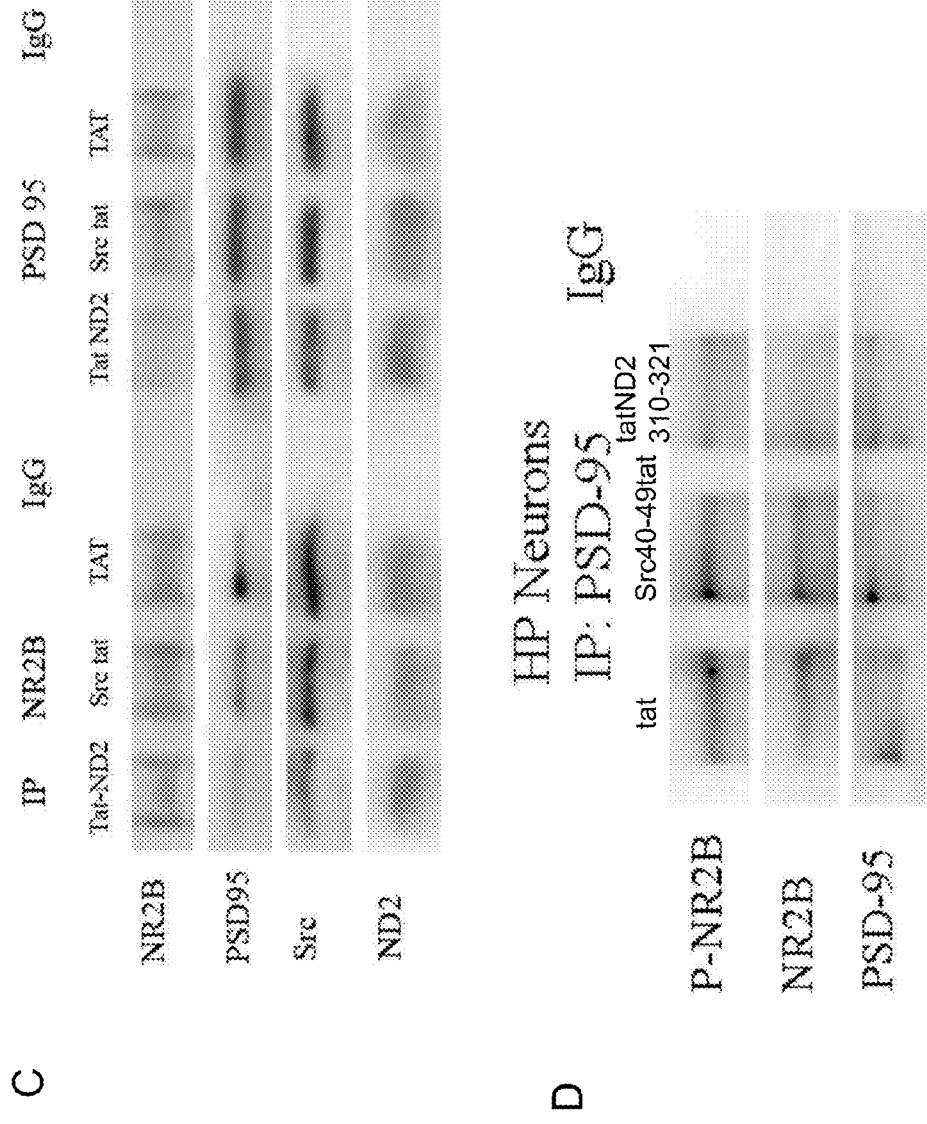
Figures 13C, D

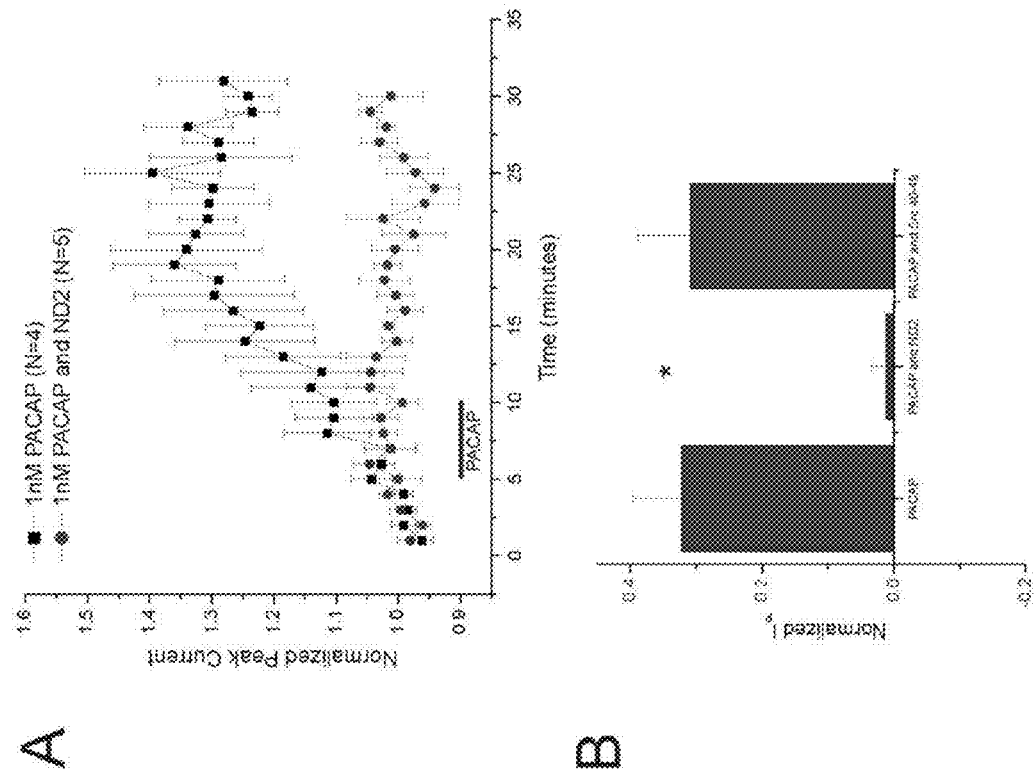
Figures 14A, B

Figures 16A, B

ND2 PEPTIDES AND METHODS OF TREATING NEUROLOGICAL DISEASE

CROSS-REFERENCE TO RELATED APPLICATIONS

The present application is a continuation-in-part of PCT/US2011/053764, filed Sep. 28, 2011, which is a non-provisional and claims the benefit of 61/387,439, each of which is incorporated by reference in its entirety for all purposes.

INCORPORATION BY REFERENCE OF SEQUENCE LISTING

This application incorporates by references sequences disclosed in txt file designated 431202SEQLIST.TXT of 18 kbytes, and created Mar. 15, 2013.

BACKGROUND

The N-methyl D-aspartic acid receptor (NMDAR) complex includes more than 60 proteins [4]. The NMDAR complex has been reported to be associated with several neurological diseases and disorders, including stroke, neurotrauma, neurodegenerative diseases, memory and long term potentiation, optical and aural neuropathies, pain, and more. However, several attempts to inhibit the NMDAR complex directly have failed in the clinic because of excessive side effects.

Post-synaptic Density protein 95 kD (PSD95) binds directly to the C-terminal NR2 subunits of the NMDAR [11] via its first two PDZ domains, PDZ1 and PDZ2 [12]. It has been reported that that disrupting the interaction between PSD95 and NMDAR can protect animals from the damaging effects of stroke without blocking the electrical and calcium flux activities of the NMDAR[13].

NADH dehydrogenase subunit 2 (ND2) has been reported to associate with the tyrosine kinase Src (see FIG. 1A). Src is one of several Src family kinases (SFKs) in the NMDAR complex (i.e. Src, Fyn, Lyn and Yes) [5-7]. Src is involved in the control of many functions, including cell adhesion, growth, movement and differentiation. Src is widely expressed in many cell types, and can have different locations within a cell. It appears that the subcellular location of Src can affect its function. Src can associate with cellular membranes, such as the plasma membrane, the perinuclear membrane and the endosomal membrane. At the plasma membrane, Src can transduce signals from a variety of receptors to internal signalling pathways that convey these signals to the nucleus, cytoskeleton and other cellular components. For example, Src can act through the growth factor receptors to affect cell growth and proliferation.

A presumed molecular arrangement between NMDARs, Src and ND2 has been presented in of Liu et al., Nat Med 2008, in which Src is assumed to interact with NMDARs via ND2 which acts as an adapter protein. ND2 anchors Src to the N-methyl-d-aspartate (NMDA) receptor complex in postsynaptic densities (PSDs) to regulate NMDA receptor activity. It has been reported a fragment of Src termed Src 40-49-Tat can inhibit interactions between Src and ND2 at excitatory synapses in the brain, reducing phosphorylation of NR2B subunits and modulating pain [1, 2, 3].

SUMMARY OF THE CLAIMED INVENTION

The invention provides an ND2 peptide having an amino acid sequence consisting of amino acids 307 to 321 or 310 to 321 of SEQ ID NO:60 provided that up to six amino acids can be deleted, inserted or conservatively substituted. An ND2 peptide including any of the peptides mentioned above can have an amino acid sequence consisting of 4-12 contiguous residues between amino acids 307-321 or 310-321 of SEQ ID NO:60. Optionally, the ND2 peptide has an amino acid sequence consisting of 4-10 contiguous residues between amino acids 307-321 or 310-321 of SEQ ID NO:60. Optionally, the ND2 peptide consists of amino acids 307-321 or 310-321. Any of these ND2 peptides can be lipidated, for example, by being linked to a fatty acid. Preferably an ND2 peptide is myristoylated. Any of these ND2 peptides can be linked to an internalization peptide at the N-terminus or C-terminus of the ND2 peptide, for example as a fusion protein. The internalization peptide can include at least 5 arginine or lysine residues and has a total length of up to 15 amino acids. The internalization peptide can be a Tat peptide.

The invention provides a chimeric peptide up to 50 amino acids in length. The peptide comprises an ND2 peptide comprising at least 3 contiguous amino acids located between amino acids 289 and 321 of SEQ ID NO:60. The ND2 peptide is linked to an internalization peptide and/or the ND2 peptide is lipidated. Optionally, the chimeric peptide is up to 25 amino acids in length. Optionally, the ND2 peptide has an amino acid sequence consisting of 4-20 contiguous residues between amino acids 289 and 321 of SEQ ID NO:60. Optionally, the ND2 peptide has an amino acid sequence consisting of 4-12 contiguous residues between amino acids 307-321 or 310-321 of SEQ ID NO:60. Optionally, the ND2 peptide has an amino acid sequence consisting of 4-10 contiguous residues between amino acids 307-321 or 310-321 of SEQ ID NO:60. Optionally, the ND2 peptide consists of amino acids 307-321 or 310-321 of SEQ ID NO:60 provided that up to six amino acids can be deleted, inserted or substituted. Optionally, the ND2 peptide has an amino acid sequence consisting of amino acids 307-321 or 310 to 321 of SEQ ID NO:60. Optionally, the internalization peptide is linked to the N-terminus of ND2 peptide. Optionally, the internalization peptide is linked to the C-terminus of the ND2 peptide. Optionally, the internalization peptide and ND2 peptide are linked as a fusion peptide. Optionally, the internalization peptide includes at least 5 arginine or lysine residues and has a total length of up to 15 amino acids. Optionally, the internalization peptide is a Tat peptide. The invention further provides an ND2 peptide having 4-40 residues identical to residues of SEQ ID NO:60 of which at least 4 of the residues are contiguous residues between amino acids 289-321 of SEQ ID NO:60.

The invention further provides a peptidomimetic of a chimeric peptide or an ND2 peptide as described above. Optionally, the peptidomimetic is a retro-inverso peptidomimetic.

The invention further provides a method of treating or effecting prophylaxis of a neurological disease or disorder, comprising administering an effective regime of a chimeric peptide, ND2 peptide or peptidomimetic of any preceding claim to a patient having or at risk of developing a neurological disorder. Optionally, the neurological disease or disorder is stroke, traumatic injury to the CNS, epilepsy, anxiety, or a neurodegenerative disease.

The invention further provides a method of treating or effecting prophylaxis of pain, comprising administering an effective regime of a chimeric peptide, an ND2 peptide, or peptidomimetic as described above to a patient having or at risk of developing pain. Optionally, the pain is neuropathic or inflammatory pain.

The invention further provides a method of treating or effecting prophylaxis of cancer, comprising administering an effective regime of chimeric peptide, ND2 peptide or peptidomimetic as described above to a patient having or at risk of developing cancer.

The invention further provides a method of identifying an agent that inhibits ND2-Src interaction, comprising contacting a Src peptide and ND2 peptide with an agent; and determining binding between the Src peptide and ND2 peptide, wherein reduced binding in the presence of the agent relative to a control assay lacking the agent indicates the agent is an inhibitor of Src-ND2 interaction; wherein the agent is a chimeric or ND2 peptide or a peptidomimetic thereof as defined above or anywhere herein.

The invention further provides a method of identifying an agent that inhibits Src-ND2 interaction, comprising contacting a Src peptide and an ND2 peptide as defined above with an agent; and determining binding between the Src peptide and ND2 peptide, wherein reduced binding in the presence of the agent relative to a control assay lacking the agent indicates the agent is an inhibitor of Src-ND2 interaction. Such a method can also include testing the agent for pharmacological activity against a neurological disease, pain or cancer in an animal model of one of neurological disease, pain or cancer.

BRIEF DESCRIPTION OF THE FIGURES

FIGS. 1A, B, C: ND2 interacts with Src. A. Cartoon depicting the interactions in the Src-ND2-NMDAR Complex. B. Structure of different ND2 sequences design to identify the Src-interacting domain. C. Dot blot demonstrating that the Src-interacting sequences of ND2 reside between amino acids 239 and 321.

FIGS. 2A, B, C: A. Structure of ND2 fragments used in the experiment, with numbers representing amino acids relative to full length ND2. B. Dot blot demonstrating that biotinylated Src 40-58, but not the scrambled sSRC 40-58, can bind to ND2, ND2.1 and ND 2.1.4 better than ND2.1.3. C. ELISA demonstrating ND2, ND2.1 and ND2.1.4 can all bind biotinylated Src 40-58.

FIGS. 3A-C: A. Sequence of ND2 constructs assessed for binding to Src 40-58 (SEQ ID NOS 16-23 and 25, respectively, in order of appearance). B. Dot blot showing binding of ND2 sequences to Src 40-58. C. ELISA demonstrating binding of ND2 constructs to Src 40-58 but not to a scrambled control.

FIGS. 4A, B: Dot blots of ND2 fragments demonstrating binding to Src 40-58, with strong binding from ND2 310-321, ND2 307-318, and ND2 310-318. B. ELISA demonstrating binding of ND2 constructs to Src 40-58.

FIGS. 5A-E: A. Dot blot demonstrating biotinylated ND2 310-321 can bind to Src 40-49 and versions of Src 40-49 with Tat at the amino or carboxy terminal end. B. ELISA demonstrating the same including binding to Src 40-58. C. ELISA assay demonstrating Src 40-49 can bind Tat-ND2 310-321. D-E. ELISA assays demonstrating Src 40-49 and Tat Src 40-49 can compete for binding to ND2 310-321 or Tat ND2 310-321.

FIGS. 8A, B: Quantification of the co-localization of ND2 with Src in 14DIV hippocampal neurons with and without treatment with Tat-ND2 310-321 or Src 40-49-Tat.

FIGS. 9A-F: Quantification of the co-localization of proteins in the NMDAR complex in 14DIV hippocampal neurons with and without treatment with Tat-ND2 310-321 or Src 40-49-Tat. A. ND2 with NR2B. B. NR2B with ND2. C. ND2 with PSD95. D. PSD95 with ND2. E. NR2B with PSD95. F. PSD95 with NR2B.

FIGS. 12A-E. Immunoprecipitation experiments from rat brain lysates showing that antibodies against ND2, Src, PSD95, NR2B and NR1 can all immunoprecipitate a complex containing the other proteins.

FIGS. 13A-D. A Immunoprecipitation using anti-NR2B antibody from 14DIV hippocampal neurons that have been treated with control, Tat-ND2 310-321 or Src 40-49-Tat at 1 uM for 1 hour. B. Same, treated with 3 uM for 2 hours. C. Repeat of A using the indicated antibody for IP. D. Similar to A, using anti-PSD95 as the immunoprecipitation antibody.

FIGS. 14A, B: ND2 310-321 inhibits PACAP-enhanced NMDA-evoked currents but Src 40-49 does not.

DEFINITIONS

Figure 7:
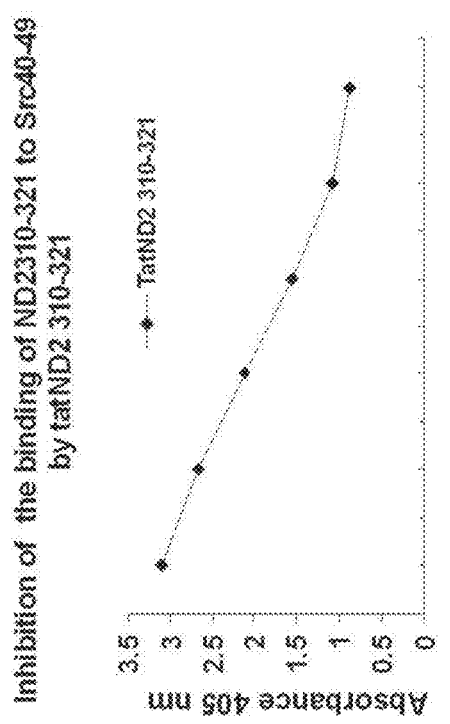
FIG. 7: ELISA demonstrating Tat-ND2 310-321 is able to compete for binding against Src 40-49 bound to ND2 310-321.

A "chimeric peptide" means a peptide having two component peptides not naturally associated with one another joined to one another as a fusion protein or by chemical linkage.

A "fusion" protein or polypeptide refers to a composite polypeptide, i.e., a single contiguous amino acid sequence, made up of sequences from two (or more) distinct, heterologous polypeptides which are not normally fused together in a single polypeptide sequence.

Agents are usually provided in isolated form. Isolated means that an object species (e.g., a peptide) has been at least partially separated from contaminants with which it is naturally associated or which are used in its manufacture but does not necessarily exclude the presence of other components intended to act in combination with an isolated species, such as an internalization peptide or pharmaceutical excipient. Preferably an agent is the predominant macromolecular (e.g., polypeptide) species present in a sample (i.e., on a molar basis in a composition and typically comprises at least about 50 percent (on a molar basis) of all macromolecular species present. Generally, an isolated pharmacologic agent comprises more than 80 to 90 percent of all macromolecular species present in a composition. Most preferably, a pharmacological agent is purified to essential homogeneity (i.e., contaminant species cannot be detected in a composition by conventional detection methods), such that the composition consists essentially of a single macromolecular species.

The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay). Specific binding can be the result of formation of bonds between particular functional groups or particular spatial fit (e.g., lock and key type) whereas nonspecific binding is usually the result of van der Waals forces.

Excitotoxicity is the pathological process by which neurons are damaged and killed by the overactivation of glutamate receptors, such as NMDA receptors.

The term "patient" or "subject" includes humans and other mammals, particularly, rodents, cats, dogs, ungulates, porcines and nonhuman primates.

The term "agent" includes any element, compound, or entity that has or may have pharmacologic activity. Agents can be biologics (e.g., peptides, peptidomimetics, or antibodies) or organic small molecules (usually less than 500 Da) among others. Agents can be products of nature or synthetic compound. Agents include compounds that are known (i.e., approved by FDA or similar body in other countries) drugs, compounds for which pharmacological activity has been identified but which are undergoing further evaluation, or compounds that being screened for a pharmacologic activity.

An agent can be described as having pharmacological activity if it exhibits an activity in a screening system that indicates that the active agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

Unless otherwise apparent from the context, reference to an agent means the agent or pharmacological agent either alone or linked to an internalization peptide.

A Tat (or TAT or tat) peptide means a peptide comprising or consisting of GRKKRRQRRR (SEQ ID NO:1), in which no more than 5 residues are deleted, substituted or inserted within the sequence, which retains the capacity to facilitate uptake of a linked peptide or other agent into cells. Preferably any amino acid changes are conservative substitutions. Preferably, any substitutions, deletions or internal insertions in the aggregate leave the peptide with a net cationic charge, preferably similar to that of the above sequence. The amino acids of a Tat peptide can be derivatized with biotin or similar molecule to reduce an inflammatory response.

Statistically significant refers to a p-value that is <0.05, preferably <0.01 and most preferably <0.001.

When a peptide or amino acid sequence is said to occur within a range or amino acids, the peptide can include the beginning and end point defining the range as well as amino acids in between.

For purposes of classifying amino acid substitutions as conservative or nonconservative, amino acids may be grouped as follows: Group I (hydrophobic side chains); met, ala, val, leu, ile; Group II (neutral hydrophilic side chains): cys, ser, thr; Group III (acid side chains): asp, glu; Group IV (basic side chains): asn, gln, his, lys, arg; Group V (residues influencing chain conformation): gly, pro; and Group VI (aromatic side chains): trp, tyr, phe. Conservative substitutions involve substitutions between amino acids in the same group. Non-conservative substitutions constitute exchanging a member of one of these groups for a member of another.

A peptide is maximally aligned with a reference sequence when the number of exact matches between the peptide and the reference sequence is maximized Aligned can be performed by eye. Alternatively, Software for performing BLAST analyses is publicly available through the National Center for Biotechnology Information (http://www.ncbi.nlm.nih.gov/). Typically, default program parameters can be used. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89, 10915 (1989)).

A peptide occurring within a specified range of amino acids can include a peptide including either or both amino acids defining the limits of the range as well as a peptide including only amino acids in between the amino acids defining the range.

DETAILED DESCRIPTION

I. General

The invention is based in part on identifying a core region of ND2 responsible for interacting with Src to within residues 289-321 of ND2 and more particularly residues 307-321 or 310-321 of ND2. Peptides including, overlapping or from within this region can be used to inhibit ND2 interaction with Src Inhibition of this interaction is useful for treatment or prophylaxis of neurological diseases and disorders, pain and cancer.

II. Proteins

Figure 19:
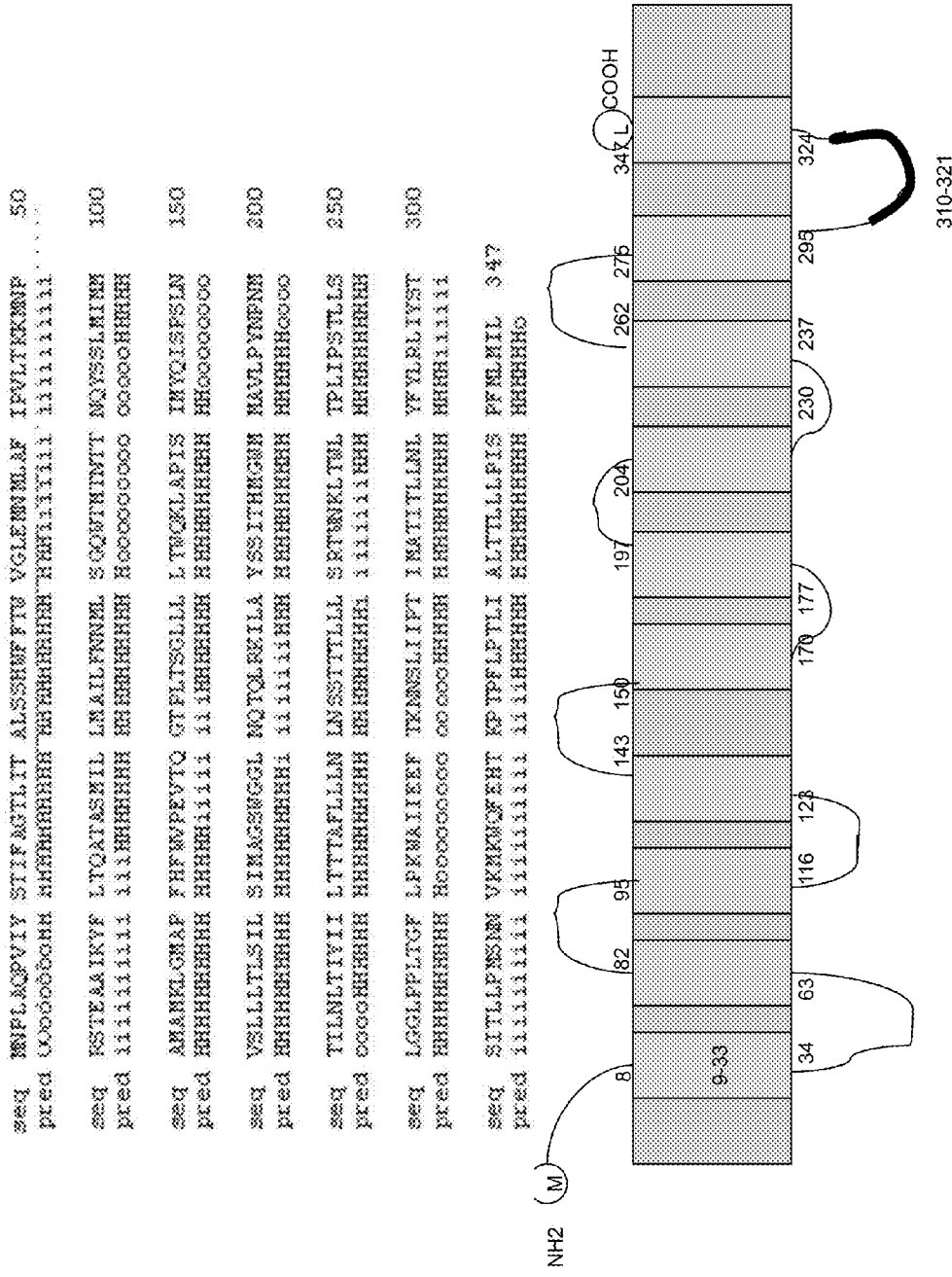
FIG. 19: Sequence of ND2, with predicted membrane topology. The location of 310-321 is highlighted and predicted to be intracellular.

Unless otherwise apparent from the context, ND2 protein refers to a natural human form of ND2, for which an exemplary sequence is assigned Swiss Prot P03891 and reproduced below and in FIG. 19. The initial M residue can be cleaved off. About 20 single amino acid natural variants of the sequence are listed in the Swiss-Prot database.

(SEQ ID NO: 60)

```
           10         20         30         40         50         60
    MNPLAQPVIY STIFAGTLIT ALSSHWFFTW VGLEMNMLAF IPVLTKKMNP RSTEAAIKYF 70         80         90        100        110        120
    LTQATASMIL LMAILFNNML SGQWTMTNTT NQYSSLMIMM AMAMKLGMAP FHFWVPEVTQ
```

-continued

```
         130        140        150        160        170        180
GTPLTSGLLL LTWQKLAPIS IMYQISPSLN VSLLLTLSIL SIMAGSWGGL NQTQLRKILA 190        200        210        220        230        240
YSSITHMGWM MAVLPYNPNM TILNLTIYII LTTTAFLLLN LNSSTTTLLL SRTWNKLTWL 250        260        270        280        290        300
TPLIPSTLLS LGGLPPLTGF LPKWAIIEEF TKNNSLIIPT IMATITLLNL YFYLRLIYST 310        320        330        340
SITLLPMSNN VKMKWQFEHT KPTPFLPTLI ALTTLLLPIS PFMLMIL
```

Likewise unless otherwise indicated, Src means a natural human sequence of Src, such as is provided by Swiss-Prot. P12931 with or without the first Met residue.

III Agents

Agents of the invention include ND2 peptides including, overlapping, consisting of, or within residues 289-321, and preferably including, overlapping, consisting of, or within residues 307-321 or 310-321 of the ND2 protein (SEQ ID NO:60). An ND2 peptide usually has at least three contiguous residues within residues 289-321 of ND2. An ND2 peptide preferably binds to a Src protein within the unique domain at a site approximately including or within amino acids 40-49 of Src and competitively inhibits interactions with ND2 protein and Src protein. ND2 peptides typically have up to 10, 11, 12, 15, 20, 30 or 40 residues of SEQ ID NO:60 meaning that the designated number of residues in the ND2 peptide are identical to corresponding residues in the full length ND2 sequence when maximally aligned with it. Preferably at least 3, 4, 5, 6, 7, 8, 9, 10, 11, 12, 13, 14 or 15 of these residues are contiguous residues within residues 289-321, and preferably within residues 307-321 or 310-321 of ND2. Preferably peptides have 4-20, 5-20, 6-20, 7-20, or 8-20 amino acids identical to corresponding residues from the ND2 sequence when maximally aligned with it, and more preferably 4-12, 7-12, 7-17, 8-16, 12-15 or 5-10 such residues. Some ND2 peptides have an amino acid sequence consisting of 4-20, 7-12, 7-15 or 12-15 contiguous residues between amino acids 289 and 321 of SEQ ID NO:60. Some ND2 peptides have an amino acid sequence consisting of 3-12, 6-12, 7-12, 10-12, 10-15, 12-15, or 7-15 contiguous residues between amino acids 307-321 or 310-321 of SEQ ID NO:60. Some ND2 peptides consist of a segment of ND2 beginning at a residue between positions 300 and 312 and ending at a residue between positions 317 and 325 and being at least 6, 7, 8, 9, 10, 11, 12, 13, 14 or 15 amino acids long. Some ND2 peptides consist of a segment beginning between residues 305 and 310 and ending between residues 318 and 323. Some ND2 peptides have a segment beginning between residues 307 and 310 and ending at residue 321. Some ND2 peptide have an amino acid sequence consisting of at least 3, 4, 5, 6, 7, 8, 9, 10, 11, 12, 13, or 14 residues with amino acids 307-321 or 310-321 of SEQ ID NO:60. Some ND2 peptides consist of residues 304-321, 305-321, 306-321, 307-321, 308-321, 309-321, 310-321, or 311-321, 312-321 of SEQ ID NO:60. The optimal length of peptide can vary slightly depending on the indication and/or whether the peptide is used with lipidation or an internalization peptide.

Flanking amino acids unrelated to SEQ ID NO:60 can be linked to an ND2 peptide, for examples, an internalization peptide, as discussed below, to facility membrane crossing, as can a tag, such as biotin or GST, to assist in purification, identification or screening. Except for unrelated flanking sequence of amino acids, any amino acids within an ND2 peptide differing from SEQ ID NO:60, is preferably a conservative substitution relative to the corresponding residue in SEQ ID NO:60. ND2 peptides having a sequence differing from SEQ ID NO:60 (not including unrelated flanking sequences) preferably have no more than 6, 5, 4, 3, 2 or 1 deletions, insertions or substitutions relative to SEQ ID NO:60 or any specified segment thereof, such as residues 307-321 or 310-321 of SEQ ID NO:60. Insertions with respect to a specified segment of SEQ ID NO:60, such as 307-321 or 310-321 may include, additional flanking residues from SEQ ID NO:60. Thus, for example, a peptide described as consisting of 310-321 with up to six deletions, insertions or substitutions can include a peptide consisting of residues 307-321 (i.e., having three inserted amino acids from SEQ ID NO:60 at the N-terminus). ND2 peptides preferably have no more than 40, 30, 20, 15, or 12 amino acids in total (not including unrelated flanking sequences, such as an internalization peptide).

Agents of the invention also include peptidomimetics of ND2 peptides. A peptidomimetic is a synthetic chemical compound which has substantially the same structural and/or functional characteristics of as an ND2 peptide consisting of natural amino acids but has at least one non-peptide bond or at least one non-natural amino acid.

The peptidomimetic can contain entirely synthetic, non-natural analogues of amino acids, or can be a chimeric molecule of partly natural peptide amino acids and partly non-natural analogs of amino acids. A peptidomimetic can also incorporate any amount of natural amino acid conservative substitutions as long as such substitutions also do not substantially alter the mimetic's structure and/or inhibitory or binding activity. In a peptidomimetic of a chimeric peptide comprising an ND2 peptide and an internalization peptide, either the active moiety or the internalization moiety or both can be a peptidomimetic.

Peptides and peptidomimetics of the invention can contain modified amino acid residues for example, residues that are N-alkylated. N-terminal alkyl modifications can include e.g., N-Methyl, N-Ethyl, N-Propyl, N-Butyl, N-Cyclohexylmethyl, N-Cyclyhexylethyl, N-Benzyl, N-Phenylethyl, N-phenylpropyl, N-(3, 4-Dichlorophenyl)propyl, N-(3,4-Difluorophenyl)propyl, and N-(Naphthalene-2-yl)ethyl). Peptides or peptidomimetics can also be acetylated, phosphorylated and/or glycosylated.

In some peptidomimetics, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R- or S-form. Thus, a peptidomimetic may include 1, 2, 3, 4, 5, at least 50%, or all D-amino acid resides. A peptidomimetic containing some or all D residues is sometimes referred to an "inverso" peptide.

Peptidomimetics also include retro peptides. A retro peptide has a reverse amino acid sequence. Peptidomimetics also include retro inverso peptides in which the order of amino acids is reversed from so the originally C-terminal amino acid appears at the N-terminus and D-amino acids are used in place of L-amino acids.

Individual peptidomimetic residues can be joined by peptide bonds, other chemical bonds or coupling means, such as, e.g., glutaraldehyde, N-hydroxysuccinimide esters, bifunctional maleimides, N,N-dicyclohexylcarbodiimide (DCC) or N,N-diisopropylcarbodiimide (DIC). Linking groups that can be an alternative to the traditional amide bond ("peptide bond") linkages include, e.g., ketomethylene (e.g., —C(C=O)—CH2— for —C(=O)—NH—), aminomethylene (CH2-NH), ethylene, olefin (CH=CH), ether (CH2-O), thioether (CH2-S), tetrazole (CN4-), thiazole, retroamide, thioamide, or ester (see, e.g., Spatola (1983) in Chemistry and Biochemistry of Amino Acids, Peptides and Proteins, Vol. 7, pp 267-357, A Peptide Backbone Modifications, Marcell Dekker, NY).

Mimetics of aromatic amino acids can be generated by replacing with e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxybiphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R—N=C=N—R=) such as, e.g., 1-cyclohexyl-3(2-morpholinyl-(4-ethyl) carbodiimide or 1-ethyl-3(4-azonia-4, 4-dimetholpentyl) carbodiimide Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions.

Tyrosine residue mimetics can be generated by reacting tyrosyl with, e.g., aromatic diazonium compounds or tetranitromethane. N-acetylimidizol and tetranitromethane can be used to form 0-acetyl tyrosyl species and 3-nitro derivatives, respectively.

Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole.

Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide.

Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A linker, e.g., a polyethylene glycol linker, can be used to dimerize an ND2 peptide or peptidomimetic thereof to enhance its affinity and selectivity towards Src. Optionally, about 2-10 copies of a PEG can be joined in tandem as a linker.

Appropriate pharmacological activity of peptides, peptidomimetics or other agent can be confirmed, if desired, by showing inhibition of Src-ND2 interaction in vitro or in an animal model as described below. Useful peptides or peptidomimetics typically have IC50 values of less than 50 µM, 25 µM, 10 µM, 0.1 µM or 0.01 µM in such an assay. Preferred peptides typically have an IC50 value of between 0.001-1 µM, and more preferably 0.05-0.5 or 0.05 to 0.1 µM.

IV. Internalization Peptides and Lipidation

Internalization peptides, also known as cell membrane transduction peptides or cell penetrating peptides, are a well-known class of relatively short (e.g., 5-30 or 7-20 or 9-15 amino acids) peptides that allow many cellular or viral proteins to traverse membranes. Such peptides typically have a cationic charge from an above normal representation (relative to proteins in general) of arginine and/or lysine residues that is believed to facilitate their passage across membranes. Some such peptides have at least 5, 6, 7 or 8 arginine and/or lysine residues. Examples include the antennapedia protein (Bonfanti, Cancer Res. 57, 1442-6 (1997)) (and variants thereof), the Tat protein of human immunodeficiency virus, the protein VP22, the product of the UL49 gene of herpes simplex virus type 1, Penetratin, SynB1 and 3, Transportan, Amphipathic, gp41NLS, polyArg, and several plant and bacterial protein toxins, such as ricin, abrin, modeccin, diphtheria toxin, cholera toxin, anthrax toxin, heat labile toxins, and *Pseudomonas aeruginosa* exotoxin A (ETA). Other examples are described in the following references (Temsamani, Drug Discovery Today, 9(23):1012-1019, 2004; De Coupade, Biochem J., 390:407-418, 2005; Saalik, Bioconjugate Chem. 15: 1246-1253, 2004; Zhao, Medicinal Research Reviews 24(1): 1-12, 2004; Deshayes, Cellular and Molecular Life Sciences 62:1839-49, 2005) (all incorporated by reference).

A preferred internalization peptide is Tat from the HIV virus. A Tat peptide reported in previous work comprises or consists of the standard amino acid sequence YGRKKRRQRRR (SEQ ID NO:2) found in HIV Tat protein. SEQ ID NO:2 is designated as the standard Tat peptide. If additional residues flanking such a Tat motif are present (beside the pharmacological agent) the residues can be for example natural amino acids flanking this segment from a Tat protein, spacer or linker amino acids of a kind typically used to join two peptide domains, e.g., gly (ser)4 (SEQ ID NO:44), TGEKP (SEQ ID NO:45), GGRRGGGS (SEQ ID NO:46), or LRQRDGERP (SEQ ID NO:47) (see, e.g., Tang et al. (1996), J. Biol. Chem. 271, 15682-15686; Hennecke et al. (1998), Protein Eng. 11, 405-410)), or can be any other amino acids that do not significantly reduce capacity to confer uptake of the variant without the flanking residues. Preferably, the number of flanking amino acids other than an active peptide does not exceed ten on either side of YGRKKRRQRRR (SEQ ID NO:2). One suitable Tat peptide comprising additional amino acid residues flanking the C-terminus of YGRKKRRQRRR (SEQ ID NO:2) is YGRKKRRQRRRPQ (SEQ ID NO:48). However, preferably, no flanking amino acids are present.

Variants of the above Tat peptide having reduced capacity to bind to N-type calcium channels are described by WO/2008/109010. Such variants can comprise or consist of an amino acid sequence XGRKKRRQRRR (SEQ ID NO:49), in which X is an amino acid other than Y or nothing (in which case G is a free N-terminal residue). A preferred Tat peptide has the N-terminal Y residue substituted with F. Thus, a tat peptide comprising or consisting of FGRKKRRQRRR (SEQ ID NO:3) is preferred. Another preferred variant tat peptide consists of GRKKRRQRRR (SEQ ID NO:1). Other tat peptides that can be used include GRKKRRQRRRPQ (SEQ ID NO:4) and GRKKRRQRRRP (SEQ ID NO:59). Other Tat peptides comprise at least eight contiguous amino acids of the sequence GRKKRRQRRR (SEQ ID NO:1). Other tat peptides that facilitate uptake of an agent without inhibiting N-type calcium channels include those presented above. Another preferred Tat peptide is referred to as rv-Tat or RRRQRRKKRGY (SEQ ID NO:58).

```
X-FGRKKRRQRRR (F-Tat)    (SEQ ID NO: 61)
X-GKKKKKQKKK             (SEQ ID NO: 34)
X-RKKRRQRRR              (SEQ ID NO: 35)
X-GAKKRRQRRR             (SEQ ID NO: 36)
X-AKKRRQRRR              (SEQ ID NO: 37)
X-GRKARRQRRR             (SEQ ID NO: 38)
X-RKARRQRRR              (SEQ ID NO: 39)
X-GRKKARQRRR             (SEQ ID NO: 40)
X-RKKARQRRR              (SEQ ID NO: 41)
X-GRKKRRQARR             (SEQ ID NO: 42)
X-RKKRRQARR              (SEQ ID NO: 43)
X-GRKKRRQRAR             (SEQ ID NO: 50)
X-RKKRRQRAR              (SEQ ID NO: 51)
X-RRPRRPRRPRR            (SEQ ID NO: 52)
X-RRARRARRARR            (SEQ ID NO: 53)
X-RRRARRRARR             (SEQ ID NO: 54)
X-RRRPRRRPRR             (SEQ ID NO: 55)
X-RRPRRPRR               (SEQ ID NO: 56)
X-RRARRARR               (SEQ ID NO: 57)
```

X can represent a free amino terminus, one or more amino acids, or a conjugated moiety. Internalization peptides can be used in inverso or retro or inverso retro form with or without the linked peptide or peptidomimetic being in such form.

Internalization peptides can be attached to agents by conventional methods. For example, the agents can be joined to internalization peptides by chemical linkage, for instance via a coupling or conjugating agent. Numerous such agents are commercially available and are reviewed by Wong, Chemistry of Protein Conjugation and Cross-Linking, CRC Press (1991). Some examples of cross-linking reagents include J-succinimidyl 3-(2-pyridyldithio) propionate (SPDP) or N,N'-(1,3-phenylene)bismaleimide; N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents include p,p'-difluoro-m, m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

For agents that are peptides attachment to an internalization peptide can be achieved by generating a fusion protein comprising the peptide sequence fused, preferably at its N-terminus, to an internalization peptide.

Peptides, optionally fused to Tat peptides, can be synthesized by solid phase synthesis or recombinant methods. Peptidomimetics can be synthesized using a variety of procedures and methodologies described in the scientific and patent literature, e.g., Organic Syntheses Collective Volumes, Gilman et al. (Eds.) John Wiley & Sons, Inc., NY, al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; Ostresh (1996) *Methods Enzymol.* 267:220-234. Peptides or peptidomimetics linked to internalization peptides as fusion peptides or otherwise preferable include no more than 50 amino acids total, and more preferably no more than 25 or 20 amino acids.

Instead of or as well as linking an ND2 peptide to an internalization peptide, an ND2 peptide can be linked to a lipid (lipidation) to increase hydrophobicity of the conjugate relative to the peptide alone and thereby facilitate passage of the linked ND2 peptide across cell membranes and/or across the brain barrier. Lipidation is preferably performed on the N-terminal or C-terminal amino acid but can also be performed on internal amino acids, provided the association constant of the ND2 peptide for Src is not reduced by more than 50%. Lipids are organic molecules more soluble in ether than water and include fatty acids, glycerides and sterols. Suitable forms of lipidation include myristoylation, palmitoylation or attachment of other fatty acids preferably with a chain length of 10-20 carbons, such as lauric acid and stearic acid, as well as geranylation, geranylgeranylation, and isoprenylation. Lipidations of a type occurring in posttranslational modification of natural proteins are preferred. Lipidation with a fatty acid via formation of an amide bond to the alpha-amino group of the N-terminal amino acid of the peptide is also preferred. Lipidation can be by peptide synthesis including a prelipidated amino acid, be performed enzymatically in vitro or by recombinant expression, by chemical crosslinking or chemical derivatization of the peptide Amino acids modified by myristoylation and other lipid modifications are commercially available.

Lipidation preferably facilitates passage of a linked ND2 peptide across a cell membrane and/or the blood brain barrier without causing a transient reduction of blood pressure as has been found when a standard Tat peptide is administered at high dosage (e.g., at or greater than 3 mg/kg), or at least with smaller reduction that than the same ND2 peptide linked to a standard Tat peptide.

If a transient reduction of blood pressure occurs when administering an ND2 peptide (e.g., when linked to a standard Tat peptide and administered at high dosage), it can mitigated by co-administration of an anti-inflammatory, preferably a mast cell degranulation inhibitor (see, e.g., WO/2009/07610)).

V. Patients Amenable to Treatment or Prophylaxis

Agents of the present invention are useful in treating or effecting prophylaxis of neurological disease or disorders, pain and cancer. These classes are not of course mutually exclusive. For example, a brain cancer could fall under all three classes.

A variety of neurological diseases and disorders are amenable to treatment or prophylaxis. Such diseases and disorders include anxiety, epilepsy, optical or retinal neuropathies, stroke (e.g., spontaneous, acute ischemic, hemorrhagic, procedurally induced), epilepsy, hypoxia, traumatic injury to the CNS not associated with stroke such as, neurotrauma, traumatic brain injury and spinal cord injury, Alzheimer's disease, Parkinson's disease, other dementias associated with Lewy bodies, Huntington's disease, ALS, bovine spongiform encephalopathy, Creutzfeldt-Jakob disease, multiple sclerosis, spinal cord degeneration, spinocerebella ataxia, Tay-Sachs disease, and transmissible spongiform encephalopathy. Such disorders also include patients undergoing surgery that affects or may affect a vessel (e.g., jugular vein or carotid artery) supplying or removing blood to or from the brain, particularly patients undergoing neurosurgery, such as endovascular surgery to repair an aneurysm or endovascular surgery to a blood vessel supplying a limb, spinal cord, retina or kidney. Such repair can be effected for example by inserting a stent or coil into the blood vessel subject to the aneurysm Neurological diseases and disorders associated at least in part with excitotoxicity are particularly amenable to treatment by the method of the invention.

A stroke is a condition resulting from impaired blood flow in the CNS regardless of cause. Potential causes include embolism, hemorrhage, thrombosis and surgery. Some neuronal cells die immediately as a result of impaired blood flow. These cells release their component molecules including glutamate, which in turn activates NMDA receptors, which raise intracellular calcium levels, and intracellular enzyme levels leading to further neuronal cell death (the excitotoxicity cascade). The death of tissue from lack of oxygen is referred to as infarction. Infarction Volume (i.e., the volume of dead neuronal cells resulting from stroke in the brain) can be used as an indicator of the extent of pathological damage resulting from stroke. The symptomatic effect depends both on the volume of an infarction and where in the brain it is located. Disability index can be used as a measure of symptomatic damage, such as the Rankin Stroke Outcome Scale (Rankin, Scott Med J; 2:200-15 (1957)), the NIH stroke scale and the Barthel Index. The Rankin Scale is based on assessing directly the global conditions of a patient as follows.

0 No symptoms at all
1 No significant disability despite symptoms; able to carry out all usual duties and activities.
2 Slight disability; unable to carry out all previous activities but able to look after own affairs without assistance.
3 Moderate disability requiring some help, but able to walk without assistance
4 Moderate to severe disability; unable to walk without assistance and unable to attend to own bodily needs without assistance.
5 Severe disability; bedridden, incontinent, and requiring constant nursing care and attention.

The Barthel Index is based on a series of questions about the patient's ability to carry out 10 basic activities of daily living resulting in a score between 0 and 100, a lower score indicating more disability (Mahoney et al., Maryland State Medical Journal 14:56-61 (1965)).

Alternatively stroke severity/outcomes can be measured using the NIH stroke scale, available at world wide web ninds nih gov/doctors/NIH_Stroke_Scale_Booklet.pdf.

The scale is based on the ability of a patient to carry out 11 groups of functions that include assessments of the patient's level of consciousness, motor, sensory and language functions.

An ischemic stroke refers more specifically to a type of stroke that caused by blockage of blood flow to the brain. The underlying condition for this type of blockage is most commonly the development of fatty deposits lining the vessel walls. This condition is called atherosclerosis. These fatty deposits can cause two types of obstruction. Cerebral thrombosis refers to a thrombus (blood clot) that develops at the clogged part of the vessel "Cerebral embolism" refers generally to a blood clot that forms at another location in the circulatory system, usually the heart and large arteries of the upper chest and neck. A portion of the blood clot then breaks loose, enters the bloodstream and travels through the brain's blood vessels until it reaches vessels too small to let it pass. A second important cause of embolism is an irregular heartbeat, known as arterial fibrillation. It creates conditions in which clots can form in the heart, dislodge and travel to the brain. Additional potential causes of ischemic stroke are hemorrhage, thrombosis, dissection of an artery or vein, a cardiac arrest, shock of any cause including hemorrhage, and iatrogenic causes such as direct surgical injury to brain blood vessels or vessels leading to the brain or cardiac or pulmonary surgery. Ischemic stroke accounts for about 83 percent of all cases of stroke.

Transient ischemic attacks (TIAs) are minor or warning strokes. In a TIA, conditions indicative of an ischemic stroke are present and the typical stroke warning signs develop. However, the obstruction (blood clot) occurs for a short time and tends to resolve itself through normal mechanisms. Patients undergoing heart, pulmonary or neuro-surgery are at particular risk of transient cerebral ischemic attack.

Hemorrhagic stroke accounts for about 17 percent of stroke cases. It results from a weakened vessel that ruptures and bleeds into the surrounding brain. The blood accumulates and compresses the surrounding brain tissue. The two general types of hemorrhagic strokes are intracerebral hemorrhage and subarachnoid hemorrhage. Hemorrhagic stroke result from rupture of a weakened blood vessel. Potential causes of rupture from a weakened blood vessel include a hypertensive hemorrhage, in which high blood pressure causes a rupture of a blood vessel, or another underlying cause of weakened blood vessels such as a ruptured brain vascular malformation including a brain aneurysm, arteriovenous malformation (AVM) or cavernous malformation. Hemorrhagic strokes can also arise from a hemorrhagic transformation of an ischemic stroke which weakens the blood vessels in the infarct, or a hemorrhage from primary or metastatic tumors in the CNS which contain abnormally weak blood vessels. Hemorrhagic stroke can also arise from iatrogenic causes such as direct surgical injury to a brain blood vessel. An aneurysm is a ballooning of a weakened region of a blood vessel. If left untreated, the aneurysm continues to weaken until it ruptures and bleeds into the brain. An arteriovenous malformation (AVM) is a cluster of abnormally formed blood vessels. A cavernous malformation is a venous abnormality that can cause a hemorrhage from weakened venous structures. Any one of these vessels can rupture, also causing bleeding into the brain. Hemorrhagic stroke can also result from physical trauma. Hemorrhagic stroke in one part of the brain can lead to ischemic stroke in another through shortage of blood lost in the hemorrhagic stroke.

The present agents are also useful for treatment or prophylaxis of pain. Pain is an experiential phenomenon that is subjective to the individual experiencing it, and is influenced by the individual's mental state, including environment and cultural background. "Physical" pain can sometimes be linked to a stimulus perceivable to a third party that is causative of actual or potential tissue damage. In this sense, pain can be regarded as a "sensory and emotional experience associated with actual or potential tissue damage, or described in terms of such damage," according to the International Association for the Study of Pain (IASP). However, some instances of pain have no perceivable cause. For example, psychogenic pain, including exacerbation of a pre-existing physical pain by psychogenic factors or syndromes of a sometimes persistent, perceived pain in persons with psychological disorders without any evidence of a perceivable cause of pain.

Pain is generally divided into three main categories: physiological, inflammatory and neuropathic. However, multiple mechanisms contribute to each of these, with some overlap, as each is subject to or an expression of neural plasticity. Neural plasticity is generally divided into activation, modulation and modification, and each can contribute to a change in the threshold of sensitivity such that hypersensitivity to pain stimuli results. Pain is not a passive consequence of transfer of a defined peripheral input into a pain center in the cortex, but rather an active process generated partly in the periphery and partly in the central nervous system by changes in plasticity.

Physiological pain is initiated as a reaction to noxious stimuli (needle prick, temperature extremes, chemicals), inflammatory pain is initiated by tissue damage/inflammation and neuropathic pain by nervous system lesions. Each is characterized by hypersensitivity at the site of the damage and in adjacent normal tissues. In such cases, stimuli that would not normally produce pain do so (allodynia) and noxious stimuli (sharp objects, heat, chemical) evoke greater and more prolonged pain (hyperalgesia). Inflammatory and physiological pain hypersensitivity generally returns to normal once the disease process or pathology returns to normal. Neuropathic pain will persist after the initiating event has healed and is a result of abnormal nervous system functions rather than a reaction to the pathology.

Pain can also be referred to as acute or chronic. Acute pain is a sharp pain that is transient in nature, such as that caused by a pin prick. Chronic pain is pain or pain sensitivity that persists for a longer period, usually a day or more. Rodent models of chronic pain can include formalin footpad injection, Complete Freund's Adjuvant footpad injection, nerve constriction models (spinal/sciatic), and all neuropathic pain models.

Pain includes nociceptive pain (including somatic and visceral), neuropathic/neurogenic pain (degenerative, pressure induced, inflammatory, infection-induced, among others), sympathic pain inflammatory pain, ischemic pain and pain breakthrough pain, allodynia, hyperalgesia, hyperesthesia, dysesthesia, paresthesia, hyperpathia, phantom limb pain, psychogenic pain, anesthesia dolorosa, neuralgia, neuritis, malignant pain, anginal pain, and/or idiopathic pain, and complex regional pain syndromes I, II complex regional pain syndrome II. These terms are defined by the International Association for the Study of Pain and are not mutually exclusive.

Nociceptive pain is initiated by specialized sensory nociceptors in the peripheral nerves in response to noxious stimuli, encoding noxious stimuli into action potentials. Nociceptors, generally on A-δ and C fibers, are free nerve endings that terminate just below the skin, in tendons, joints, and in body organs. The dorsal root ganglion (DRG) neurons provide a site of communication between the periphery and the spinal cord. The signal is processed through the spinal cord to the brainstem and thalamic sites and finally to the cerebral cortex, where it usually (but not always) elicits a sensation of pain. Nociceptive pain can result from a wide variety of a chemical, thermal, biological (e.g., inflammatory) or mechanical events that have the potential to irritate or damage body tissue, which are generally above a certain minimal threshold of intensity required to cause nociceptive activity in nociceptors.

Inflammatory pain refers to pain associated with inflammation. Inflammation is an immune response of an organism to infection, irritation and/or injury. Inflammation is characterized by redness, swelling, and warmth. A pain-causing stimulus often evokes an inflammatory response which itself can contribute to an experience of pain.

Neuropathic pain is generally the result of abnormal functioning in the peripheral or central nervous system, giving rise to peripheral or central neuropathic pain, respectively. Neuropathic pain is defined by the International Association for the Study of Pain as pain initiated or caused by a primary lesion or dysfunction in the nervous system. Neuropathic pain often involves actual damage to the nervous system, especially in chronic cases. Inflammatory nociceptive pain is generally a result of tissue damage and the resulting inflammatory process. Neuropathic pain can persist well after (e.g., months or years) beyond the apparent healing of any observable damage to tissues.

In neuropathic pain, sensory processing from an affected region can become abnormal and innocuous stimuli (e.g., thermal, touch/pressure) that would normally not cause pain may do so (i.e., allodynia) or noxious stimuli may elicit exaggerated perceptions of pain (i.e., hyperalgesia) in response to a normally painful stimulus. In addition, sensations similar to electric tingling or shocks or "pins and needles" (i.e., paresthesias) and/or sensations having unpleasant qualities (i.e., dysesthesias) may be elicited by normal stimuli. Breakthrough pain is an aggravation of pre-existing chronic pain. Hyperpathia is a painful syndrome resulting from an abnormally painful reaction to a stimulus. The stimulus in most of the cases is repetitive with an increased pain threshold, which can be regarded as the least experience of pain which a patient can recognize as pain.

Examples of neuropathic pain include tactile allodynia (e.g., induced after nerve injury) neuralgia (e.g., post herpetic (or post-shingles) neuralgia, trigeminal neuralgia), reflex sympathetic dystrophy/causalgia (nerve trauma), components of cancer pain (e.g., pain due to the cancer itself or associated conditions such as inflammation, or due to treatment such as chemotherapy, surgery or radiotherapy), phantom limb pain, entrapment neuropathy (e.g., carpal tunnel syndrome), and neuropathies such as peripheral neuropathy (e.g., due to diabetes, HIV, chronic alcohol use, exposure to other toxins (including many chemotherapies), vitamin deficiencies, and a large variety of other medical conditions). Neuropathic pain includes pain induced by expression of pathological operation of the nervous system following nerve injury due to various causes, for example, surgical operation, wound, shingles, diabetic neuropathy, amputation of legs or arms, cancer, and the like. Medical conditions associated with neuropathic pain include traumatic nerve injury, stroke, multiple sclerosis, syringomyelia, spinal cord injury, and cancer.

In some conditions, pain appears to be caused by a complex mixture of nociceptive and neuropathic factors. For example, chronic pain often comprises inflammatory nociceptive pain or neuropathic pain, or a mixture of both. An initial nervous system dysfunction or injury may trigger the neural release of inflammatory mediators and subsequent neuropathic inflammation. For example, migraine headaches can represent a mixture of neuropathic and nociceptive pain. Also, myofascial pain is probably secondary to nociceptive input from the muscles, but the abnormal muscle activity may be the result of neuropathic conditions.

Symptoms of pain experienced by a patient may or may not be accompanied by signs of pain discernible to a clinician. Conversely, pain can be manifested by clinical signs without the patient being aware of symptoms. Symptoms of pain can include a response to pain, e.g., in the form of a behavioral change. Exemplary responses to pain can include conscious avoidance of a painful stimulus, a protective response intended to protect the body or body parts from the painful stimulus, responses intended to minimize pain and promote healing, communication of pain, and physiological responses. Communicative responses can involve vocalizations of pain or modifications of facial expression or posture. Physiological responses include responses mediated by the autonomic nervous system or endocrine system. e.g., enhanced release of adrenalin and noradrenalin, increased output of glucagon and/or hormones and/or corticosteroids. Physiological changes that can be monitored include locomotor effects such as twitching, convulsions, paralysis, dilated pupils, shivering, hyperesthesia and/or altered reflexes. Physiological cardiovascular responses to pain can include changes in blood pressure, alterations in pulse rate and quality, decreased peripheral circulation, cyanosis and congestion. Increased muscle tension (tone) is also symptomatic of pain. Changes in brain function in response to pain can be monitored by various techniques such as electroencephalography (EEG), frontal electromyography (FEMG) or positron emission tomography (PET).

Another symptom of pain can be referred pain, which is a perception of pain as being localized at a site adjacent to or at a distance from the actual site of the pain-causing stimulus. Often referred pain arises when a nerve is compressed or damaged at or near its origin. In this circumstance, the sensation of pain will generally be felt in the territory that the nerve serves, even though the damage originates elsewhere. A common example occurs in intervertebral disc herniation, in which a nerve root arising from the spinal cord is compressed by adjacent disc material. Although pain may arise from the damaged disc itself, pain will also be felt in the region served by the compressed nerve (for example, the thigh, knee, or foot).

Nociceptive activity is a symptom of nociceptive pain. Nociceptive activity, even in the absence of consciously-perceived pain, may trigger withdrawal reflexes and a variety of autonomic responses such as pallor, diaphoresis, bradycardia, hypotension, lightheadedness, nausea and fainting.

The agents of the invention are also useful for treating or effecting prophylaxis of cancer. Src is an oncogene present in the human body, and many cancers are associated with its overexpression, mutation or activity. Those include solid tumors, such as breast, colon, lung, prostate, pancreatic, head and neck, among others. Src can also become abnormally active due to mutations in other proteins that regulate it. The present methods are particularly useful for cancer types associated with elevated expression of Src at the mRNA or protein level, and particularly cancers in which Src expression is elevated relative to tissue-matched noncancerous tissues in the same patient. In some methods, expression of Src in a cancer is checked, optionally in comparison with expression of a tissue matched noncancerous sample from the same patient. However, checking the expression level is not required. Detectable activity of Src kinase and particularly elevated activity relative to a tissue matched noncancerous control sample provide an indication that cancer is amenable to treatment with the methods of the invention. Increased copy number of the Src gene in a cancer cell can provide an alternative or additional indication that a cancer is amenable to treatment. Increased copy number can be detected using for example, Southern blotting, quantitative PCR, fluorescence in situ hybridization of metaphase chromosome spreads, and other cytogenetic techniques. Presence of mutations in Src associated with oncogenicity is also an indicator a cancer is treatable by methods of the invention.

IX. Methods of Treatment/Prophylaxis a) Methods of Treatment

Agents optionally attached to internalization peptides (or optionally lapidated) are administered to a patient having sign(s) and/or symptom(s) of a disease or disorder described above in a therapeutically effective regime. Such a regime means an amount, frequency and route of administration effective to cure, reduce or inhibit further deterioration of at least one sign or symptom of a disease in a population of patients (or animal models) suffering from the disease or condition being treated relative to a control population of patients (or animal models) suffering from that disease or condition who are not treated with an agent of the invention. The regime is also considered therapeutically effective if an individual treated patient achieves an outcome more favorable than the mean outcome in a control population of comparable patients not treated by methods of the invention. The number of doses depends on the disease or disorder being treated. For acute or episodic conditions, such as stroke, traumatic injury, anxiety, acute pain, or epilepsy a single dose is often sufficient at least per episode of disease. For chronic conditions, such as neurogenerative diseases, for example, Alzheimer's or Parkinson's, cancer, or chronic pain, multiple doses, and sometimes life-long treatment are indicated.

For a patient suffering from stroke or other ischemic condition of the CNS, an agent is administered in a regime comprising an amount frequency and route of administration effective to reduce the damaging effects of stroke or other ischemic condition. When the condition requiring treatment is stroke, the outcome can be determined by infarction volume or disability index, and a dosage is considered therapeutically effective if an individual treated patient shows a disability of two or less on the Rankin scale and 75 or more on the Barthel scale, or if a population of treated patients shows a significantly improved (i.e., less disability) distribution of scores on a disability scale than a comparable untreated population, see Lees et al., N Engl J Med 2006; 354:588-600. A single dose of an agent is often sufficient for treatment of stroke.

Agents of the invention are also useful to extend the efficacy or safety windows of reperfusion, or improve the safety or efficacy of reperfusion at a given time. This is especially useful in treatment of ischemic stroke in conjunction with another agent that breaks down clots such as tissue plasminogen activator, where the useful window for administration is only 0-4.5 hours after the stroke due to an increase in frequency of hemorrhagic events with time. Agent of the invention can be administered to improve the safety and/or efficacy of agents which break down clots in the brain.

Usually between 1 and 8 doses of an agent are administered to treat cancer, but more doses can be given. An agent can be administered daily, biweekly, weekly, every other week, monthly or at some other interval, depending, e.g. on the half-life of the agent for 1 week, 2 weeks, 4 weeks, 8 weeks, 3-6 months or longer. Repeated courses of treatment are also possible, as is chronic administration.

Treatment of a cancer with an agent can be combined with conventional treatments, for example Taxol (paclitaxel) or its derivatives, platinum compounds such as carboplatin or cisplatin, anthrocyclines such as doxorubicin, alkylating agents such as cyclophosphamide, anti-metabolites such as 5-fluorouracil, or etoposide. An agent of the invention can be administered in combination with two, three or more of these agents in a standard chemotherapeutic regimen, for example, taxol and carboplatin, e.g. for breast and ovarian cancer. Other agents for combination include biologics such as monoclonal antibodies, including Herceptin™ against the HER2 antigen, Avastin™ against VEGF, or antibodies to the EGF receptor, as well as small molecule anti-angiogenic or EGF receptor antagonist drugs. In addition, agents can be used together with radiation therapy or surgery.

Treatment with an agent of the invention can increase the median progression-free survival or overall survival time of patients with a cancer by at least 30% or 40% but preferably 50%, 60% to 70% or even 100% or longer, compared to an otherwise comparable regime but without the agent. In addition or alternatively, treatment including the agent may increase the complete response rate, partial response rate, or objective response rate (complete+partial) of patients with a cancer especially when relapsed or refractory by at least 30% or 40% but preferably 50%, 60% to 70% or even 100% compared to the same regime without the synbody. Optionally, treatment can inhibit tumor growth, invasion, metastasis or angiogenesis.

Typically, in a clinical trial (e.g., a phase II, phase II/III or phase III trial), the increases in median progression-free survival and/or response rate of the patients treated with chemotherapy plus an agent of the invention relative to the control group of patients receiving chemotherapy alone (or plus placebo) is statistically significant, at the p=0.05 or 0.01 level. The complete and partial response rates are determined by objective criteria commonly used in clinical trials for cancer, e.g., as listed or accepted by the National Cancer Institute and/or Food and Drug Administration.

The effects of agents on pain in humans can be evaluated using a variety of tests. Numerous pain questionnaires and scales have been designed to evaluate a patient's pain, using different methods. Pain may be evaluated as a single measure (intensity only) or using several measures (duration and intensity). Useful pain scales include: the Visual Analog Scale, McGill Pain Questionnaire, and the Descriptor Differential Scale (see J. Rheumatol. 9 (5): 768-9. PMID 6184474. Melzack. (1975) Pain 1 (3): 277-99, Gracely (1988), Pain 35 (3): 279-88).

A patient's sensitivity to pain (pain threshold) can also be measured using a dolorimeter, such as a sonic palpometer, a pressure-controlled palpometer, laser-based Dolorimeter Analgesia meter (IITC Life Sciences), Baseline Algorimeter (Kom Kare Company), Bjornstrom's algesimeter, which measures sensitivity of the skin to pain, or Boas' algesimeter which measures sensitivity over the epigastrium. Examples of drugs that can be co-administered for treatment of pain include NSAIDs, COX 2 inhibitors, COX-3 inhibitors, iNOS inhibitors, PAR2 receptor antagonists, neuroleptic agents, opioids, N-acetylcholine receptor agonists, glycine antagonists, vanilloid receptor antagonists, neurokinin antagonists calcitonin gene-related peptide antagonists and cyclooxygenase (COX)-inhibiting nitric oxide donators (CINOD)s. Other pain relieving drugs include codeine, vicodin, morphine, Demerol, Percocet, Darvon and Darvocet conotoxins and Symlin.

b) Methods of Prophylaxis

The invention also provides methods and compositions for the prophylaxis of a disorder in a subject at risk of that disorder. Usually such a subject has an increased risk of developing the disorder (e.g., a condition, illness, disorder or disease) relative to a control population. The control population for instance can comprise one or more individuals selected at random from the general population (e.g., matched by age, gender, race and/or ethnicity) who have not been diagnosed or have a family history of the disorder. A subject can be considered at risk for a disorder if a risk factor associated with that disorder is found to be associated with that subject. A risk factor can include any activity, trait, event or property associated with a given disorder, for example, through statistical or epidemiological studies on a population of subjects. A subject can thus be classified as being at risk for a disorder even if studies identifying the underlying risk factors did not include the subject specifically. For example, a subject undergoing heart surgery is at risk of stroke because the frequency of transient cerebral ischemic attack is increased in a population of subjects who have undergone heart surgery as compared to a population of subjects who have not.

Other common risk factors for stroke include age, family history, gender, prior incidence of stroke, transient ischemic attack or heart attack, high blood pressure, smoking, diabetes, carotid or other artery disease, atrial fibrillation, other heart diseases such as heart disease, heart failure, dilated cardiomyopathy, heart valve disease and/or congenital heart defects; high blood cholesterol, and diets high in saturated fat, trans fat or cholesterol.

Risk factors for cancer include genetic susceptibility to cancer, patients who have undergone exposure to carcinogenic agents, such as radiation or toxins, and patients who have undergone previous treatment for cancer and are at risk of recurrence.

Risk factors for pain include undergo surgery, exposure to combat or other danger, or suffering from diseases associated with severe or chronic pain, such as diabetes and cancer.

Agents optionally linked to an internalization peptide are administered to patients at risk of a disease but not yet having the disease in a prophylactically effective regime, meaning an amount, frequency and route sufficient to prevent, delay or inhibit development of at least one sign or symptom of the disease in a population of patients (or animal models) at risk of the disease relative treated with the agent compared to a control population of patients (or animal models) at risk of the disease not treated with a chimeric agent of the invention. The amount is also considered prophylactically effective if an individual treated patient achieves an outcome more favorable than the mean outcome in a control population of comparable patients not treated by methods of the invention. A prophylactically effective regime involves the administration of a prophylactically effective dose at a frequency and route of administration needed to achieve the intended purpose. For prophylaxis of stroke or other acute onset diseases and disorders in a patient at imminent risk (e.g., a patient undergoing heart surgery), a single dose of an agent is usually sufficient. For patients at longer term risk, e.g., risk of cancer following exposure to a carcinogen, multiple dosing may be indicated.

X. Pharmaceutical Compositions, Dosages, and Routes of Administration

The agents of the invention, optionally linked to internalization peptides, can be administered in the form of a pharmaceutical composition. Pharmaceutical compositions are typically manufactured under GMP conditions. Pharmaceutical compositions can be provided in unit dosage form (i.e., the dosage for a single administration). Pharmaceutical compositions can be manufactured by means of conventional mixing, dissolving, granulating, dragee-making, levigating, emulsifying, encapsulating, entrapping or lyophilizing processes. For example, lyophilized agents can be used in the formulations and compositions described below.

Pharmaceutical compositions can be formulated in conventional manner using one or more physiologically acceptable carriers, diluents, excipients or auxiliaries that facilitate processing of chimeric agents into preparations which can be used pharmaceutically. Proper formulation is dependent on the route of administration chosen.

Administration can be parenteral, intravenous, oral, subcutaneous, intra-arterial, intracranial, intrathecal, intraperitoneal, topical, intranasal, by inhalation, transdermal, e.g., via a patch, or intramuscular. Intravenous administration is preferred.

Pharmaceutical compositions for parenteral administration are preferably sterile and substantially isotonic. For injection, agents can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents.

Alternatively agents can be in powder form for constitution with a suitable vehicle, e.g., sterile pyrogen-free water, before use.

Agents of the invention can also be administered in conjunction with other agents that increase passage of the agents of the invention across the blood brain barrier, such as mannitol, Tween® or DMSO.

For transmucosal administration, penetrants appropriate to the barrier to be permeated are used in the formulation. This route of administration can be used to deliver the compounds to the nasal cavity or for sublingual administration.

For oral administration, agents can be formulated with pharmaceutically acceptable carriers as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as the cross-linked polyvinylpyrrolidone, agar, or alginic acid or a salt thereof such as sodium alginate. If desired, solid dosage forms can be sugar-coated or enteric-coated using standard techniques. For oral liquid preparations such as, for example, suspensions, elixirs and solutions, suitable carriers, excipients or diluents include water, glycols, oils, alcohols. Additionally, flavoring agents, preservatives, coloring agents and the like can be added.

In addition to the formulations described previously, the agents can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions can be used to deliver chimeric agents. Certain organic solvents such as dimethylsulfoxide also can be employed, although usually at the cost of greater toxicity. Additionally, the compounds can be delivered using a sustained-release system, such as semipermeable matrices of solid polymers containing the therapeutic agent.

Sustained-release capsules can, depending on their chemical nature, release the chimeric agents for a few weeks up to over 100 days. Depending on the chemical nature and the biological stability of the therapeutic reagent, additional strategies for protein stabilization can be employed.

Because the agents of the invention can contain charged side chains or termini, they can be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

The amount of agent to be administered depends on the patient being treated, the disease or disorder, whether the treatment is therapeutic or prophylactic in nature, on the patient's weight, the severity of the affliction, the manner of administration and the judgment of the prescribing physician. The treatment can be repeated intermittently while symptoms detectable or even when they are not detectable. The treatment can be provided alone or in combination with other drugs.

Effective dose of the present agents can provide benefit without causing substantial toxicity. Toxicity of the agents can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. Agents, e.g., peptides or peptidomimetics, exhibiting high therapeutic indices are preferred (see, e.g., Fingl et al., 1975, In: *The Pharmacological Basis of Therapeutics*, Ch. 1, p. 1).

Chimeric agents comprising an internalization peptide linked to an agent can be used at the same or lower dosage on a molar basis as the agent alone, and can be administered by the same route as the pharmacologic agent alone, and for treatment of the same disease(s) as the pharmacologic agent alone.

Suitable dosages for agents optionally linked to an internalization peptide are usually less than 25 mg/kg. Dosages sometimes range from 10-4 mg/kg to 25 mg/kg, for example, 0.1 or 0.5 mg/kg to 1, 50 or 10 mg/kg. Total dosages per patient can be calculated by multiplying the dose per kg body weight by the patient's weight in kg. For example, the total dose for a 75 kg patient can be calculated by multiplying the above doses by 75.

XII. Screening Methods

1. Agents to be Screened

Agents can initially be screened in vitro for a desired binding or inhibitory activity. Agents can include ND2 peptides or peptidomimetics thereof as described above. Agents to be screened can also be obtained from natural sources, such as, e.g., marine microorganisms, algae, plants, fungi, or from libraries of synthetic peptides or other compounds. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, W0 91/18980.

2. In Vitro Screens

Agents can initially be screened for a desired binding activity, for example, an ability to bind Src, or Src peptide including residues 40-49 of Src. Alternatively or additionally, an agent can be screened for ability to compete with ND2 or a ND2 peptide as described above (e.g., a peptide consisting of residues 310-321 of ND2) for ability to bind to Src or a peptide including residues 40-49 or 40-58 thereof. Binding can be assessed by ELISA, Fluorescence polarization, or Western blot among other methods. In some formats, one component of such a binding assay is immobilized. Several formats are possible as described in the Examples. The ability of an agent to bind Src and/or inhibit binding of ND2 or and ND2 peptide to Src is an indication the agent has pharmacological activity useful in treating neurological disease, pain or cancer. Agents can then be further screened in a variety of animal models as disclosed further below.

Agents can also be screened for inhibitory activity against Src kinase. Kits for performing a kinase assay are commercially available. Src, typically in recombinantly expressed form, is mixed with a peptide bearing a phosphorylatable residue and a tag permitting immobilization in the presence of ATP, and kinase buffer. The amount of phosphorylated peptide, which is indicative of kinase activity, can be detected using an antibody specific for the phosphorylated peptide. Such an assay is performed in the presence and absence of an agent under test to determine if the agent reduces phosphorylation and by implication Src activity.

3. Animal Models of Stroke

Agents can be tested in various animal models of stroke. In one such model, in adult male Sprague-Dawley rats subjected to transient middle cerebral artery occlusion (MCAO) for 90 minutes by the intraluminal suture method Animals are fasted overnight and injected with atropine sulfate (0.5 mg/kg IP). After 10 minutes anesthesia is induced. Rats are orally intubated, mechanically ventilated, and paralyzed with pancuronium bromide (0.6 mg/kg IV). Body temperature is maintained at 36.5-37.5° C., with a heating lamp. Polyethylene catheters in the femoral artery and vein are used to continuously record blood pressure and to sample blood for gas and pH measurements. Transient MCAO is achieved for 90 min by introducing a poly-L-lysine-coated 3-0 monofilament nylon suture (Harvard Apparatus) into the circle of Willis via the internal carotid artery, effectively occluding the middle cerebral artery. This produces an extensive infarction encompassing the cerebral cortex and basal ganglia Animals are treated with either an agent under test or a negative or positive control. Treatment can be either before or up to one hour after inducing ischemia. A negative control can be vehicle. A positive control can be the Tat-NR2B9c peptide, YGRKKRRQR-RRKLSSIESDV (SEQ ID NO:6), previously shown to be effective. After administering an agent to the animals, infarction volume and/or disability index are determined. Infarction volumes are usually determined 24 hr post treatment but can be determined at a later time such as 3,7, 14 or 60 days. Disability index can be monitored over time, e.g., at 2 hr post treatment, 24 hr post treatment, one week and one month post treatment. Agents showing a statistically significant reduction in infarction volume and/or disability index relative to control animals not treated with the agents are identified as having activity useful for practicing the methods of the invention.

Similar experiments can be performed in animal subject to permanent ischemia. Permanent ischemia of the middle cerebral artery pial vessel can be carried out as described by Forder et al., Am J Physiol Heart Circ Physiol 288:H1989-H1996 (2005). In brief, the right ECA is cannulated with PE 10 polyethylene tubing. The skull is exposed via a midline incision, and a 6- to 8-mm cranial window is made over the right somatosensory cortex (2 mm caudal and 5 mm lateral to bregma). The pial arteries are visualized by injecting small boluses (10-20 µL) of the vital dye patent blue violet (10 mMol/L; Sigma) in normal saline, into the ECA. The same three pial arteriolar MCA branches are electrically cauterized and dye injections are repeated to ensure the interruption of flow through the cauterized arterioles. The incision is then closed and the animal returned to its cage and allowed free access to food and water. This permanent ischemia model produces a highly reproducible small infarction limited to the cortex underlying the coagulated terminal pial arteries.

4. Animal Models of Pain

Nociceptive tests in mammals (e.g., rodents) for pain include the tail-flick (a spinally-mediated nociceptive reflex) test (D'Amour et al. (1941), J. Pharmacol. Exp. Ther. 72: 74-79), the hot-plate test, the Randall-Selitto test (Swingle et al. (1971), Proc. Soc. exp. Biol. Med. 137: 536-538) and the tail-pinch test. Such tests can be used to evaluate the nociceptive threshold to different kinds of noxious stimuli such as threshold to heat (the tail-flick test, the hot-plate test, the Hargreaves' test of paw withdrawal, and by brief immersion of the tail or hindpaw into hot water); or tactile threshold to punctuate stimuli e.g., by the Von Frey test for allodynia test, J Neurosci Methods. 1999 Mar. 1; 87(2):185-93. Dynamic allodynia can be assessed by lightly stroking the planter surface of the hind paw with a cotton bud, where dynamic allodynia is considered to be present if animals respond to the cotton stimulus within 8 sec of commencing stroking. Pain response to noxious chemical agents can be measured e.g., by monitoring abdominal writhing after intraperitoneal injection of dilute acetic acid, and the aversive drinking test by adding capsaicin to drinking water (which can be used to evaluate trigeminal nociception).

Tests for inflammatory pain and hypersensitivity include the formalin paw test (Tjolsen et al. (1992), Pain 51: 5-17), the complete Freund's Adjuvant paw test (CFA), the test for formalin-induced facial pain (Clavelou et al. (1989), Neurosci. Lett. 103: 349-353), and paw tests upon administration of substances such as carageenan, capsaicin or bradykinin. Arthritic conditions can be simulated by various models, including injection of agents such as carageenan, uric acid or mustard oil or adjuvant into various joints. Visceral pain can be modeled by intraperitoneal injection of substances such as bradykinin, acetylcholine, acetic acid or phenylquinone. The streptozocin (STZ)-induced diabetes neuropathy model induces a reproducible mechanical allodynia within 3 weeks (Chen and Pan, J Neurophysiol 87: 2726-2733, 2002).

Tests for neuropathic pain resulting from peripheral nerve injury include chronic constriction injury (e.g., Bennet and Xie model of sciatic nerve ligation, Pain 33: 87-107); partial nerve ligation (Seltzer et al., J Basic Clin. Physiol. Pharmacol. 1991), spinal nerve transaction or ligation (Lombard et al., Pain. 1979 6:163-74; Kim & Chung, Pain. 1992; 50:355-63), cryoneurolysis (Deleo et al., Pain. 1994; 56:9-16) sciatic nerve ischemia (Kupers et al., Pain. 1998; 76:45-59). A common test is the tactile allodynia test (Chaplan et al. (1994) J. Neurosci. Meth. 53: 55-63). Taxol induced neuropathic pain does not contain an inflammatory component. Models that are specific for certain peripheral neuropathic conditions include animal models of trigeminal nerve neuralgia (Vos and Maciewicz, J Neurosci. 1994; 14:2708-23), diabetic neuropathy (Burchiel et al., Diabetes. 1985; 34:1210-3), and vincristine neuropathy (Aley et al., Neuroscience. 1996; 73:259-65). The neuroma model (Wall et al., Pain. 1979 October; 7:103-11) can reflect phantom pain resulting from limb amputation.

Animal models of pain resulting from spinal cord injury include cord transaction or partial transaction (Levitt & Levitt, Pain. 1981; 10:129-47), an irradiation-induced ischemia model (Hao et al. Neurosci Lett. 1991 8; 128:105-8), an excitotoxic model using intraspinal injection of quisqualate (Yezeierski & Park, Neurosci Lett. 1993 9; 1571):115-9) and a contusion model (Siddall et al., Neuroreport. 1995; 6:1241-4).

5. Animal Models of Epilepsy:

A wide number of animal models of different epileptic conditions are well characterized. See, e.g., Models of Seizures and Epilepsy (ed. Pitkanen et al., ISBN: 978-0-12-088554-1; Elsevier Inc., 2006) incorporated by reference in its entirety. The animals can vary from drosophila to primates, in which epilepsy is brought about in a variety of ways including by administration of chemicals or genetic screening for specimens that spontaneously develop seizures and/or epilepsy Examples of animal models include hyperthermia-induced seizures in rats that mimics febrile seizures, mouse mutants such as totterer, stargazer, lethargic, and slow wave epilepsy (SWE) mice that share characteristics similar to human absence epilepsies such as brief behavioral arrest (i.e., staring or gazing);

Well-characterized animal models have also been described for complex partial seizures observed in patients with temporal lobe epilepsy (TLE). The kainic acid and pilocarpine (PILO) seizure models are probably the most commonly studied chemical-inductive animal models for TLE. Kindling, a phenomenon whereby repetitive, focal application of initially subconvulsive electrical stimulation ultimately results in intense partial and generalized convulsive seizures, continues to be an informative model for TLE.

In addition, several genetically epilepsy-prone species have been described as animal models for studying photosensitive and audiogenic reflex epilepsies. These include the baboon Papio papio, the Fayoumi epileptic (FEpi) strain of chickens, the genetically epilepsy prone rat (GEPR) and DBA/2 mice.

A variety of methods are available for inducing generalized tonic-clonic or absence seizures in animals, as are some genetic animal models that are either highly seizure-prone or have spontaneous seizures. The following are a few traditional methods of eliciting such seizure types.

Convulsive seizures, characterized by tonic hindlimb extension/flexion followed by clonic activity, are reliably induced by maximal electroshock which continues to be a popular method for the rapid screening of new anticonvulsant drugs.

Pentylenetetrazol (PTZ) is probably the most widely used systemically administered convulsant. Repeated injections of PTZ can be given to produce a type of chemical kindling that resembles electrical kindling. At high doses, PTZ (usually administered subcutaneously or intravenously) reliably produces tonic-clonic convulsions in rats or mice and is a rapid and efficient measure of both seizure susceptibility and screening of new drugs. Given systemically at low doses, PTZ can also be used to elicit absence-like seizures.

Flurothyl, a hexafluorinated ether, is a chemical inhalant used to induce a reproducible convulsive seizure pattern in rodents. In this method, rats or mice are placed in an airtight chamber into which centrally administered flurothyl diffuses; after 10-20 min flurothyl initially causes myoclonic jerks followed by severe clonic-tonic convulsions. Finally, other experimental animal models for generalized absence seizures include thalamic stimulation, systemic penicillin administration in cat, g-hydroxybutyrate treatment (GHB), and intracerebroventricular opiates, as well as the number of genetic models in rats (GAERS, WAG/Rij, SER) and mice (stargazer, tottering, lethargic, slow-wave epilepsy mice, mocha, and ducky) already described.

Animal models such as those described above, both in vivo and in vitro, have been valuable in understanding basic mechanisms of partial or generalized seizure-related phenomena and are standard techniques for evaluating new therapeutics. Sarkisian, Epilepsy & Behavior 2, 201-216 (2001), incorporated by reference in its entirety.

6. Animal Models of Anxiety

Anxiety can be induced by placing an animal, such as a rat, in an unfamiliar environment and observing a response (e.g., crossing a grid of lines or selecting open or closed tubes). For example, rats can be tested in an open field arena to determine both state of arousal and ability to habituate to a novel environment and assessed from crossing gridlines. A reduction in crossings indicates reduced anxiety. Rats can also be tested in a maze to assess anxiety/emotionality in rats. A suitable maze has 4 arms (two open, two closed: 15 cm width and 60 cm length) extending from a central platform and elevated 1.5 m from the floor. Rats are placed in the center of the maze and given free choice to enter any arm; operationally defined as having head and forepaws in an arm. Time spent in either the open or closed arms is recorded and scored from video recordings made simultaneously from two directions (overhead and horizontal). Increased time spent in the open arms indicates reduced anxiety because rats naturally tendency is to avoid open spaces.

7. Animal Models of Cancer

The activity of agents against cancer can be tested in immunodeficient mice or rats transplanted with human tumors. Examples of immunodeficient strains of mice that can be used are nude mice such as CD-1 nude, Nu/Nu, Balb/c nude, NIH-III (NIH-bg-nu-xid BR); scid mice such as Fox Chase SCID (C.B-17 SCID), Fox Chase outbred SCID and SCID Beige; mice deficient in RAG enzyme; as well as nude rats. Experiments are carried out as described by e.g., Kim et al., Nature 362:841 (1992). Human tumor cells typically grown in complete DMEM medium are typically harvested in HBSS. Female immunodeficient, e.g., athymic nude mice (4-6 wk old) are injected s.c. with typically $5\times10^6$ cells in 0.2 ml of HBSS in the dorsal areas. When the tumor size reaches 50-100 mm$^3$, the mice are grouped randomly and appropriate regime of an agent is administered in parallel with a control regime lacking the agent. Tumor sizes are determined typically twice a week by measuring in two dimensions [length (a) and width (b)]. Tumor volume is calculated according to $V=ab^2/2$ and expressed as mean tumor volume±SEM. The effect of an agent can be measured by growth of the tumor with time, prolongation of the survival of the mice, or increase in percent of the mice surviving at a given time or indefinitely. Statistical analysis relative to a control group may be performed using, e.g., Student's t test.

8. Internalization Peptides

A peptide or other agent can be tested for internalization or transport activity in an animal. The agent (such as a Tat peptide) can for example be labeled and injected into an animal, such as a mouse. Intraperitoneal or intravenous injection is suitable, for example. About an hour after injection, the mice are sacrificed, perfused with fixative solution (3% paraformaldehyde, 0.25% glutaraldehyde, 10% sucrose, 10 U/mL heparin in saline). Brains are then removed, frozen and sectioned. Sections are analyzed for fluorescence using a confocal microscope. Internalization activity is determined from fluorescence, optionally relative to positive and negative controls. A suitable positive control is an agent comprising a standard Tat peptide. A suitable negative control is fluorescently labeled active agent lacking Tat. Unlabelled vehicle can also be used as a negative control.

Similar experiments can be performed in cell culture to test internalization peptides or other agents (see US20030050243). A variant fluorescently labeled Tat peptide, optionally linked to an active peptide is applied to a cortical neuronal culture. Uptake is determined using fluorescence microscopy over several minutes after application. Increased uptake can be determined relative to positive and negative controls as described for the experiments on uptake in an animal.

EXAMPLES

Example #1

Identification of ND2 Sequences Responsible for Binding to Src Kinase

GST-fusion proteins were designed using different fragments of ND2 and expressed and purified using standard protocols. These purified proteins were spotted onto membranes for probing with biotinylated Src 40-58 peptide or a scrambled control peptide (sSrc 40-58). In general, 1-10 ug of peptide or recombinant protein was spotted onto nitrocellulose and dried overnight. Membranes were blocked with 5% milk for 1 h at room temperature, then incubated with biotinylated peptides (~15 ug/ml) for 2 hours the washed using standard wash buffers. Bound probe was detected using a short incubation with streptavidin conjugated to horseradish peroxidase (SA-HRP) and standard detection reagents, predominantly chemiluminescence kits. FIG. 1B shows the first set of constructs, and FIG. 1C is a dot blot that demonstrates that full length ND2 can bind Src 40-58, and that a sub fragment termed ND2.1 (AA239-321) can also bind Src 40-58. Further GST-constructs were made to narrow the core Src binding regions (FIG. 2A). Dot blots were made with these constructs and tested for their ability to capture biotinylated Src 40-58 (FIG. 2B). ND2.1.4 (AA 289-321) was the most effective sub fragment for binding Src 40-58, while none of the fragments tested bound the scrambled negative control (B-sSRC 40-58), demonstrating specificity of the interactions.

As a confirmation, ELISA assays were performed to demonstrate this binding in a different assay format. GST-ND2, GST-ND2.1 or GST-ND2.1.4 were coated onto ELISA wells by incubating at the indicated concentration under standard conditions. Wells were blocked using 5% milk, and either biotin-Src 40-58 (FIG. 2C top) or biotin-sSrc 40-58 (bottom) were incubated at 6 uM. SA-HRP and standard detection reagents demonstrated that Src 40-58 can bind each of these ND2 constructs in a concentration-dependent manner.

Further GST constructs were made to identify the amino acid sequences in ND2.1.4 responsible for binding to Src 40-58 (FIG. 3A). Although these sequences are minimally responsible for binding, sequences corresponding to ND2 these sequences as well as those flanking them could be used for inhibition of the Src-ND2 interaction. Dot blot using these GST proteins and probing again with Biotin-Src 40-58 showed ND2 310-321 binding with high relative affinity. In addition, binding was seen with ND2, ND2 289-309, 299-318, 302-321, and 307-321 (FIG. 3B). As before, interactions with all of the fragments were confirmed in an ELISA assay (FIG. 3C), and the top binders were ND2 310-321, ND2 289-309, ND2 299-318, ND2 307-321 and full length ND2. These four fragments all provided superior binding to Src 40-58 than the full length ND2. All fragments tested were able to bind Src40-58 more strongly than the negative control peptide sSrc 40-58.

We next examined the ability of the ND2 constructs to bind to a shorter version of the Src binding domain—Src 40-49 (FIGS. 4A, B). ND2 310-321, ND2 307-318, and ND2 310-318 were the top binders of Src 40-49 by dot blot analysis (FIG. 4A). These interactions were confirmed by ELISA, ND2 310-321 showing strongest binding.

Next, we confirmed the interactions between ND2 310-321 and Src 40-49 in different assay formats with different constructs. FIG. 5A shows a dot blot in which the indicated Src fragments were probed with biotinylated ND2 310-321 (Bio-ND2 310-321) or scrambled biotinylated ND2 310-321 (Bio-sND2 310-321). Src40-49-Tat indicate a fusion peptide in which the human HIV-1 tat protein transduction domain [YGRKKRRQRRR] (SEQ ID NO:2) was fused to the C-terminus of the Src40-49 sequence to result in a peptide with a sequence KPASADGHRGYGRKKRRQRRR (SEQ ID NO:9), whereas Tat-Src40-49 indicates a fusion peptide in which the Tat domain was fused to the N-terminus of Src 40-49 to create a peptide having the sequence YGRKKRRQRRRKPASADGHRG (SEQ ID NO:10). The dot blot indicates that both Tat fusion Src40-49 peptides bound ND2 310-321, as did the Src40-49 peptide itself. Binding of biotinylated ND2 310-321 to the indicated plated Src peptides was also evaluated in an ELISA assay, and each of the 4 Src constructs was able to capture biotin-ND2 310-321 (FIG. 5B). The peptides were plated at a concentration of ~5 uM. Similarly, when an ELISA plate was coated with Tat-ND2 310-321 under standard conditions, bio-Src 40-49 was able to bind in a concentration dependent manner whereas no binding was seen with the biotinylated scrambled control peptide (FIG. 5C; Bio-sSrc 40-49).

Competition ELISAs were also performed. FIG. 5D shows a competition ELISA assay testing the ability of tatSrc40-49 to inhibit the binding of biotinylated Src40-49 to ND2 310-321. The results indicate that the binding of biotinylated Src40-49 to ND2 310-321 was inhibited by tat Src 40-49 peptide. FIG. 5E demonstrates the ability of Src40-49-Tat to inhibit the binding of biotinylated Src40-49 to Tat-ND2 310-321, which was pre-coated on ELISA plates. The results indicate that the binding of biotinylated Src40-49 to Tat-ND2 310-321 was inhibited by Src 40-49-Tat peptide. In a similar manner, ND2 constructs bearing amino acid sequences from the 300-321 region are able to act as inhibitors of the interaction between ND2 and Src.

Figure 6:
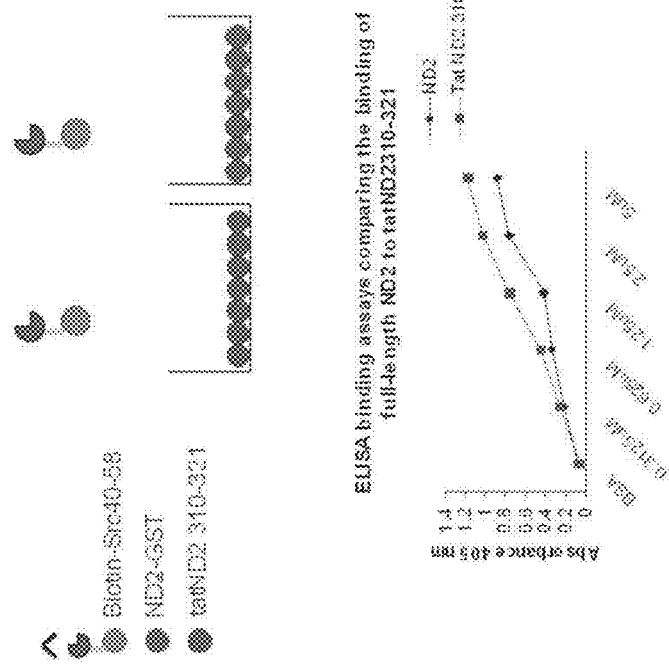
FIG. 6: ELISA assay demonstrating Src 40-58 is able to bind Tat-ND2 310-321 more strongly than ND2 310-321.

FIG. 6 again shows that Tat-ND2 310-321 is able to bind Src 40-58 better than GST-ND2. FIG. 7 shows that increasing concentrations of Tat-ND2 310-321 can compete for the binding of Bio-Src40-49 to coated ND2 310-321 peptide in a competition ELISA.

Taken together, the core ND2 sequences for mediating binding between ND2 and Src are likely between amino acids 310 and 321 of ND2, and amino acid sequences from 289 to 321 are likely to contribute to or affect binding of ND2 and Src.

Example #2

Inhibitors of the Src-ND2 Interaction Reduce Co-Localization of Src-ND2 In Vivo but not ND2 and NMDAR A series of experiments was performed to examine the localization of ND2, Src, NMDAR subunits, and PSD95 in hippocampal neurons by immunocytochemistry in the presence of Tat, Tat-ND2 310-321, or Src 40-49-Tat. Briefly, hippocampal neurons were isolated from embryonic day #17/E18 Wistar rats, and cultured in neurobasal media containing coverslips with B27 and glutamax. Cells were then treated for 1 hr with luM peptide before fixing by standard methods. Proteins were visualized using specific antibodies and secondary antibodies coupled to fluorescent molecules. Colocalization of fluorescence was calculated by merging the images in Photoshop and calculating the % colocalized between pairs as the total colocalized fluorescence clusters divided by the total number of clusters (e.g., % colocalized ND2 with Src= (total colocalized)/(total ND2 clusters); % colocalized Src with ND2=(total colocalized)/(total Src clusters)).

FIGS. 8A and 8B show that incubation with either Tat-ND2 310-321 or Src 40-49-Tat are able to reduce the amount of colocalization of Src and ND2, whereas the control Tat transporter does not. Thus, these peptides are able to cross cellular membranes and disrupt the complexes that are pre-formed inside cells and can be used as therapeutics.

Figure 10:
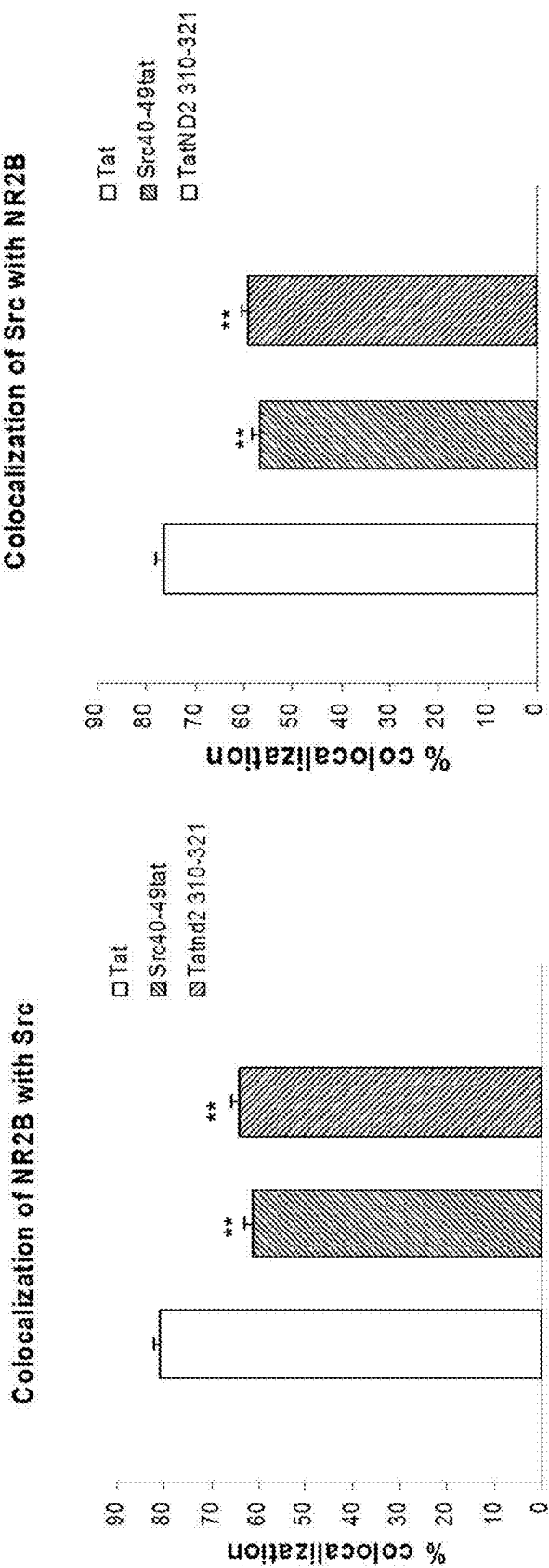
FIG. 10: Quantification of the co-localization of Src and NMDAR 2B in 14DIV hippocampal neurons with and without treatment with Tat-ND2 310-321 or Src 40-49-Tat.
Figure 11:
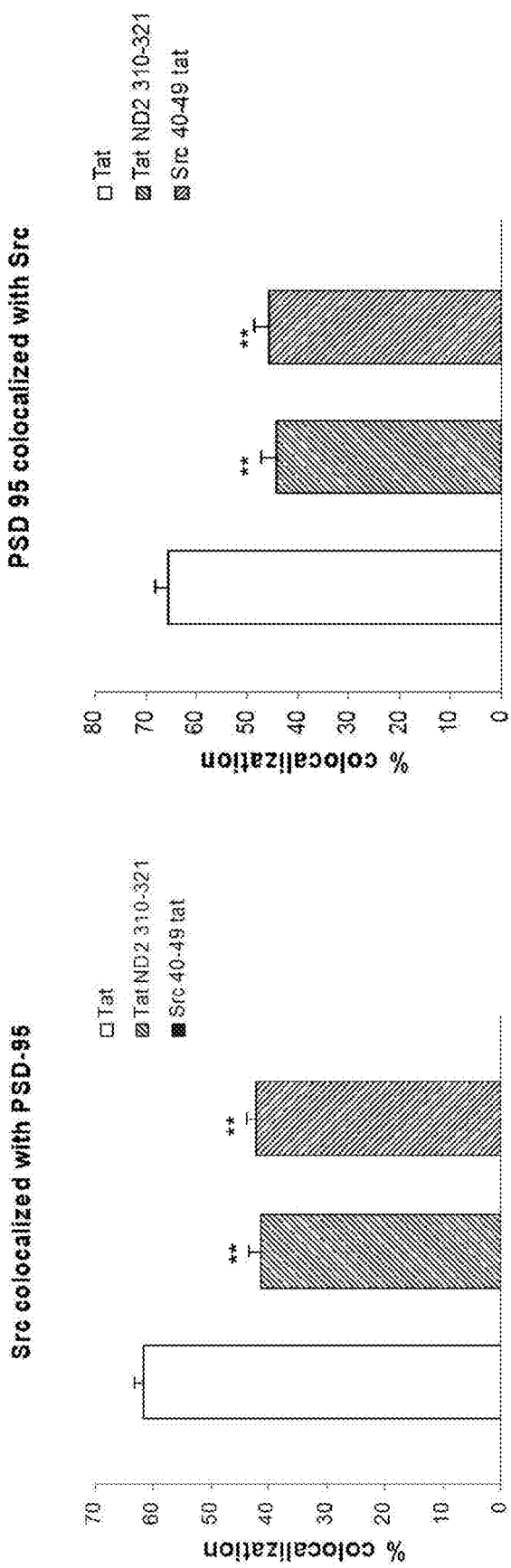
FIG. 11: Quantification of the co-localization of Src and PSD95 in 14DIV hippocampal neurons with and without treatment with Tat-ND2 310-321 or Src 40-49-Tat.

Next, the localization of ND2 with NMDA Receptor subunit 2B (NR2B) and PSD95 in the presence of these inhibitors was examined. Both Tat-ND2 310-321 and Src 40-49-Tat do not significantly affect the association between ND2 and NR2B in spite of disrupting the interaction between ND2 and Src (FIGS. 9A, B compared to FIGS. 8A, B). Surprisingly, disruption of the interaction between Src and ND2 reduces the colocalization of ND2 with PSD95 (FIGS. 9C, D). As PSD95 is known to associate with the NR2B though an interaction between the C-terminus of NR2B and the first two PDZ domains of PSD95 (Aarts et al, Science, 2002), these drugs provide alternate compositions for and methods of achieving the benefits of disrupting the NMDAR-PSD95 interaction. Those include the treatment of stroke, disorders associated with excitotoxicity, pain, neurodegenerative disorders, anxiety, epilepsy, optical neuropathies, and more. Consistent with this disruption of the colocalization of PSD95, FIGS. 9E and F show that the colocalization between PSD95 and NR2B is similarly disrupted. In a similar manner, Tat-ND2 310-321 and Src 40-49-Tat are able to reduce the colocalization between NR2B and Src (FIG. 10) and PSD95 and Src (FIG. 11).

Thus, compounds that contain ND2 sequences inhibiting the binding between Src and ND2 can modulate the NMDA Receptor complex, especially the associations between NR2B and Src and NR2B and PSD95.

Antibodies

The following primary antibodies were used in this study: Mouse mAb to NR2B (Cat#:ab 28373), Mouse mAb to PSD95 (clone 7E3-1B8, Cat#: ab13552) and Mouse mAb to Src(clone 327, Cat#: ab16885) were from Abcam (Cambridge, Mass.); Rabbit anti-NR2B (Cat#: 06-600) was from Millipore (Temecula, Calif.); Goat anti-ND2 (M-16, Cat#: sc-20496) and Rabbit anti-GST (Z-5, Cat#: sc-459) were from Santa Cruz Biotechnology (Santa Cruz, Calif.); Phospho-Tyrosine Mouse mAb (P-Tyr-100, Cat#: 9411), Phospho-NR2B (Tyr1472, Cat#: 4208) and Rabbit anti-PSD 95 (D27E11, Cat#: 3450) were from Cell Signaling Technology (Danvers, Mass.).

All of the secondary antibodies used in this study were from Jackson ImmunoResearch Laboratory (West Grove, Pa.): Texas Red-Donkey anti-Rabbit (711-075-152), Texas Red-Donkey anti-Mouse(711-075-150), Texas Red-Donkey anti-Goat (705-075-003), FITC-Donkey anti-Rabbit (711-095-152), FITC-Donkey anti-Mouse (715-095-150), FITC-Donkey anti-Goat (705-095-003), Peroxidase Goat anti-Mouse (115-036-006), Peroxidase Goat anti-Rabbit (111-036-047) and Peroxidase Rabbit anti-Goat (305-036-003)

Immunocytochemistry

Hippocampal neurons cultured on coverslips were treated with 1 uM of Src 40-49-Tat, Tat-ND2 310-321 or Tat for 1 h at the day 14. Then neurons were incubated in 4% paraformaldehyde and 4% sucrose in phosphate-buffered saline (PBS) for 10 minutes followed by 5 minutes 20% methanol at room temperature (RT). Cells were permeabilized with 0.25% Triton X-100 in PBS for 5 minutes and by treatment with 5% donkey serum in PBS for 30 minutes at RT. The cultures were incubated with a mixture of the primary antibodies, raised in various species, in 0.25% Triton X-100 PBS for 2 hours at RT, washed, and incubated for 1 hour at RT with a mixture of species-specific secondary antibodies all raised in donkey and conjugated to either Texas Red, or FITC fluorophores (1:200 dilution in 0.25% Triton X-100 PBS). The coverslips were washed with PBS and mounted using ProLong Gold antifade reagent (Invitrogen). Images were collected using a 60× pan-fluor objective on a Nikon Eclipse TE 200 microscope. The images were analyzed with PhotoShop 7 (Adobe, San Jose, Calif.). Brightness and contrast were adjusted, sharpened using the unsharpen mask tool, and the images were merged for color colocalization.

For quantification of the colocalization, the maximum intensities of the fluorophore channels were normalized and the background fluorescence of each channel seen in the dendrites was subtracted, the color images were merged. Two clusters in two different channels were considered colocalizing when at least 66% of the surface of one clusters in one of the two channels overlapped with a clusters in the other channel. For each combination of antibodies, three independent immunofluorescence experiments were done. Each measurement was taken from a 50-m-long dendritic segment (with an average width of 2 m). Colocalization was expressed as the percent of the total clusters analyzed.

Example #3

Inhibitors of the ND2-Src Interaction Affect the Composition of the NMDA Receptor Complex Co-immunoprecipitation experiments were used to examine the status of selected proteins in the NMDA Receptor complex in neurons. These were examined in both hippocampal neurons and in rat brains subjected to stroke using the 3 PIAL vessel occlusion model (3PVO), and in the presence or absence of inhibitors of the Src-ND2 interaction. FIGS. 12A-E demonstrates the status of the NMDAR in Day 14 hippocampal neurons. Antibodies against ND2, Src, PSD95, NR2B and IgG alone were added to lysates as described below and used to generate clean immunoprecipitates (antibodies listed on top of the blots). Each blot is then probed with a detection antibody using standard western blot techniques, using the antibody listed below each blot. This figure demonstrates that each of the immunoprecipitating antibodies is able to pull down a complex containing ND2, Src, PSD95 and NR2B.

We next examined the effect of Tat-ND2 310-321 and Src40-49-Tat on the association of proteins in the NMDAR signaling complex in cultured hippocampal neurons at 14DIV. Neurons were treated with Tat-ND2 310-321 or Src40-49 at 1 uM for 1 hour (FIG. 13A) or at 3 uM for 2 hours (FIG. 13B). Cell lysates were purified and immunoprecipitated with anti-NR2B (left) and then stained with anti NR2B, anti-PSD95, anti-Src and anti-ND2 antibodies. These studies illustrate that treating the neurons with both Tat-peptides reduces the association of NR2B with Src. At the concentrations and exposure times used, there appears to be a slight reduction in the association PSD95 and NR2B when pretreated with Tat-ND2 310-321. This experiment was repeated, and clearly showed that Tat-ND2 310-321 treatment significantly decreased the amount of PSD-95 and Src in the NMDAR complex when compared to Src 40-49-Tat after immunoprecipitation with antibodies against NR2B (FIG. 13C, left). When the same peptide treated lysates were used for immunoprecipitation with anti-PSD95 antibodies, treatment with Tat ND2 310-321 significantly reduced the amount of NR2B normally associated with PSD95. Further, in another set of immunoprecipitation experiments using anti-PSD95 antibodies on peptide-treated hippocampal neuron lysates, Tat-ND2 310-321 was able to nearly abolish the association between NR2B and PSD-95, and reduce the amount of phosphorylated NR2B associated with PSD95 (FIG. 13D).

Figure 15:
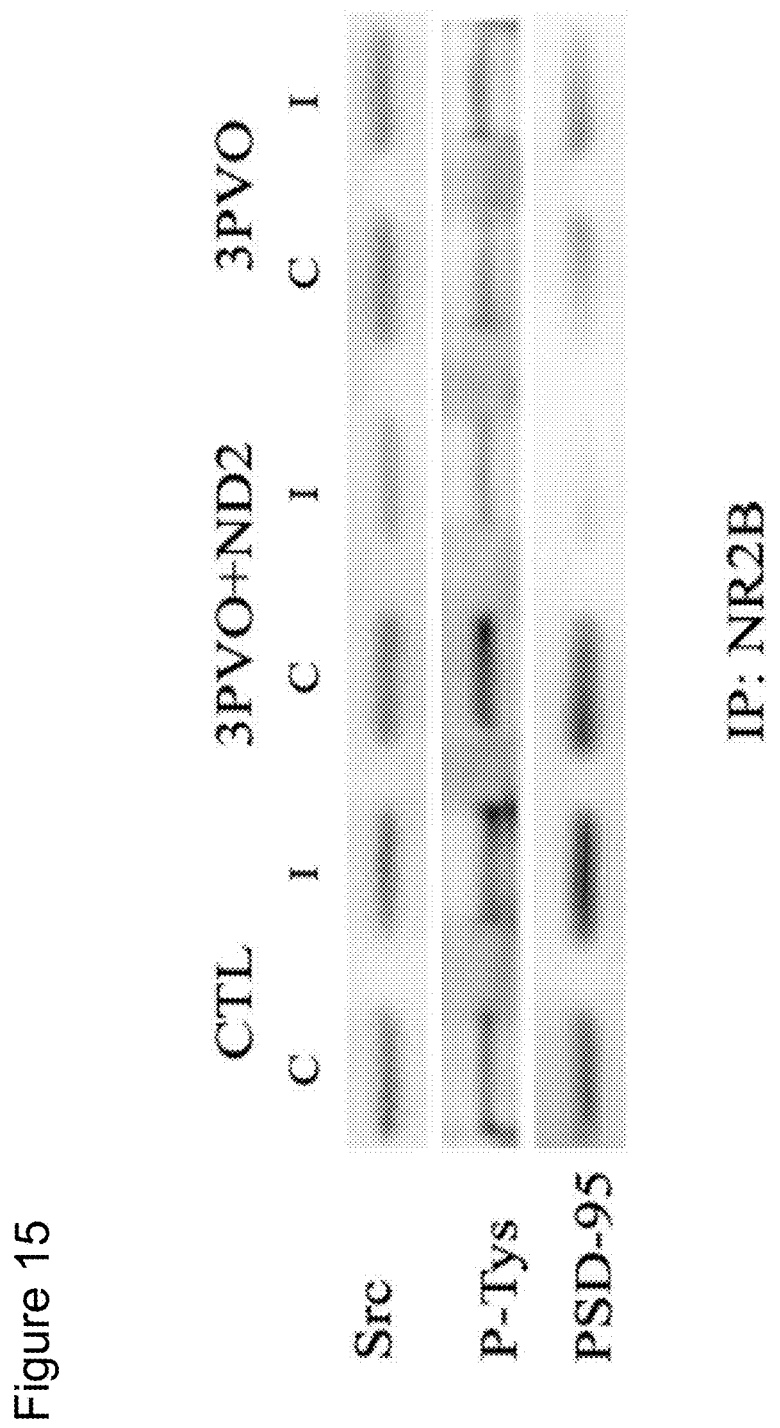
FIG. 15: Co-immunoprecipitation using anti-NR2B antibodies from rat brains subjected to 3PVO or 3PVO and treatment with 3 uM Tat-ND2 310-321. C—contralateral brain extract; I—ipsilateral brain extract. Labels indicate the detection antibody used, and P-Tys indicates an antibody against phosphorylated tyrosine 100 of Src.

The status of these proteins was next examined in rat brains that had been subjected to a 3PVO stroke. After 3PVO ischemia, rodents were given either Tat-ND2 310-321 or saline via tail vein injection. At one hour post-surgery, the brains were quickly harvested and lysed. Following IP with anti NR2B antibodies, the membranes were incubated with anti phosphotyrosine antibodies, developed, and subsequently probed with anti Src, phosphorylated Src (pTys) and anti PSD95 antibodies. As an internal control, both the ipsilateral and contralateral hemispheres (I and C, respectively) were prepared. FIG. 15 shows that in the Tat-ND2 310-321 treated animals, far less PSD95 is immmunoprecipitated along with the NR2B subunit, and the amount of Src is reduced as well. This change in the NR2B composition appears to occur only in the stroke hemisphere, as PSD95 appears to remain associated with NR2B in the hemisphere not subjected to stroke. This is significant, because the reduction of PSD95:NR2B association in stroke tissues is protective, but the NMDAR complex is required for other tissue functions such as neuronal signaling and long term potentiation. Thus, Tat-ND2 310-321 shows the potential to selectively protect brain areas affected by stroke without disrupting the complex in unaffected areas, likely leading to reduced side effects when compared to a generalized PSD95:NMDAR inhibitor.

Figure 16:
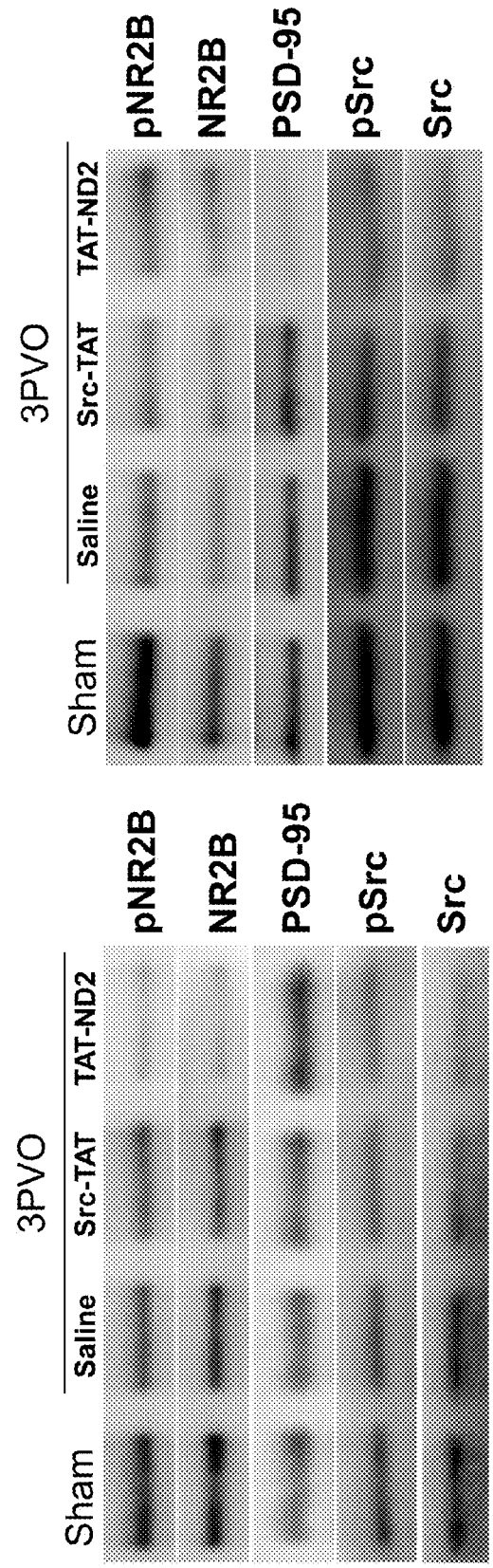
FIGS. 16A, B: Co-immunoprecipitations using either anti PSD95 or anti NR2B antibodies, demonstrating the status of proteins with the NR2B complex in the presence or absence of Src-Tat or Tat-ND2.

A second set of experiments was performed on animals subjected to 3PVO, modified such that the saline, Src 40-49-Tat or Tat-ND2 310-321 was administered by tail vein injection 1 hour post-surgery and the brains were harvested and lysed 2 hours post-surgery. FIGS. 16A, B show the results of immunoprecipitations from these brains using either PSD95 as the IP antibody (FIG. 16A) or NR2B (FIG. 16B). In A, Tat-ND2 310-321 significantly reduced the about of NR2B, phosphorylated NR2B and Src associated with PSD95. Conversely, in B following immunoprecipitation with anti-NR2B antibodies, very little PSD95 is associated with the complex, and less Src and PhosphoSrc (pSrc) as well. The Src 40-49-Tat construct was not nearly as effective in uncoupling PSD95 and Src from the NMDA Receptor.

Co-Immunoprecipitation Methods

NMDAR and its associated proteins were prepared from cultured hippocampal (HP) neurons or rat brains. For in vitro competition experiments, two week HP neurons were collected after treatment with Src 40-49-Tat, Tat-ND2 310-321 or Tat peptides for 1 h at luM concentration or for 2 hours at 3 uM concentration then cells were quickly harvested and homogenized. For in vivo experiments, one hour after 3PVO ischemia, rats were injected with indicated peptides or saline by intravenous tail vein. Two hours after surgery (one hour after administration of compounds), the selected cortex of the brain was quickly harvested and homogenized.

Lysates were incubated with Dynabeads protein G (Invitrogen) and selected antibodies for 30 minutes at room temperature. Isolated immunoprecipitates were resolved using SDS-PAGE and transferred to nitrocellulose membranes. The membranes were probed with selected detection antibodies, then stripped and reprobed with other detection antibodies.

Example #4

ND2 Inhibitors Inhibit PACAP-Enhanced NMDA-Evoked Currents in CA1 Neurons

Pituitary Adenylate Cyclase-activating Polypeptide (PACAP) selectively increases NMDA receptor mediated responses in rat neurons, and it is thought that this peptide is involved in the regulation of synaptic plasticity as well as both long term potentiation and depression. To examine the effect of ND2 310-321 and Src 40-49 on PACAP-enhanced NMDA-evoked currents, isolated CA1 neurons were subjected to a series of patch clamp experiments in the presence or absence of these peptides. FIG. 14A shows the normalized peak current with PACAP (1 nM) in the patch pipette or PACAP+ND2 310-321 (6 mM). ND2 310-321 can prevent PACAP-induced potentiation. Similar experiments were also performed using the Src-selective inhibitory peptide, Src(40-58) (14 mM), or the truncated peptide, Src(40-49) (6 mM). The responses prior to application of PACAP were normalized the responses at 25 to 30 minutes following application of PACAP. The bar graph indicates three groups of recordings from neurons and indicated the relative change in peak NMDAR currents under the three conditions. ND2 310-321, but not Src40-49, inhibits PACAP-enhanced NMDA-evoked currents. Thus, ND2 310-321 can be used to block PACAP enhanced NMDA-evoked signaling and can therefore be used in many neurological diseases and disorders associated with impaired with long term potentiation (e.g., aging, Alzheimer's, neurodegenerative diseases and neuronal disorders affect memory).

Example #5

ND2 Inhibitors Reduce Pain Hypersensitivity in Rodents

Figure 17:
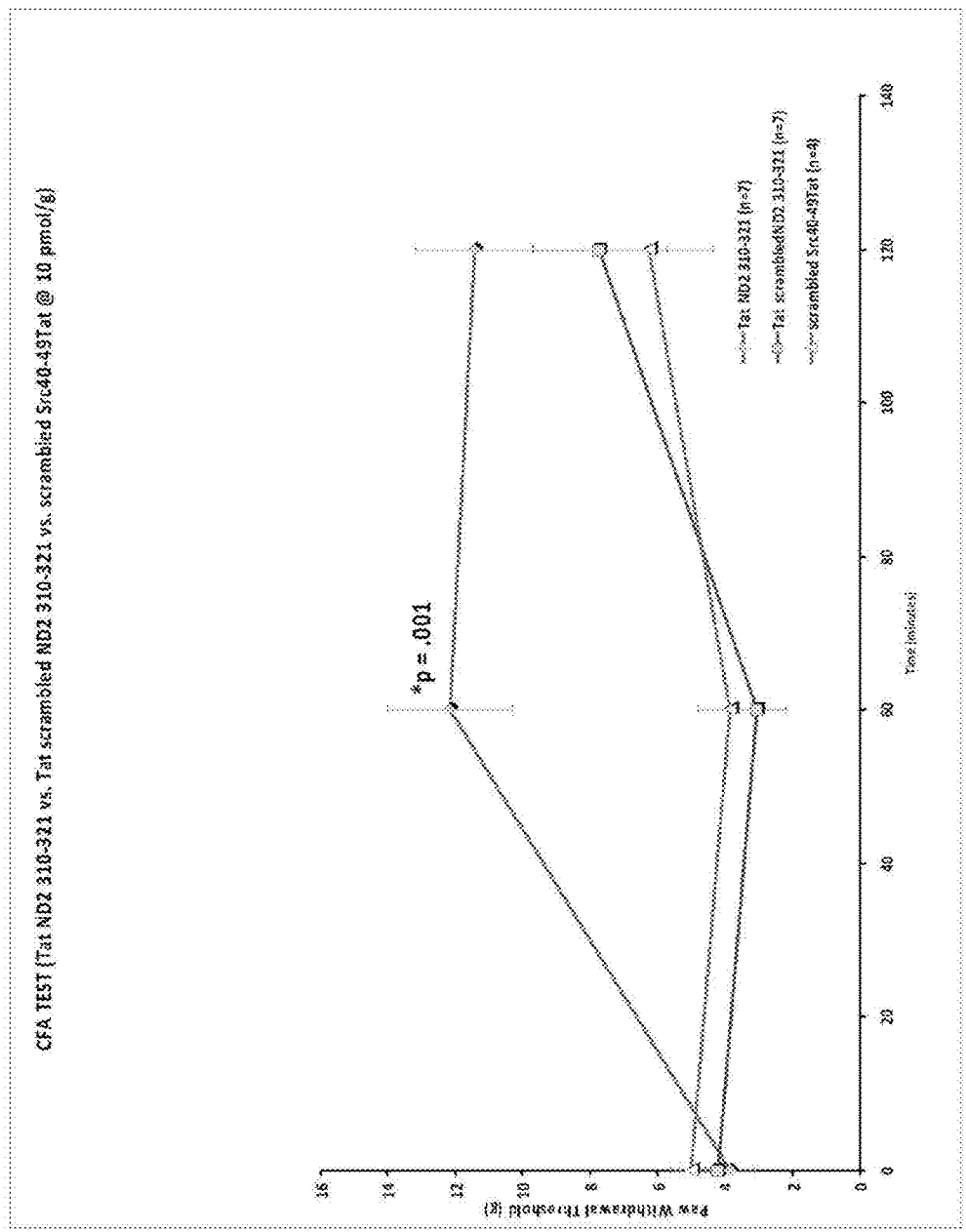
FIG. 17: Treatment with Tat-ND2 310-321 reduces pain hypersensitivity in a model of CFA-induced pain.

To demonstrate that Tat-ND2 310-321 is effective in reducing pain hypersensitivity, 10 pmol/g of Tat ND2 310-321 or scrambled ND2 or Src negative control peptides were administered via tail vein injection to rats with previously induced inflammation in their hind paws from subcutaneous injection of complete Freund's adjuvant (CFA). Measurement of pain hypersensitivity was performed using filaments of different stiffness as described in the methods either 1 hour or 2 hours following injection of the peptides. Animals treated with Tat-ND2 310-321 were significantly less sensitive to pain than animals treated with scrambled control peptides. Further, peptides containing the ND2 310-321 region such as tat-ND2 310-321 worked significantly better than Src40-49-Tat in these experiments. This difference was greater at 1 hour post dosing than at two hours under these conditions (FIG. 17).

Src 40-49-Tat has been reported to disrupt the association of Src and ND2 in neuronal lysates (Liu, X-J et al., (2008) Nature Medicine, reference 3). This disruption also reduced the association between Src and NMDA R2 subunits, which in turn reduced NMDA currents and had a beneficial effect on both inflammatory pain (Formalin and CFA models) and neuropathic pain (peripheral nerve constriction). The present results show that ND2 310-321 has a superior ability to provide pain relief in the CFA model (FIG. 17), disrupt the association between Src and NMDA R2 subunits better (FIG. 13C—IP NR2B in the presence of Tat-ND2 or Src 40-49-Tat, probing with anti-Src), and reduce NMDA currents (FIG. 14B). We interpret these results as evidence that ND2 compounds containing the 310-321 region of ND2 such as Tat-ND2 310-321 works better than Src 40-49-Tat in various models of animal pain (e.g., CFA, formalin and peripheral nerve constriction) and have the potential to be effective therapeutics for the treatment of inflammatory and neuropathic pain, chronic pain, and pain associated with hypersensitivity.

Methods

CFA Models:

Animals:

Experiments were performed on Sprague-Dawley rats (male, 250-300 g) from Charles River Laboratories (St. Constant, Quebec). They were housed in plastic cages containing ⅛" corn cob bedding and kept on a 12-hour light/dark cycle. They were housed in pairs and had access to food and water ad libitum. Use of these animals was in accordance with the guidelines of the Canadian Council on Animal Care and approved by the Animal Care Committee at Toronto Western Hospital.

Induction of Inflammation:

Briefly, Complete Freund's Adjuvant (CFA; Sigma Chemical Company, St. Louis) was injected subcutaneously into the plantar surface of the hind paw (100 ul, 27G½ needle under isoflurane anesthesia). Animals were returned to their home cages for 8 hours to allow inflammation and sensitization to develop.

Tail Vein Injection:

To administer peptide intravenously after the induction of inflammation, animals were placed in a transparent induction chamber and anesthetized with a mixture of 2.5% isoflurane in oxygen until the animal is completely anesthetized (after approximately 1 min) A mask was then be placed over the animal's nose and mouth and the isoflurane concentration lowered to 1.5-2.0% for the duration of the injection. Peptide was dissolved in 1 uL/g of sterilized saline and injections were made with a 25G½ butterfly needle (Fisher Scientific). The animal was then returned to its cage.

Measurement of Paw Withdrawal Threshold:

Based on the procedure described by Pitcher et al. (Journal of Neuroscience Methods, 1999), animals were placed on a platform containing holes 1.5 mm in diameter in a transparent plexiglass observation chamber (30×30×30 cm). An ascending series of calibrated von Frey filaments (Stoelting, USA) (0.008 g-15 g) was applied to the plantar surface of a hind paw to determine the minimum stimulus needed to elicit paw withdrawal. Each filament was applied perpendicularly for 2 seconds or until withdrawal occurred. Each successive filament was applied 5 times at 5-second intervals. The threshold was determined by the filament that elicited 3 positive responses out of 5 applications. Filaments greater than 15 g were not used to avoid tissue damage. Paw withdrawal threshold was measured prior to CFA injection, 8 hours after CFA injection, 60 minutes following peptide injection and 120 minutes following peptide injection.

Example #6

ND2 Inhibitors are Effective at Reducing Brain Damage Following Stroke

The efficacy of ND2 inhibitors in the treatment of stroke was examined using the three pial vessel occlusion (3PVO) model of stroke. This is a permanent model of stroke that creates small but consistent infarcts at 24 hours.

Figure 18:
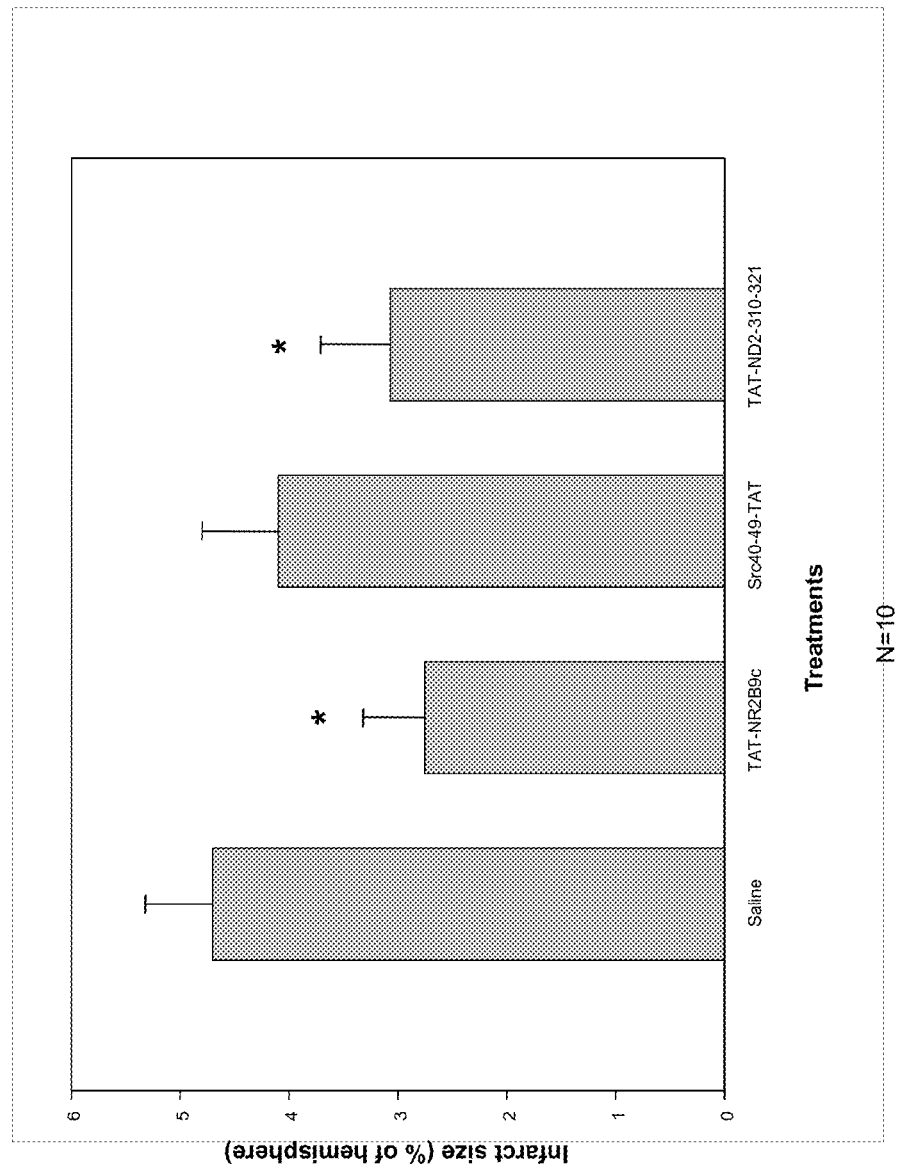
FIG. 18: Infarct sizes of rats subjected to 3PVO in the presence of Tat-NR2B9c, src40-49-Tat, or Tat-ND2 310-321.

Male Sprague Dawley rats (n=10 in each group) were surgically subjected to permanent occlusion of the pial vessels. One hour post-surgery, animals were given an intravenous injection of Saline, Tat-NR2B9c (Aarts et al, Science, 2002), Src 40-49-Tat or Tat-ND2 310-321 and allowed to further recover in their cages. 24 hours after surgery, brains were harvested, sliced and incubated with TTC to visualize the areas of infarction. The infarct volume of each animal was determined, as well as the average volumes for each group of ten. FIG. 18 shows the results of one such experiment. Tat-ND2 310-321 and Tat-NR2B9c both show an approximately 40% decline in infarct volume, whereas Src 40-49-Tat was not statistically effective in reducing infarct volumes in this model. This suggests that ND2 inhibitors of the Src-ND2 interaction, and Tat-ND2 310-321 in particular, can be effective drugs for the treatment of stroke.

Figure 22:
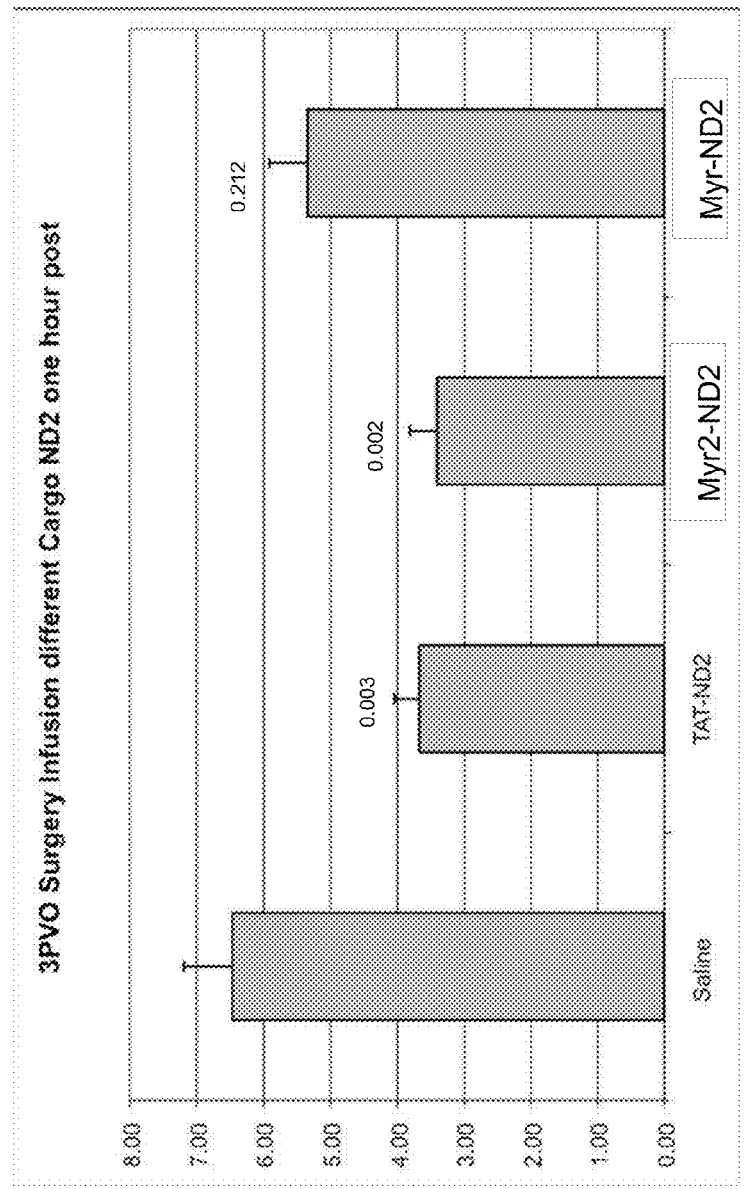
FIG. 22: Graph demonstrating the effect of Tat-ND2, myr-ND2 and myr2-ND2 in protecting the rat brain against stroke as induced in the 3PVO model when given intravenously 1 hour after the onset of the stroke.

In a second experiment, the efficacy of myristoylated versions of two ND2 peptides were assessed relative to Tat-ND2. The sequences are provided following the examples. Both peptides were myristoylated via an amide bond to the alpha-amino group of the N-terminal amino acid of the peptide. Myr2-ND2 provided equivalent or superior protection against damage from the stroke in this model, and myr-ND2 was effective but less effective than myr2-ND2 in this experiment (FIG. 22). Thus, Tat-ND2, myr2-ND2 and myr-ND2 are effective drugs for the treatment of stroke when administered after a stroke. We have also found these inhibitors effective when administered prior to a stroke.

Three Pial Vessel Occlusion Model of Ischemia

Male Sprague Dawley rats (n=10 in each group) weighing between 230 and 290 g were used for this study. Experiments were performed on fasted rats (Free overnight access to water but not food). For permanent three pial vessel occlusion (3PVO) was performed as described previously (Forder J et al., 2005, supra). In brief, rats were anesthetized with a 0.5 ml/kg intramuscular injection of ketamine (100 mg/kg), acepromazine (2 mg/kg), and xylazine (5 mg/kg), supplemented with one-third of the initial dose as required. An anal temperature probe was inserted, and the animal was placed on a heating pad maintained at 37° C. The skull was exposed via a midline incision and scraped free of tissue. Using a dissecting microscope and a pneumatic dental drill, a 6- to 8-mm cranial window was made over the right somatosensory cortex (2 mm caudal and 5 mm lateral to bregma) by drilling a rectangle through the skull and lifting off the piece of skull while keeping the dura intact. The 3 pial arteriolar middle cerebral artery branches around the barrel cortex were selected and electrically cauterized through the dura. After the cauterizations, the scalp was sutured. Each rat was returned to its individual cage under a heating lamp to maintain body temperature until the rat fully recovered. One hour after 3PVO ischemia, rats were injected with indicated drug (3 nmol/g) or saline by intravenous tail vein. Food and water was supplied. Twenty-four hours after surgery, the brain was quickly harvested. Coronal slices (2 mm) were taken through the brain and incubated in 2% triphenyltetrazoliumchloride (TTC) (Sigma) for 15 min at 37° C. Images were scanned (Canon 4200F).

Example #7

ND2 Inhibitors Reduce Pain Hypersensitivity in Rodent Models of Neuropathic Pain We next tested the effect of Tat-ND2 310-321 versus the control scrambled ND2 negative control (sTat-ND2 310-321) on neuropathic and inflammatory pain behaviors using a model of peripheral nerve injury (PNI) in rats and the Complete Freund's Adjuvant model (CFA), both characterized by a reduction of mechanical paw withdrawal threshold. The effect of Tat-ND2 310-321 on mechanical withdrawal threshold was assessed 8-15 d after PNI. We found that Tat-ND2 310-321, but not sTat-ND2 310-321, caused a significant increase in paw withdrawal threshold ipsilateral to the nerve injury when administered intravenously. Similar results were observed in the CFA model (FIG. 17), where the increase in paw withdrawal threshold developed within the first 45 minutes and persisted through the 3 hour testing period.

Thus, Tat-ND2 310-321, and peptides or peptidomimetics containing this region of ND2, can provide relief from neuropathic pain.

Methods

Chronic Sciatic Nerve Constriction Model:

Animals: To produce peripheral nerve injury (PNI), a 2 mm polyethylene cuff was surgically implanted around the sciatic nerve of rats or mice under isoflurane anesthesia. Animals were allowed to acclimatize for 7 days prior to testing.

Drug Administration

Tat-ND2 310-321 or sTat-ND2 310-321 was administered between 8 and 15 days post-surgical implantation of the nerve cuff intravenously through the tail vein at 1 nmol/g. Animals were returned to their cages after injection.

Measurement of Paw Withdrawal Threshold

Based on the procedure described by Pitcher et al. (Journal of Neuroscience Methods, 1999), animals were placed on a platform containing holes 1.5 mm in diameter in a transparent plexiglass observation chamber (30×30×30 cm). An ascending series of calibrated von Frey filaments (Stoelting, USA) (0.008 g-15 g) was applied to the plantar surface of a hind paw to determine the minimum stimulus needed to elicit paw withdrawal. Each filament was applied perpendicularly for 2 seconds or until withdrawal occurred. Each successive filament was applied 5 times at 5-second intervals. The threshold was determined by the filament that elicited 3 positive responses out of 5 applications. Filaments greater than 15 g were not used to avoid tissue damage. Paw withdrawal threshold was measured prior to nerve constriction 7 days after sciatic nerve constriction, and 45 min, 90 min, 135 min and 180 min post injection of peptides or controls.

Example #8

ND2 Inhibitors are Effective at Reducing Pain

Figure 23:
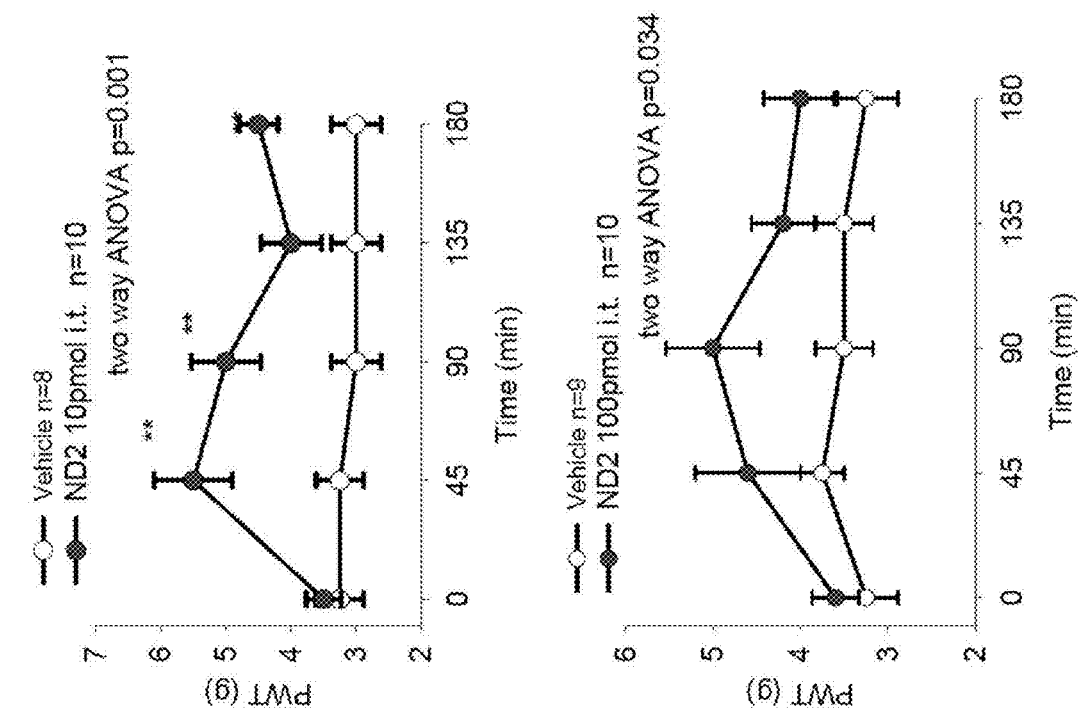
FIG. 23: Graphs demonstrating that two different concentrations of myr-ND2 are able to significantly reduce pain by measuring allodynia by paw withdrawal threshold in animals subjected to peripheral nerve injury.

Peripheral nerve injury (PNI) via the chronic sciatic nerve constriction model was induced in rodents by surgically implanting a polyethylene cuff (2 mm in length) around the sciatic nerve of rats or mice under isoflurane anesthesia. We then measured mechanical paw withdrawal threshold (PWT) with Von-Frey Filaments as described previously (Liu et al, 2008) both before surgery for the baseline and 8-14 days post-surgery. We prepared myr-ND2 (100 micromol/L) in 20% acetic acid as stock solution and diluted the stock into working concentration before testing. We injected either 10 pmol or 100 pmol of myr-ND2 and vehicle into the lumbar spinal cord and tested PWT 45 min, 90 min, 135 min and 180 min post injection. Both concentrations of myr-ND2 tested demonstrated decreased sensitivity to pain across all time points tested (FIG. 23). Thus, ND2 peptides, including myr-ND2, are effective inhibitors of pain.

Example #9

Figure 20:
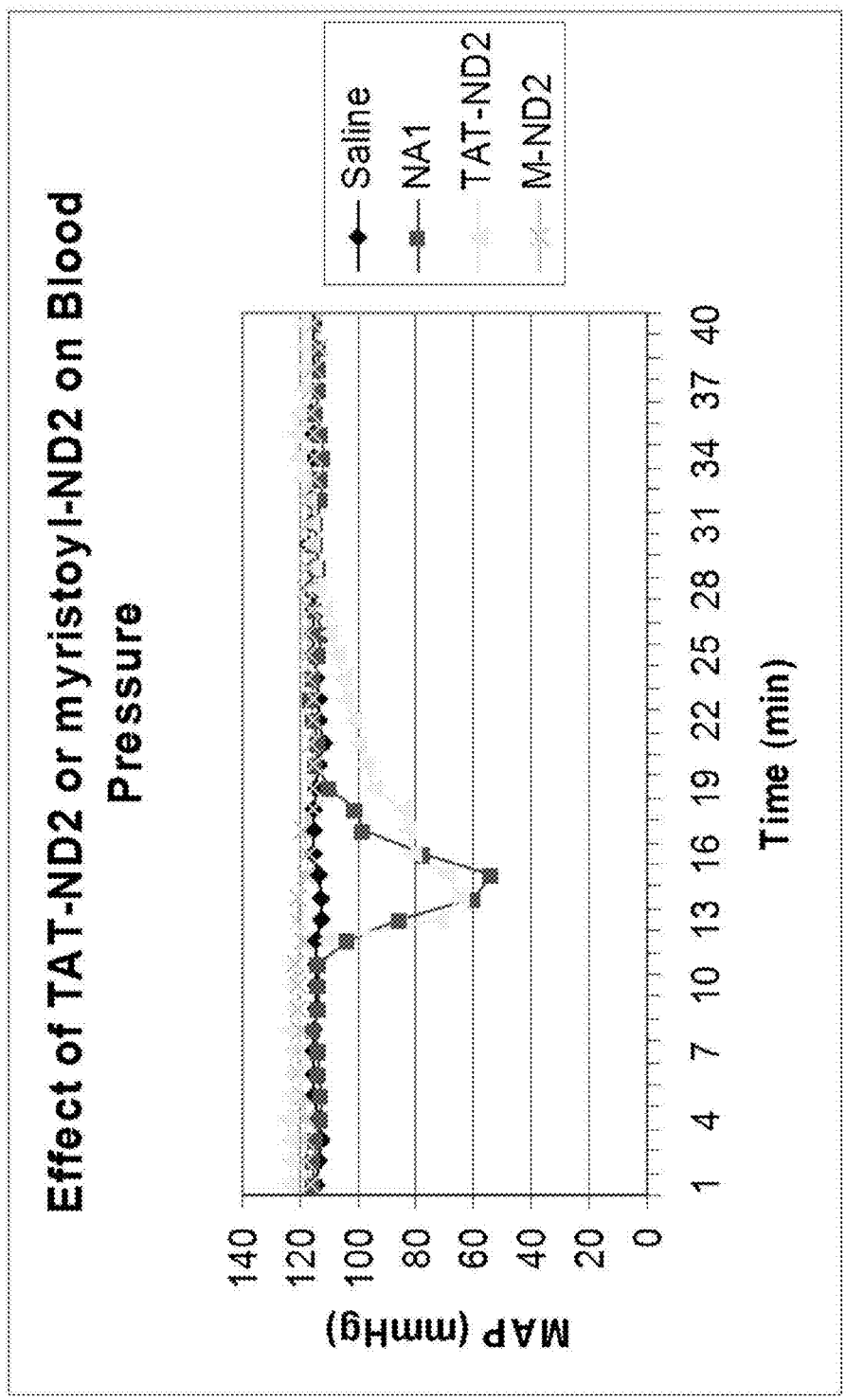
FIG. 20: Effect of Tat-ND2, myristoylated ND2 and NA-1 (also known as Tat-NR2B9c) on blood pressure when injected intravenously into rats at high concentrations.
Figure 21:
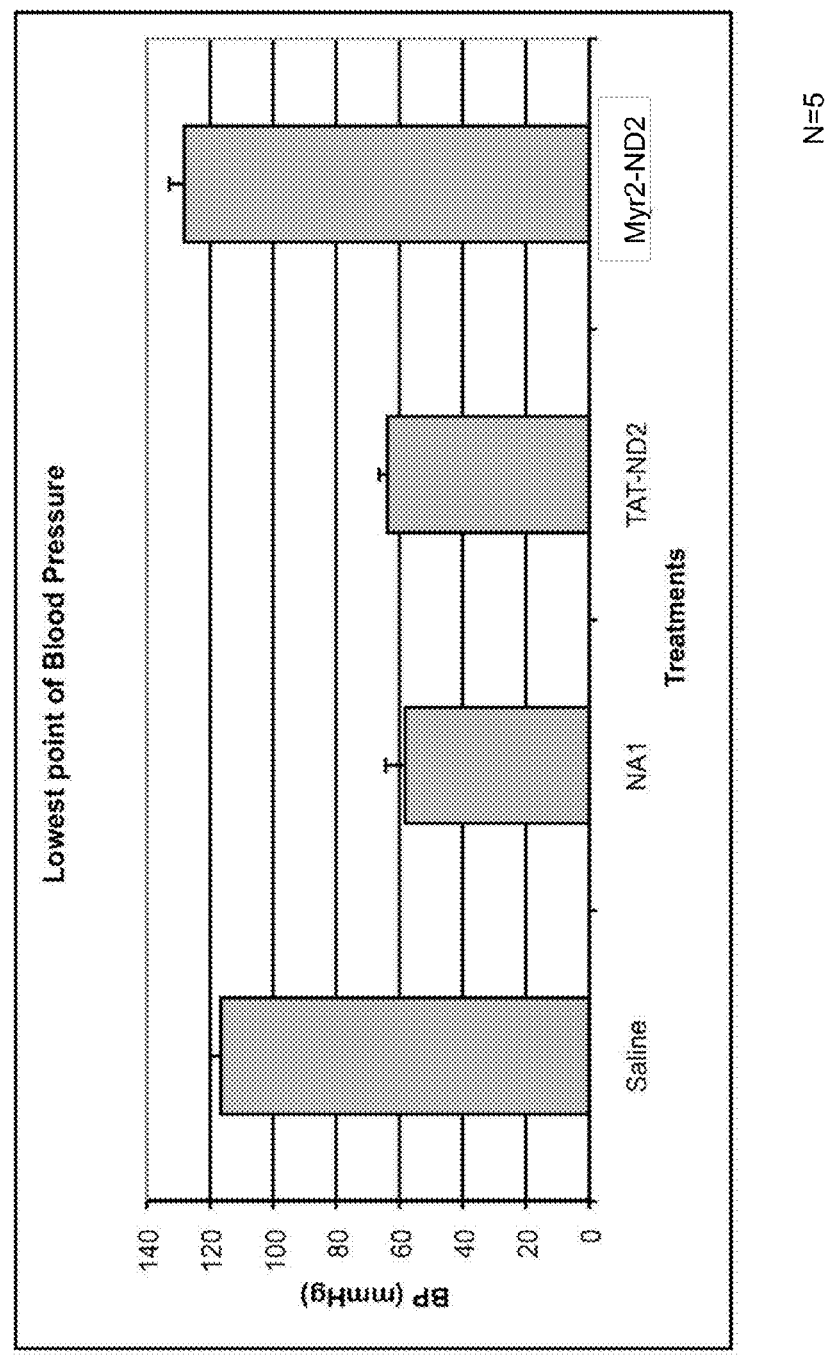
FIG. 21: Graph depicting the minimum blood pressure (maximum blood pressure drop) observed following intravenous injection of NA-1, Tat-ND2 or myr-ND2.

Myristoylation Maintains Efficacy in Pain and Stroke Models without Reducing Blood Pressure at High Dosage Levels ND2 peptide have been shown herein to be effective at reducing both pain and damage following stroke. Tat peptides have previously been shown to cause a reduction in blood pressure when administered rapidly in high doses. We tested the effective of applying a rapid bolus of high concentration myr-ND2 peptide relative to Tat-ND2 and NA-1 (Tat-NR2B9c). Rats with surgically implanted devices to measure arterial pressure were dosed with ~25 mg/kg of the respective peptides as a bolus injection into the tail vein at 10 minutes post monitoring. Both of the peptides containing Tat sequences resulted in a drop of mean arterial blood pressure to levels about one half of normal. These pressure drops resolved themselves within about 10-15 minutes without intervention. The myr-ND2 peptide, however, showed no decreases in blood pressure at similar concentrations in any of the animals tested (FIG. 20). FIG. 21 shows the lowest points in blood pressure, further demonstrating that myr-ND2 had no effect on blood pressure in this model. Thus, myr-ND2 can be administered at a higher dose level than Tat-ND2 without or with a lower chance of observing blood pressure side effects in humans.

REFERENCES

1. Liu, X. J., et al., *Treatment of inflammatory and neuropathic pain by uncoupling Src from the NMDA receptor complex*. Nat. Med., 2008. 14(12): p. 1325-1332.
2. Gingrich, J. R., et al., *Unique domain anchoring of Src to synaptic NMDA receptors via the mitochondrial protein NADH dehydrogenase subunit 2*. Proc. Natl. Acad. Sci. U.S.A, 2004. 101(16): p. 6237-6242.
3. Liu, X. J., et al., *Treatment of inflammatory and neuropathic pain by uncoupling Src from the NMDA receptor complex*. Nature Medicine, 2008. 14(12): p. 1325-1332.
4. Husi, H., et al., *Proteomic analysis of NMDA receptor-adhesion protein signaling complexes*. Nat. Neurosci., 2000. 3(7): p. 661-669.
5. Kalia, L. and M. Salter, *Interactions between Src family protein tyrosine kinases and PSD-95*. Neuropharmacology, 2003. 45(6): p. 720-728.

6. Yaka, R., et al., *NMDA receptor function is regulated by the inhibitory scaffolding protein, RACK1*. Proceedings of the National Academy of Sciences, 2002. 99(8): p. 5710-5715.
7. Yu, X., et al., *NMDA channel regulation by channel-associated protein tyrosine kinase Src*. Science, 1997. 275(5300): p. 674-678.
8. Lu, Y., et al., *Src activation in the induction of long-term potentiation in CA1 hippocampal neurons*. Science, 1998. 279(5355): p. 1363-1367.
9. Superti-Furga, G., et al., *Csk inhibition of c-Src activity requires both the SH2 and SH3 domains of Src*. The EMBO Journal, 1993. 12(7): p. 2625-2634.
10. O'Dell, T., E. Kandel, and S. Grant, *Long-term potentiation in the hippocampus is blocked by tyrosine kinase inhibitors*. Nature, 1991. 353(6344): p. 558-563.
11. Husi, H., et al., *Proteomic analysis of NMDA receptor-adhesion protein signaling complexes*. Nature Neuroscience, 2000. 3(7): p. 661-669.
12. Niethammer, M., E. Kim, and M. Sheng, *Interaction between the C terminus of NMDA receptor subunits and multiple members of the PSD-95 family of membrane-associated guanylate kinases*. The Journal of Neuroscience, 1996. 16(7): p. 2157-2163.
13. Aarts, M., et al., *Treatment of ischemic brain damage by perturbing NMDA receptor-PSD-95 protein interactions*. Science, 2002. 298(5594): p. 846-850.
14. Wheeler-Aceto, H., F. Porreca, and A. Cowan, *The rat paw formalin test: comparison of noxious agents*. Pain, 1990. 40(2): p. 229-238.

Although the invention has been described in detail for purposes of clarity of understanding, certain modifications may be practiced within the scope of the appended claims. All publications (including, e.g., journal articles, accession numbers, websites and the like) and patent documents cited in this application are hereby incorporated by reference in their entirety for all purposes to the same extent as if each were so individually denoted. To the extent difference sequences might be associated with the same accession number at different times, the sequence associated with the accession number at the effective filing date is meant. The effective filing date means the earliest priority date at which the accession number at issue is disclosed. Unless otherwise apparent from the context any element, embodiment, step, feature or aspect of the invention can be performed in combination with any other.

| List of Sequences | | |
|---|---|---|
| Tat: | YGRKKRRQRRR | SEQ ID NO: 2 |
| Src40-49: | KPASADGHRG | SEQ ID NO: 5 |
| sSrc40-49: | GAAKRPSDGH | SEQ ID NO: 6 |
| Src40-58: | KPASADGHRG P SAAFVPAA | SEQ ID NO: 7 |
| sSrc40-58: | AGSHAPFPSP A RAGVAPDA | SEQ ID NO: 8 |
| Src40-49-Tat: | KPASADGHRGYGRKKRRQRRR | SEQ ID NO: 9 |
| Tat-Src40-49: | YGRKKRRQRRRKPASADGHRG | SEQ ID NO: 10 |
| sSrc 40-49-Tat | GAAKRPSGDHYGRKKRRQRRR | SEQ ID NO: 11 |
| Src 30-39: | GAFPASQTPS | SEQ ID NO: 12 |
| Src 30-49: | GAFPASQTPSKPASADGHRG | SEQ ID NO: 13 |
| Src 35-49: | SQTPSKPASADGHRG | SEQ ID NO: 14 |
| Src 40-54: | PASADGHRGPSAAF | SEQ ID NO: 15 |
| ND2 2.1.4: | NLYFYLRLIYSTSITLLPMSNNVKMKWQFEHTK (289-321) | SEQ ID NO: 16 |
| ND2 peptide sequences | | |
| 1. ND2 289-309: | NLYFYLRLIYSTSITLLPMSN | SEQ ID NO: 17 |
| 2. ND2 291-303: | YFYLRLIYSTSIT | SEQ ID NO: 18 |
| 3. Tat-ND2 291-303: | YGRKKRRQRRR YFYLRLIYSTSIT | SEQ ID NO: 19 |
| 4. ND2 299-318: | STSITLLPMSNNVKMKWQFE | SEQ ID NO: 20 |
| 5. ND2 302-321: | ITLLPMSNNVKMKWQFEHTK | SEQ ID NO: 21 |
| 6. ND2 307-321: | MSNNVKMKWQFEHTK | SEQ ID NO: 22 |
| 7. ND2 310-321: | NVKMKWQFEHTK | SEQ ID NO: 23 |
| 8. sND2 310-321: | KWVQHTKFEMKN | SEQ ID NO: 24 |
| 9. ND2 314-321: | KWQFEHTK | SEQ ID NO: 25 |
| 10. Tat-ND2 310-321 | YGRKKRRQRRRNVKMKWQFEHTK | SEQ ID NO: 26 |
| 11. Scrambled Tat-ND2 310-321: | YGRKKRRQRRRKWVQHTKFEMKN | SEQ ID NO: 27 |

| | | |
|---|---|---|
| 12. ND2 307-318 | MSNNVKMKWQFE | SEQ ID NO: 28 |
| 13. ND2 310-318 | NVKMKWQFE | SEQ ID NO: 29 |
| 14. ND2 310-316 | NVKMKWQ | SEQ ID NO: 30 |
| 15. ND2 310-314 | NVKMK | SEQ ID NO: 31 |
| 16. Myr-ND2 | myristoyl-NVKMKWQFEHTK | SEQ ID NO: 32 |
| 17. Myr2-ND2 | myristoyl- MSNNVKMKWQFEHTK | SEQ ID NO: 33 |

What is claimed is:

1. An ND2 peptide, the amino acid sequence of which consists of up to 20 residues of SEQ ID NO:60 including residues 310-321, the peptide inhibiting ND2 interaction with Src, wherein the peptide is lipidated or linked to an internalization peptide.

2. The ND2 peptide of claim 1, wherein the ND2 peptide is linked to an internalization peptide.

3. The ND2 peptide of claim 2, wherein the internalization peptide is linked to the N-terminus of ND2 peptide.

4. The ND2 peptide of claim 2, wherein the internalization peptide is linked to the C-terminus of the ND2 peptide.

5. The ND2 peptide of claim 2, wherein the internalization peptide and ND2 peptide are linked as a fusion peptide.

6. The ND2 peptide of claim 2, wherein the internalization peptide includes at least 5 arginine or lysine residues and has a total length of up to 15 amino acids.

7. The ND2 peptide of claim 2, wherein the internalization peptide is a Tat peptide.

8. The ND2 peptide of claim 1, wherein the ND2 peptide consists of amino acids 307-321, of SEQ ID NO:60.

9. The ND2 peptide of claim 1, wherein the ND2 peptide is lipidated.

10. The ND2 peptide of claim 9, wherein the ND2 peptide is lipidated by being linked to a fatty acid.

11. The ND2 peptide of claim 10, wherein the ND2 peptide is myristoylated.

12. The ND2 peptide of claim 11, wherein the ND2 peptide is myristoylated at its N-terminus.

13. A chimeric peptide up to 25 amino acids in length, comprising an ND2 peptide as defined in claim 1, and an internalization peptide linked to the ND2 peptide.

14. The chimeric peptide of claim 13, wherein the internalization peptide is linked to the N-terminus of ND2 peptide.

15. The chimeric peptide of claim 13, wherein the internalization peptide is linked to the C-terminus of the ND2 peptide.

16. The chimeric peptide of claim 13, wherein the internalization peptide includes at least 5 arginine or lysine residues and has a total length of up to 15 amino acids.

17. The chimeric peptide of claim 13, wherein the internalization peptide is a Tat peptide.

18. The chimeric peptide of claim 13, wherein the ND2 peptide has an amino acid sequence consisting of amino acids 307-321 or 310 to 321 of SEQ ID NO:60.

19. The chimeric peptide of claim 18, wherein the internalization peptide and ND2 peptide are linked as a fusion peptide.

* * * * *

UNITED STATES PATENT AND TRADEMARK OFFICE
CERTIFICATE OF CORRECTION

PATENT NO. : 9,073,976 B2
APPLICATION NO. : 13/842848
DATED : July 7, 2015
INVENTOR(S) : Michael Tymianski et al.

Page 1 of 1

It is certified that error appears in the above-identified patent and that said Letters Patent is hereby corrected as shown below:

In The Claims

In Claim 8, at Column 63, line 52, delete "307-321, of"

and replace it with -- 307-321, or 310-321 of --.

Signed and Sealed this
Fifth Day of January, 2016

Michelle K. Lee
*Director of the United States Patent and Trademark Office*

SEQUENCE LISTING

```
<160> NUMBER OF SEQ ID NOS: 62

<210> SEQ ID NO 1
<211> LENGTH: 10
<212> TYPE: PRT
<213> ORGANISM: Human immunodeficiency virus

<400> SEQUENCE: 1

Gly Arg Lys Lys Arg Arg Gln Arg Arg Arg
1               5                   10

<210> SEQ ID NO 2
<211> LENGTH: 11
<212> TYPE: PRT
<213> ORGANISM: Human immunodeficiency virus

<400> SEQUENCE: 2

Tyr Gly Arg Lys Lys Arg Arg Gln Arg Arg Arg
1               5                   10

<210> SEQ ID NO 3
<211> LENGTH: 11
<212> TYPE: PRT
<213> ORGANISM: Human immunodeficiency virus

<400> SEQUENCE: 3

Phe Gly Arg Lys Lys Arg Arg Gln Arg Arg Arg
1               5                   10

<210> SEQ ID NO 4
<211> LENGTH: 12
<212> TYPE: PRT
<213> ORGANISM: Human immunodeficiency virus

<400> SEQUENCE: 4

Gly Arg Lys Lys Arg Arg Gln Arg Arg Arg Pro Gln
1               5                   10

<210> SEQ ID NO 5
<211> LENGTH: 10
<212> TYPE: PRT
<213> ORGANISM: Homo sapiens

<400> SEQUENCE: 5

Lys Pro Ala Ser Ala Asp Gly His Arg Gly
1               5                   10

<210> SEQ ID NO 6
<211> LENGTH: 10
<212> TYPE: PRT
```

```
<213> ORGANISM: Homo sapiens

<400> SEQUENCE: 6

Gly Ala Ala Lys Arg Pro Ser Asp Gly His
1               5                   10

<210> SEQ ID NO 7
<211> LENGTH: 19
<212> TYPE: PRT
<213> ORGANISM: Homo sapiens

<400> SEQUENCE: 7

Lys Pro Ala Ser Ala Asp Gly His Arg Gly Pro Ser Ala Ala Phe Val
1               5                   10                  15

Pro Ala Ala

<210> SEQ ID NO 8
<211> LENGTH: 19
<212> TYPE: PRT
<213> ORGANISM: Homo sapiens

<400> SEQUENCE: 8

Ala Gly Ser His Ala Pro Phe Pro Ser Pro Ala Arg Ala Gly Val Ala
1               5                   10                  15

Pro Asp Ala

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Pro Ala Ser Ala Asp Gly His Arg Gly Tyr Gly Arg Lys Lys Arg
1               5                   10                  15

Arg Gln Arg Arg Arg
            20

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Gly Arg Lys Lys Arg Arg Gln Arg Arg Lys Pro Ala Ser Ala
1               5                   10                  15

Asp Gly His Arg Gly
            20

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ala Ala Lys Arg Pro Ser Gly Asp His Tyr Gly Arg Lys Lys Arg
```

-continued

```
                1               5                   10                  15
Arg Gln Arg Arg Arg
            20

<210> SEQ ID NO 12
<211> LENGTH: 10
<212> TYPE: PRT
<213> ORGANISM: Homo sapiens

<400> SEQUENCE: 12

Gly Ala Phe Pro Ala Ser Gln Thr Pro Ser
1               5                   10

<210> SEQ ID NO 13
<211> LENGTH: 20
<212> TYPE: PRT
<213> ORGANISM: Homo sapiens

<400> SEQUENCE: 13

Gly Ala Phe Pro Ala Ser Gln Thr Pro Ser Lys Pro Ala Ser Ala Asp
1               5                   10                  15

Gly His Arg Gly
            20

<210> SEQ ID NO 14
<211> LENGTH: 15
<212> TYPE: PRT
<213> ORGANISM: Homo sapiens

<400> SEQUENCE: 14

Ser Gln Thr Pro Ser Lys Pro Ala Ser Ala Asp Gly His Arg Gly
1               5                   10                  15

<210> SEQ ID NO 15
<211> LENGTH: 14
<212> TYPE: PRT
<213> ORGANISM: Homo sapiens

<400> SEQUENCE: 15

Pro Ala Ser Ala Asp Gly His Arg Gly Pro Ser Ala Ala Phe
1               5                   10

<210> SEQ ID NO 16
<211> LENGTH: 33
<212> TYPE: PRT
<213> ORGANISM: Homo sapiens

<400> SEQUENCE: 16

Asn Leu Tyr Phe Tyr Leu Arg Leu Ile Tyr Ser Thr Ser Ile Thr Leu
1               5                   10                  15

Leu Pro Met Ser Asn Asn Val Lys Met Lys Trp Gln Phe Glu His Thr
            20                  25                  30

Lys

<210> SEQ ID NO 17
<211> LENGTH: 21
<212> TYPE: PRT
<213> ORGANISM: Homo sapiens

<400> SEQUENCE: 17

Asn Leu Tyr Phe Tyr Leu Arg Leu Ile Tyr Ser Thr Ser Ile Thr Leu
1               5                   10                  15
```

```
Leu Pro Met Ser Asn
            20

<210> SEQ ID NO 18
<211> LENGTH: 13
<212> TYPE: PRT
<213> ORGANISM: Homo sapiens

<400> SEQUENCE: 18

Tyr Phe Tyr Leu Arg Leu Ile Tyr Ser Thr Ser Ile Thr
1               5                   10

<210> SEQ ID NO 19
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Gly Arg Lys Lys Arg Arg Gln Arg Arg Arg Tyr Phe Tyr Leu Arg
1               5                   10                  15

Leu Ile Tyr Ser Thr Ser Ile Thr
            20

<210> SEQ ID NO 20
<211> LENGTH: 20
<212> TYPE: PRT
<213> ORGANISM: Homo sapiens

<400> SEQUENCE: 20

Ser Thr Ser Ile Thr Leu Leu Pro Met Ser Asn Asn Val Lys Met Lys
1               5                   10                  15

Trp Gln Phe Glu
            20

<210> SEQ ID NO 21
<211> LENGTH: 20
<212> TYPE: PRT
<213> ORGANISM: Homo sapiens

<400> SEQUENCE: 21

Ile Thr Leu Leu Pro Met Ser Asn Asn Val Lys Met Lys Trp Gln Phe
1               5                   10                  15

Glu His Thr Lys
            20

<210> SEQ ID NO 22
<211> LENGTH: 15
<212> TYPE: PRT
<213> ORGANISM: Homo sapiens

<400> SEQUENCE: 22

Met Ser Asn Asn Val Lys Met Lys Trp Gln Phe Glu His Thr Lys
1               5                   10                  15

<210> SEQ ID NO 23
<211> LENGTH: 12
<212> TYPE: PRT
<213> ORGANISM: Homo sapiens

<400> SEQUENCE: 23

Asn Val Lys Met Lys Trp Gln Phe Glu His Thr Lys
```

```
<210> SEQ ID NO 24
<211> LENGTH: 12
<212> TYPE: PRT
<213> ORGANISM: Homo sapiens

<400> SEQUENCE: 24

Lys Trp Val Gln His Thr Lys Phe Glu Met Lys Asn
1               5                   10

<210> SEQ ID NO 25
<211> LENGTH: 8
<212> TYPE: PRT
<213> ORGANISM: Homo sapiens

<400> SEQUENCE: 25

Lys Trp Gln Phe Glu His Thr Lys
1               5

<210> SEQ ID NO 26
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Gly Arg Lys Lys Arg Arg Gln Arg Arg Asn Val Lys Met Lys
1               5                   10                  15

Trp Gln Phe Glu His Thr Lys
            20

<210> SEQ ID NO 27
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Gly Arg Lys Lys Arg Arg Gln Arg Arg Lys Trp Val Gln His
1               5                   10                  15

Thr Lys Phe Glu Met Lys Asn
            20

<210> SEQ ID NO 28
<211> LENGTH: 12
<212> TYPE: PRT
<213> ORGANISM: Homo sapiens

<400> SEQUENCE: 28

Met Ser Asn Asn Val Lys Met Lys Trp Gln Phe Glu
1               5                   10

<210> SEQ ID NO 29
<211> LENGTH: 9
<212> TYPE: PRT
<213> ORGANISM: Homo sapiens

<400> SEQUENCE: 29

Asn Val Lys Met Lys Trp Gln Phe Glu
1               5
```

```
<210> SEQ ID NO 30
<211> LENGTH: 7
<212> TYPE: PRT
<213> ORGANISM: Homo sapiens

<400> SEQUENCE: 30

Asn Val Lys Met Lys Trp Gln
1               5

<210> SEQ ID NO 31
<211> LENGTH: 5
<212> TYPE: PRT
<213> ORGANISM: Homo sapiens

<400> SEQUENCE: 31

Asn Val Lys Met Lys
1               5

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Val Lys Met Lys Trp Gln Phe Glu His Thr Lys
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Ser Asn Asn Val Lys Met Lys Trp Gln Phe Glu His Thr Lys
1               5                   10                  15

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 34

Xaa Gly Lys Lys Lys Lys Lys Gln Lys Lys Lys
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Any amino acid or not present

<400> SEQUENCE: 35

Xaa Arg Lys Lys Arg Arg Gln Arg Arg Arg
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 36

Xaa Gly Ala Lys Lys Arg Arg Gln Arg Arg Arg
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 37

Xaa Ala Lys Lys Arg Arg Gln Arg Arg Arg
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 38

Xaa Gly Arg Lys Ala Arg Arg Gln Arg Arg Arg
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 39

Xaa Arg Lys Ala Arg Arg Gln Arg Arg Arg
1               5                   10
```

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 40

Xaa Gly Arg Lys Lys Ala Arg Gln Arg Arg Arg
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 41

Xaa Arg Lys Lys Ala Arg Gln Arg Arg Arg
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 42

Xaa Gly Arg Lys Lys Arg Arg Gln Ala Arg Arg
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 43

Xaa Arg Lys Lys Arg Arg Gln Ala Arg Arg
1               5                   10

<210> SEQ ID NO 44
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 44

Gly Ser Ser Ser Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Gly Glu Lys Pro
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Arg Arg Gly Gly Gly Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Arg Gln Arg Asp Gly Glu Arg Pro
1               5

<210> SEQ ID NO 48
<211> LENGTH: 13
<212> TYPE: PRT
<213> ORGANISM: Human immunodeficiency virus

<400> SEQUENCE: 48

Tyr Gly Arg Lys Lys Arg Arg Gln Arg Arg Arg Pro Gln
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid other than "Y" or not present

<400> SEQUENCE: 49

Xaa Gly Arg Lys Lys Arg Arg Gln Arg Arg Arg
1               5                   10
```

```
<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 50

Xaa Gly Arg Lys Lys Arg Arg Gln Arg Ala Arg
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 51

Xaa Arg Lys Lys Arg Arg Gln Arg Ala Arg
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 52

Xaa Arg Arg Pro Arg Arg Pro Arg Arg Pro Arg Arg
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 53

Xaa Arg Arg Ala Arg Arg Ala Arg Arg Ala Arg Arg
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (1)..(1)
<223> OTHER INFORMATION: Any amino acid or not present

<400> SEQUENCE: 54

Xaa Arg Arg Arg Ala Arg Arg Ala Arg Arg
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 55

Xaa Arg Arg Arg Pro Arg Arg Arg Pro Arg Arg
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 56

Xaa Arg Arg Pro Arg Arg Pro Arg Arg
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 57

Xaa Arg Arg Ala Arg Arg Ala Arg Arg
1               5

<210> SEQ ID NO 58
<211> LENGTH: 11
<212> TYPE: PRT
<213> ORGANISM: Human immunodeficiency virus

<400> SEQUENCE: 58

Arg Arg Arg Gln Arg Arg Lys Lys Arg Gly Tyr
1               5                   10

<210> SEQ ID NO 59
<211> LENGTH: 11
```

```
<212> TYPE: PRT
<213> ORGANISM: Human immunodeficiency virus

<400> SEQUENCE: 59

Gly Arg Lys Lys Arg Arg Gln Arg Arg Pro
1               5                   10

<210> SEQ ID NO 60
<211> LENGTH: 347
<212> TYPE: PRT
<213> ORGANISM: Homo sapiens

<400> SEQUENCE: 60

Met Asn Pro Leu Ala Gln Pro Val Ile Tyr Ser Thr Ile Phe Ala Gly
1               5                   10                  15

Thr Leu Ile Thr Ala Leu Ser Ser His Trp Phe Phe Thr Trp Val Gly
                20                  25                  30

Leu Glu Met Asn Met Leu Ala Phe Ile Pro Val Leu Thr Lys Lys Met
            35                  40                  45

Asn Pro Arg Ser Thr Glu Ala Ala Ile Lys Tyr Phe Leu Thr Gln Ala
        50                  55                  60

Thr Ala Ser Met Ile Leu Leu Met Ala Ile Leu Phe Asn Asn Met Leu
65                  70                  75                  80

Ser Gly Gln Trp Thr Met Thr Asn Thr Asn Gln Tyr Ser Ser Leu
                85                  90                  95

Met Ile Met Met Ala Met Ala Met Lys Leu Gly Met Ala Pro Phe His
                100                 105                 110

Phe Trp Val Pro Glu Val Thr Gln Gly Thr Pro Leu Thr Ser Gly Leu
                115                 120                 125

Leu Leu Leu Thr Trp Gln Lys Leu Ala Pro Ile Ser Ile Met Tyr Gln
            130                 135                 140

Ile Ser Pro Ser Leu Asn Val Ser Leu Leu Thr Leu Ser Ile Leu
145                 150                 155                 160

Ser Ile Met Ala Gly Ser Trp Gly Gly Leu Asn Gln Thr Gln Leu Arg
                165                 170                 175

Lys Ile Leu Ala Tyr Ser Ser Ile Thr His Met Gly Trp Met Met Ala
                180                 185                 190

Val Leu Pro Tyr Asn Pro Asn Met Thr Ile Leu Asn Leu Thr Ile Tyr
            195                 200                 205

Ile Ile Leu Thr Thr Thr Ala Phe Leu Leu Leu Asn Leu Asn Ser Ser
210                 215                 220

Thr Thr Thr Leu Leu Leu Ser Arg Thr Trp Asn Lys Leu Thr Trp Leu
225                 230                 235                 240

Thr Pro Leu Ile Pro Ser Thr Leu Leu Ser Leu Gly Gly Leu Pro Pro
                245                 250                 255

Leu Thr Gly Phe Leu Pro Lys Trp Ala Ile Ile Glu Glu Phe Thr Lys
                260                 265                 270

Asn Asn Ser Leu Ile Ile Pro Thr Ile Met Ala Thr Ile Thr Leu Leu
            275                 280                 285

Asn Leu Tyr Phe Tyr Leu Arg Leu Ile Tyr Ser Thr Ser Ile Thr Leu
        290                 295                 300

Leu Pro Met Ser Asn Asn Val Lys Met Lys Trp Gln Phe Glu His Thr
305                 310                 315                 320

Lys Pro Thr Pro Phe Leu Pro Thr Leu Ile Ala Leu Thr Thr Leu Leu
                325                 330                 335
```

```
Leu Pro Ile Ser Pro Phe Met Leu Met Ile Leu
        340                 345

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 61

Xaa Phe Gly Arg Lys Lys Arg Arg Gln Arg Arg Arg
1               5                   10

<210> SEQ ID NO 62
<211> LENGTH: 20
<212> TYPE: PRT
<213> ORGANISM: Human immunodeficiency virus

<400> SEQUENCE: 62

Tyr Gly Arg Lys Lys Arg Arg Gln Arg Arg Arg Lys Leu Ser Ser Ile
1               5                   10                  15

Glu Ser Asp Val
            20
```